(12) United States Patent
Kondo et al.

(10) Patent No.: US 8,822,758 B2
(45) Date of Patent: Sep. 2, 2014

(54) GENE CAPABLE OF INCREASING THE PRODUCTION OF PLANT BIOMASS AND METHOD FOR USING THE SAME

(75) Inventors: Satoshi Kondo, Miyoshi (JP); Norihiro Mitsukawa, Miyoshi (JP); Etsuko Hattori, Toyota (JP); Chikara Ohto, Toyota (JP); Kenichi Ogawa, Kyoto (JP)

(73) Assignees: Toyota Jidosha Kabushiki Kaisha, Aichi (JP); Okayama Prefecture, Okayama (JP)

( * ) Notice: Subject to any disclaimer, the term of this patent is extended or adjusted under 35 U.S.C. 154(b) by 13 days.

(21) Appl. No.: 13/120,901

(22) PCT Filed: Sep. 25, 2009

(86) PCT No.: PCT/JP2009/066650
§ 371 (c)(1),
(2), (4) Date: Mar. 24, 2011

(87) PCT Pub. No.: WO2010/035784
PCT Pub. Date: Apr. 1, 2010

(65) Prior Publication Data
US 2011/0239330 A1 Sep. 29, 2011

(30) Foreign Application Priority Data
Sep. 25, 2008 (JP) .................... 2008-246233

(51) Int. Cl.
*C07K 14/415* (2006.01)
*C12N 15/82* (2006.01)

(52) U.S. Cl.
USPC .......................................... 800/278; 800/295

(58) Field of Classification Search
None
See application file for complete search history.

(56) References Cited

U.S. PATENT DOCUMENTS

| | | | |
|---|---|---|---|
| 6,818,756 B2 | 11/2004 | Sano et al. | |
| 7,176,351 B2 | 2/2007 | Kisaka et al. | |
| 7,790,956 B2 | 9/2010 | Dudits et al. | |
| 2005/0114925 A1 | 5/2005 | Kisaka et al. | |
| 2006/0183137 A1 | 8/2006 | Harper et al. | |
| 2006/0225154 A1 | 10/2006 | Kasukabe et al. | |
| 2007/0039067 A1 | 2/2007 | Feldmann et al. | |
| 2008/0040972 A1 | 2/2008 | Chalivendra et al. | |
| 2008/0113342 A1 | 5/2008 | Cao et al. | |
| 2008/0227639 A1 | 9/2008 | Wu et al. | |
| 2008/0254989 A1 | 10/2008 | Cherian | |
| 2011/0225677 A1 | 9/2011 | Kondo et al. | |
| 2011/0239330 A1 | 9/2011 | Kondo et al. | |
| 2012/0216314 A1 | 8/2012 | Kondo et al. | |

FOREIGN PATENT DOCUMENTS

| | | |
|---|---|---|
| CN | 102165063 | 8/2011 |
| JP | 8266179 | 10/1996 |
| JP | 9-503389 A | 4/1997 |
| JP | 2000-515020 A | 11/2000 |
| JP | 2001-505410 A | 4/2001 |
| JP | 2001252084 | 9/2001 |
| JP | 2001-519659 A | 10/2001 |
| JP | 2005-52114 A | 3/2005 |
| JP | 2005-130770 A | 5/2005 |
| JP | 2007-530063 A | 11/2007 |
| WO | 95/09911 A1 | 4/1995 |
| WO | 98/03631 A1 | 1/1998 |
| WO | 98/10082 A1 | 3/1998 |
| WO | 98/42851 A1 | 10/1998 |
| WO | 98/59039 A1 | 12/1998 |
| WO | 2005/094562 A1 | 10/2005 |
| WO | 2006/005771 A1 | 1/2006 |
| WO | 2006/131547 A1 | 12/2006 |
| WO | 2008/061153 A2 | 5/2008 |
| WO | 2008/062049 A1 | 5/2008 |
| WO | WO 2008061153 A2 * | 5/2008 |
| WO | 2008116829 | 10/2008 |
| WO | 2009060418 | 5/2009 |

OTHER PUBLICATIONS

Peart et al. Ubiquitin ligase-associated protein SGT1 is required for host and nonhost disease resistance in plants. PNAS. 2002. 99(16): 10865-10869.*
Kennel. Principles and practices of nucleic acid hybridization. Progress in Nucleic Acid Research and Molecular Biology. 1971. 11: 259-301.*
Maniatis et al. Molecular Cloning.Cold Spring Harbor Laboratory. 1982. pp. 324-389.*
Weigel et al. Activation tagging in Arabidopsis. Plant Physiology. 2000. 122: 1003-1013.*
Leister. Tandem and segmental gene duplication and recombination in the evolution of plant disease resistance genes. TRENDS in Genetics. 2004. 20(3): 116-122.*

(Continued)

*Primary Examiner* — Cathy Kingdon Worley
*Assistant Examiner* — Ashley K Buran
(74) *Attorney, Agent, or Firm* — Sughrue Mion, PLLC

(57) ABSTRACT

According to the present invention, a technique with which the production of plant biomass can be drastically increased and salt stress resistance can be imparted to a plant is provided.

A gene encoding a protein comprising a common sequence consisting of the amino acid sequence shown in SEQ ID NO: 3 and a common sequence consisting of the amino acid sequence shown in SEQ ID NO: 2 in such order from the N-terminal side and having a coiled-coil structure, a nucleic acid binding site, and a leucine rich repeat structure has been introduced or an expression control region of the gene that is endogenously presented has been altered.

6 Claims, 10 Drawing Sheets

(56) References Cited

OTHER PUBLICATIONS

Sweat et al. Characterization of natural and induced variation in the LOV1 gene, a CC-NBS-LRRR gene conferring victorin sensitivity and disease susceptibilty in Arabidopsis. MPMI. 2008. 21(1): 7-19.*
GenBank Accession No. NM_001084273.1. Published Apr. 20, 2007.*
Theologis et al. GenBank Accession No. NM_001084273.2. Published May 28, 2011.*
GenBank Accession No. AEM36350. At1g58602. Published Oct. 11, 2011. pp. 1-2.*
GenBank Accession No. Q8W3K0. Probable disease resistance protein At1g58602. Published Apr. 29, 2008. pp. 1.*
Michael B. Cooley, et al., "Members of the Arabidopsis HRT/RPP8 Family of Resistance Genes Confer Resistance to Both Viral and Oomycete Pathogens", The Plant Cell, 2000, pp. 663-676, vol. 12.
Jennifer M. Lorang, et al., "Plant disease Susceptibility Conferred by a "Resistance" Gene", Proc. Natl. Acad. Sci. USA, 2007, pp. 14861-14866, vol. 104 No. 37.
Blake C. Meyers, et al., "Genome-Wide Analysis of NBS-LRR-Encoding Genes in Arabidopsis", The Plant Cell, Apr. 2003, pp. 809-834, vol. 15.
Kristen R. Jaglo-Ottosen, et al., "Arabidopsis CBF1 Overexpression Induces COR Genes and Enhances Freezing Tolerance", Science, Apr. 3, 1998, pp. 104-106, vol. 280.
Andrea Chini, et al., "Drought Tolerance Established by Enhanced Expression of the CC-NBS-LRR Gene, ADR1, Requires Salicylic Acid, EDS1 and ABI1", The Plant Journal, 2004, pp. 810-822, vol. 38.
Youssef Belkhadir, et al., "Plant Disease Resistance Protein Signaling: NBS-LRR Proteins and Their Partners", Current Opinion in Plant Biology, 2004, pp. 391-399.
Yasuhiro Kadota, et al., "Protein, Nucleic Acid and Enzyme (PNE)", 2007, pp. 718-723, vol. 52, No. 6.
Mie Kasuga, et al., "Improving Plant Drought, Salt, and Freezing Tolerance by Gene Transfer of a Single Stress-Inducible Transcription Factor", Nature Biotechnology, Mar. 1999, pp. 287-291, vol. 17.
Qiang Liu, et al., "Two Transcription Factors, DREB1 and DREB2, with an EREBP/AP2 DNA Binding Domain Separate Two Cellular Signal Transduction Pathways in Drought-and Low-Temperature-Responsive Gene Expression, Respectively, in Arabidopsis", The Planet Cell, Aug. 1998, pp. 1391-1406, vol. 10.
Stephen T. Chisholm, et al, "Host-Microbe Interactions: Shaping the Evolution of the Plant Immune Response", Cell, Feb. 24, 2006, pp. 803-814.
Lin et al., "Putative Leucine-Rich Repeat Disease Resistance Protein", Database Accession No. 049327, XP002615233 (Jun. 1, 1998).
Lin et al., "Putative Leucine-Rich Repeat Disease Resistance Protein", Database Accession No. 049325, XP002615234 (Jun. 1, 1998).
Lin et al., "Putatie Leucine-Rich Repeat Disease Resistance Protein", Database Accession No. 049328, XP002615235 (Jun. 1, 1998).
Cheng et al., "New Changes in the Plasma-Membrane-Associated Proteome of Rice Roots Under Salt Stress", Proteomics, 9(11):3100-3114 (2009).
Hong et al., "Identification of a Receptor-Like Protein Kinase Gene Rapidly Induced by Abscisic Acid, Dehydration, High Salt, and Cold Treatments in *Arabidopsis thaliana*", Plant Physiology, 113(4):1203-1212 (1997).
De Lorenzo et al., "A Novel Leucine-Rich Repeat Receptor Kinase Regulates the Response of Medicago Truncatula Roots to Salt Stress", Plant Cell, 21(2):668-680 (2009).
Osakabe et al., "Leucine-Rich Repeat Receptor-Like Kinase1 Is a Key Membrane-Bound Regulator of Abscisic Acid Early Signaling in Arabidopsis", Plant Cell, 17:1105-1119 (2005).
Tamura et al., "Osmotic Stress Tolerance of Transgenic Tobacco Expressing a Gene Encoding a Membrane-Located Receptor-Like Protein from Tobacco Plants", Plant Physiology, 131:454-462 (2003).
International Search Report for PCT/JP2010/006254 dated Mar. 9, 2011.
Rounsley et al., *Arabidopis thaliana*—putative leucine-rich repeat disease resistance protein, GenBank Accession No. AAC04912.1, PLN Mar. 11, 2002.
Final Office Action issued in U.S. Appl. No. 13/128,373, dated Nov. 7, 2013.
Non-Final Office Action issued in U.S. Appl. No. 13/128,373 dated Apr. 26, 2013.
Guodong Wang, et al., "A Genome-Wide Functional Investigation into the Roles of Receptor-Like Proteins in Arabidopsis", Plant Physiology, Jun. 2008, pp. 503-517, vol. 147.
Jas Singh, et al., "The GLK1 'Regulon' Encodes Disease Defense Related Proteins and Confers Resistance to Fusarium Graminearum in Arabidopsis", Cereal Res. Commun., 2008, pp. 261-265, vol. 36, Suppl. B.
Ludmila Rizhsky, et al., "When Defense Pathways Collide: the Response of Arabidopsis to a Combination of Drought and Heat Stress", Plant Physiology, 2004, pp. 1-14, vol. 134.
Shin-Han Shiu, et al., "Expansion of the Receptor-Like Kinase/Pelle Gene Family and Receptor-Like Proteins in Arabidopsis", Plant Physiology, Jun. 2003, pp. 530-543, vol. 132.
Hiroshi Magome, et al., "The DDF1 Transcriptional Activator Upregulates Expression of a Gibberellin-Deactivating Gene, GA2ox7, Under High-Salinity Stress in Arabidopsis", The Plant Journal, 2008, pp. 613-626, vol. 56.
Bostjan Kobe, et al., "The Leucine-Rich Repeat as a Protein Recognition Motif", National Diet Library, Apr. 3, 2011.
Meyer et al., "A leucine-rich repeat protein of carrot that exhibits antifreeze activity", FEBS Letters, 447:171-178 (1999).
Osakabe et al., "Functional analysis of a leucine-rich repeat receptor like kinase, RPK1, involved in Aba signal transduction of Arabidopsis", CD p. 4T17-10 (4P-1263) (May 7, 2008) English Explanation.
*Arabidopsis thaliana* AtRLP28 (Receptor Like Protein 28); protein binding (AtRLP28) mRNA, complete CDS, NCBI Reference Sequence: NM_128868.1, http://www.ncbi.nlm.nih.gov/nuccore/18403183?sat=148,satkey=6644359, online Aug. 21, 2009, retrieved Apr. 26, 2013.
Swarbreck et al., Accession No. AEE74273.1, receptor like protein 33 [*Arabidopsis thaliana*], Database (online), Feb. 18, 2011, retrieved from http://www.ncbi.nlm.nih.gov/protein/AEE74273.1 on Dec. 2, 2013.
Wahl et al., "Molecular Hybridization of Immobilized Nucleic Acids: Theoretical Concepts and Practical Considerations", Methods in Enzymology, 1987, 152:399-407.
Tuteja, "Mechanisms of High Salinity Tolerance in Plants", Meth. Enzymol., 428:419-38 (2007) [Abstract, Figures and Legends only].

* cited by examiner

Fig. 1-1

CLUSTAL W (1.83) multiple sequence alignment

```
AT1G59124       -----MAGELISFGIQNLWNLLSQECELFQGVEDQVTELKRDLNMLSSFLKDANAKKHTS
AT1G58807       -----MAGELISFGIQNLWNLLSQECELFQGVEDQVTELKRDLNMLSSFLKDANAKKHTS
AT1G59218       -----MAGELISFGIQNLWNLLSQECELFQGVEDQVTELKRDLNLLSSFLKDADAKKHTS
AT1G58848       -----MAGELISFGIQNLWNLLSQECELFQGVEDQVTELKRDLNLLSSFLKDADAKKHTS
AT1G58602       -----MAGELVSFAVNKLWDLLSHEYTLFQGVEDQVAELKSDLNLLKSFLKDADAKKHTS
AT1G58410       --------MELVSFGVEKLWDRLSQEYDQFKGVEDQVTELKSNLNLLKSFLKDADAKKHIS
AT1G58400       -----MVEAIVSFGVEKLWDRLTQEYEQFQGVEDRIAELKSNLNLLKSFLKDAEAKKNTS
AT1G58390       -----MAGELVSFGIKKLWDLLSQECEQFQGVEDQVTGLKRDLNLLSSFLKDADAKKHTT
AT1G59620       -----MAETLLSFGVEKLWDLLVRESDRFQGVKKQFNELRSDLNKLRCFLEDADAKKHQS
AT1G59780       MQDLYMVDSIVSFGVEKLWKLLSQEYERFQGVEEQITELRDDLKMLMAFLSDADAKKQTR
AT1G50180       -----MAEAVVSFGVEKLWELLSRESARLNGIDEQVDGLKRQLGRLQSLLKDADAKKNET
AT1G53350       -----MAEAVVSFGVEKLWELLSRESARLNGIDEQVDGLKRQLGRLQSLLKDADAKKNET
AT5G43470       -----MAEAFVSFGLEKLWDLLSRESERLQGIDGQLDGLKRQLRSLQSLLKDADAKKHGS
AT5G48620       -----MAEGFVSFGLEKLWDLLSRESERLQGIDEQLDGLKRQLRSLQSLLKDADAKKHGS
AT5G35450       -----MAEGVVSFGVQKLWALLNRESERLNGIDEQVDGLKRQLRGLQSLLKDADAKKHGS
AT1G10920       ------------------------------------------------------------

AT1G59124       AVVKNCVEEIKEIIYDGEDTIETFVLEQNLGKTSGIKKSIRRLACIIPDRRRYALGIGGL
AT1G58807       AVVKNCVEEIKEIIYDGEDTIETFVLEQNLGKTSGIKKSIRRLACIIPDRRRYALGIGGL
AT1G59218       AVVKNCVEEIKEIIYDGEDTIETFVLEQNLGKTSGIKKSIRRLACIIPDRRRYALGIGGL
AT1G58848       AVVKNCVEEIKEIIYDGEDTIETFVLEQNLGKTSGIKKSIRRLACIIPDRRRYALGIGGL
AT1G58602       ALVRYCVEEIKDIVYDAEDVLETFVQKEKLGTTSGIRKHIKRLTCIVPDRREIALYIGHV
AT1G58410       EMVRHCVEEIKDIVYDTEDIIETFILKEKVEMKRGIMKRIKRFASTIMDRRELASDIGGI
AT1G58400       QMVRHCVEEIKEIVYDTENMIETFILKEAARKRSGIIRRITKLTCIKVHRWEFASDIGGI
AT1G58390       AVVRNVVEEIKEIVYDAEDIIETYLLKEKLWKTSGIKMRIRRHACIISDRRRNALDVGGI
AT1G59620       AMVSNTVKEVKEIVYDTEDIIETFLRKKQLGRTRGMKKRIKEFACVLPDRRKIAIDMEGL
AT1G59780       ALARNCLEEIKEITYDAEDIIEIFLLKGSVN---------MRSLACFPGGRREIALQITSI
AT1G50180       ERVRNFLEDVKDIVYDADDIIESFLLNELRGKEKGIKKQVRTLACFLVDRRKFASDIEGI
AT1G53350       ERVRNFLEDVKDIVYDADDIIESFLLNELRGKEKGIKKQVRTLACFLVDRRKFASDIEGI
AT5G43470       DRVRNFLEDVKDLVFDAEDIIESYVLNKLSGKGKGVKKHVRRLACFLTDRHKVASDIEGI
AT5G48620       DRVRNFLEDVKDLVFDAEDIIESYVLNKLRGEGKGVKKHVRRLARFLTDRHKVASDIEGI
AT5G35450       DRVRNFLEDVKDLVFDAEDIIESYVLNKLRGEGKGVKNHVRRLACFLTDRHKVASDIEGI
AT1G10920       ------------------------------------------------------------

AT1G59124       SNRISKVIRDMQSFGVQQAIVDGG-YKQPQGDK--QREMRQKFSKDDDSDFVGLEANVKK
AT1G58807       SNRISKVIRDMQSFGVQQAIVDGG-YKQPQGDK--QREMRQKFSKDDDSDFVGLEANVKK
AT1G59218       SNRISKVIRDMQSFGVQQAIVDGG-YKQPQGDK--QREMRPRFSKDDDSDFVGLEANVKK
AT1G58848       SNRISKVIRDMQSFGVQQAIVDGG-YKQPQGDK--QREMRPRFSKDDDSDFVGLEANVKK
AT1G58602       SKRITRVIRDMQSFGVQQMIVDD--YMHPLRNR--EREIRRTFPKDNESGFVALEENVKK
AT1G58410       SKRISKVIQDMQSFGVQQIITDGSRSSHPLQER--QREMRHTFSRDSENDFVGMEANVKK
AT1G58400       SKRISKVIQDMHSFGVQQMISDGSQSSHLLQER--EREMRQTFSRGYESDFVGLEVNVKK
AT1G58390       RTRISDVIRDMQSFGVQQAIVDGG-YMQPQGDR--QREMRQTFSKDYESDFVGLEVNVKK
AT1G59620       SKRIAKVICDMQSLGVQ---------------------------------------QENVKK
AT1G59780       SKRISKVIQVMQNLGIKSDIMDGV-DSHAQLER--KRELRHTFSSSESESNLVGLEKNVEK
AT1G50180       TKRISEVIVGMQSLGIQHIADGGGRSLSLQER----QREIRQTFSRNSESDLVGLDQSVEE
AT1G53350       TKRISEVIVGMQSLGIQHIADGGGRSLSLQER----QREIRQTFSRNSESDLVGLDQSVEE
AT5G43470       TKRISEVIGEMQSFGIQQ-IIDGGRSLSLQERQRVQREIRQTYPDSSESDLVGVEQSVKE
AT5G48620       TKRISDVIGEMQSFGIQQ-IIDGVRSLSLQERQRVQREIRQTYPDSSESDLVGVEQSVEE
AT5G35450       TKRISKVIGEMQSLGIQQQIIDGGRSLSLQD---IQREIRQTFPNSSESDLVGVEQSVEE
AT1G10920       ----------MKSLGIQE-IIDGASSMSLQERQREQKEIRQTFANSSESDLVGVEQSVEA
                  *:.:*::                                              : .*:
```

Fig. 1-2

```
AT1G59124   LVGYLVDEAN-VQVVSITGMGGLGKTTLAKQVFNHEDVKHQFDGLSWVCVSQDFTRMNVW
AT1G58807   LVGYLVDEAN-VQVVSITGMGGLGKTTLAKQVFNHEDVKHQFDGLSWVCVSQDFTRMNVW
AT1G59218   LVGYLVDEAN-VQVVSITGMGGLGKTTLAKQVFNHEDVKHQFDGLSWVCVSQDFTRMNVW
AT1G58848   LVGYLVDEAN-VQVVSITGMGGLGKTTLAKQVFNHEDVKHQFDGLSWVCVSQDFTRMNVW
AT1G58602   LVGYFVEEDN-YQVVSITGMGGLGKTTLARQVFNHDMVTKKFDKLAWVSVSQDFTLKNVW
AT1G58410   LVGYLVEKDD-YQIVSLTGMGGLGKTTLARQVFNHDVVKDRFDGFAWVSVSQEFTRISVW
AT1G58400   LVGYLVEEDD-IQIVSVTGMGGLGKTTLARQVFNHDVKHQFDRLAWVCVSQEFTRKNVW
AT1G58390   LVGYLVDEEN-VQVVSITGMGGLGKTTLARQVFNHEDVKHQFDRLAWVCVSQEFTRKNVW
AT1G59620   LVGHLVEVEDSSQVVSITGMGGIGKTTLARQVFNHEIVKSHFAQLAWVCVSQQFTRKYVW
AT1G59780   LVEELVGNDS-SHGVSITGLGGLGKTTLARQIFDHDKVKSHFDGLAWVCVSQEFTRKDVW
AT1G50180   LVDHLVENDS-VQVVSVSGMGGIGKTTLARQVFHHDIVRRHFDGFSWVCVSQQFTRKDVW
AT1G53350   LVDHLVENDS-VQVVSVSGMGGIGKTTLARQVFHHDIVRRHFDGFSWVCVSQQFTRKDVW
AT5G43470   LVGHLVENDV-HQVVSIAGMGGIGKTTLARQVFHHDLVRRHFDGFAWVCVSQQFTQKHVW
AT5G48620   LVGHLVENDI-YQVVSIAGMGGIGKTTLARQVFHHDLVRRHFDGFAWVCVSQQFTLKHVW
AT5G35450   LVGPMVEIDN-IQVVSISGMGGIGKTTLARQIFHHDLVRRHFDGFAWVCVSQQFTQKHVW
AT1G10920   LAGHLVENDN-IQVVSISGMGGIGKTTLARQVFHHDMVQRHFDGFAWVFVSQQFTQKHVW
            *. :*        :**:*:*:********:*:*.*: *  :*  ::** ***:**  **

AT1G59124   QKILRDLKPKEE------EKKIMEMTQDTLQGELIRLLETSKSLIVLDDIWEKEDWELIKP
AT1G58807   QKILRDLKPKEE------EKKIMEMTQDTLQGELIRLLETSKSLIVLDDIWEKEDWELIKP
AT1G59218   QKILRDLKPKEE------EKKIMEMTQDTLQGELIRLLETSKSLIVLDDIWEKEDWELIKP
AT1G58848   QKILRDLKPKEE------EKKIMEMTQDTLQGELIRLLETSKSLIVLDDIWEKEDWELIKP
AT1G58602   QNILGDLKPKEEETKEEEKKILEMTEYTLQRELYQLLEMSKSLIVLDDIWKKEDWEVIKP
AT1G58410   QTILQNLTSKER------KDEIQNMKEADLHDDLFRLLESSKTLIVLDDIWKEEDWDLIKP
AT1G58400   QMILQNLTSRET------KDEILQMEEAELHDELFQLLETSKSLIVFDDIWKEEDWGLINP
AT1G58390   QMILQNLTSREK------KDEILQMEEAELHDKLFQLLETSKSLIVFDDIWKDEDWDLIKP
AT1G59620   QTILRKVGPEYIK---------LEMTEDELQEKLFRLLGTRKALIVLDDIWREEDWDMIEP
AT1G59780   KTILGNLSPKYKD---------SDLPEDDIQKKLFQLLETKKALIVFDDLWKREDWYRIAP
AT1G50180   QRILQDLRPYDEG---------IIQMDEYTLQGELFELLESGRYLLVLDDVWKEEDWDRIKA
AT1G53350   QRILQDLRPYDEG---------IIQMDEYTLQGELFELLESGRYLLVLDDVWKEEDWDRIKA
AT5G43470   QRILQELQPHDGD---------ILQMDEYALQRKLFQLLEAGRYLVVLDDVWKKEDWDVIKA
AT5G48620   QRILQELQPHDGN---------ILQMDESALQPKLFQLLETGRYLLVLDDVWKKEDWDRIKA
AT5G35450   QRILQELRPHDGE---------ILQMDEYTIQGKLFQLLETGRYLVVLDDVWKKEDWDRIKE
AT1G10920   QRIWQELQPQNGD---------ISHMDEHILQGKLFKLLETGRYLVVLDDVWKEEDWDRIKA
            : *  .:.              .: :  :: .* .**  : *:*:**:* *** *

AT1G59124   IFPPTKG-WKVLLTSRNESVAMRRNTSYINFKPECLTTEDSWTLFQRIALPM-KDAAEFK
AT1G58807   IFPPTKG-WKVLLTSRNESVAMRRNTSYINFKPECLTTEDSWTLFQRIALPM-KDAAEFK
AT1G59218   IFPPTKG-WKVLLTSRNESVAMRRNTSYINFKPECLTTEDSWTLFQRIALPM-KDAAEFK
AT1G58848   IFPPTKG-WKVLLTSRNESVAMRRNTSYINFKPECLTTEDSWTLFQRIALPM-KDAAEFK
AT1G58602   IFPPTKG-WKLLLTSRNESIVAPTNTKYFNFKPECLKTDDSWKLFQRIAFPI-NDASEFE
AT1G58410   IFPPKKG-WKVLLTSRTESIAMRGDTTYISFKPKCLSIPDSWTLFQSIAMPR-KDTSEFK
AT1G58400   IFPPKK-----------ETIAMHGNRRYVNFKPECLTILESWILFQRIAMPR-VDESEFK
AT1G58390   IFPPNKG-WKVLLTSQNESVAVRGDIKYLNFKPECLAIEDSWTLFQRIAFPK-KDASESK
AT1G59620   IFPLGKG-WKVLLTSRNEGVALRANPNGFIFKPDCLTPEESWTIFRRIVFPG-ENTTEYK
AT1G59780   MFPERKAGWKVLLTSRNDAIHPHCVT----FKPELLTHDECWKLLQRIAFSKQKTITGYI
AT1G50180   VFPHKRG-WKMLLTSRNEGLGLHADPTCFAFRPRILTPEQSWKLFERIVSSR-RDKTEF-
AT1G53350   VFPHKRG-WKMLLTSRNEGLGLHADPTCFAFRPRILTPEQSWKLFERIVSSR-RDKTEF-
AT5G43470   VFPRKRG-WKMLLTSRNEGVIHADPTCLTFRASILNPEESWKLCERIVFPR-RDETEVR
AT5G48620   VFPRKRG-WKMLLTSRNEGVIHADPTCLTFRASILNPEESWKLCERIVFPR-RDETEVR
AT5G35450   VFPRKRG-WKMLLTSRNEGVGLHADPTCLSFRARILNPKESWKLFERIV-PR-RNETEY-
AT1G10920   VFPRKRG-WKMLLTSRNEGVGIHADPKSFGFKTRILTPEESWKLCEKIVFHR-RDETGTL
            :**  :          : :            *:. *  :.* . .*
```

Fig. 1-3

```
AT1G59124    ----IDEEKEELGKLMIKHCGGLPLAIRVLGGMLAEKYTSHDWRRLSENIGSHLVGGRTN
AT1G58807    ----IDEEKEELGKLMIKHCGGLPLAIRVLGGMLAEKYTSHDWRRLSENIGSHLVGGRTN
AT1G59218    ----IDEEKEELGKLMIKHCGGLPLAIRVLGGMLAEKYTSHDWRRLSENIGSHLVGGRTN
AT1G58848    ----IDEEKEELGKLMIKHCGGLPLAIRVLGGMLAEKYTSHDWRRLSENIGSHLVGGRTN
AT1G58602    ----IDEEMEKLGEKMIEHCGGLPLAIKVLGGMLAEKYTSHDWRRLSENIGSHLVGGRTN
AT1G58410    ----VDEEMENMGKKMIKHCGGLSLAVKVLGGLLAAKYTLHDWKRLSENIGSHIVERT--
AT1G58400    ----VDKEMEMMGKQMIKYCGGLPLAVKVLGGLLAAKYTFHDWKRLSENIGCHIVGRTD-
AT1G58390    ----VDEEMEDMGKQMLKHCGGLPLAIKVLGGLLAAKYTMHDWERLSVNIGSDIVGRT--
AT1G59620    ----VDEKMEELGKQMIKHCGGLPLALKVLGGLLVVHFTLDEWKRIYGNIKSHIVGGTS-
AT1G59780    ----IDKEMVKMAKEMTKHCKRLPLAVKLLGGLLDAKHTLRQWKLISENIISHIVVGGTS
AT1G50180    -------KVDEAMGKEMVTYCGGLPLAVKVLGGLLAKKHTVLEWKRVHSNIVTHIVGKSG-
AT1G53350    -------KVDEAMGKEMVTYCGGLPLAVKVLGGLLAKKHTVLEWKRVHSNIVTHIVGKSG-
AT5G43470    ----LDEEMEAMGKEMVTHCGGLPLAVKALGGLLANKHTVPEWKRVFDNIGSQIVGGSW-
AT5G48620    ----LDEEMEAMGKEMVTHCGGLPLAVKALGGLLANKHTVPEWKRVSDNIGSQIVGGSC-
AT5G35450    -------EEMEAIGKEMVTYCGGLPLAVKVLGGLLANKHTASEWKRVSENIGAQIVGKSC-
AT1G10920    SEVRVDEDMEAMGKEMVTCCGGLPLAVKVLGGLLATKHTVPEWKRVYDNIGPHLAGRSS-
                  :  .: *    *  *.**:: ***:*    :.*   :*.   :   **   .:.

AT1G59124    FNDDNNNTCNNVLSLSFEELPSYLKHCFLYLAHFPEDYEIKVENLSYYWAAEGIFQPRHY
AT1G58807    FNDDNNNTCNNVLSLSFEELPSYLKHCFLYLAHFPEDYEIKVENLSYYWAAEGIFQPRHY
AT1G59218    FNDDNNNTCNYVLSLSFEELPSYLKHCFLYLAHFPDDYEINVKNLSYYWAAEGIFQPRHY
AT1G58848    FNDDNNNTCNYVLSLSFEELPSYLKHCFLYLAHFPDDYEINVKNLSYYWAAEGIFQPRHY
AT1G58602    FNDDNNNSCNYVLSLSFEELPSYLKHCFLYLAHFPEDYEIKVENLSYYWAAEEIFQPRHY
AT1G58410    --SGNNSSIDHVLSVSFEELPNYLKHCFLYLAHFPEDHEIDVEKLHYYWAAEGISERRRY
AT1G58400    FSDGNNSSVYHVLSLSFEELPSYLKHCFLYLAHFPEDHNIKVEKLSYCWAAEGILEPRHY
AT1G58390    --SSNNSSIYHVLSMSFEELPSYLKHCFLYLAHFPEDHKINVEKLSYCWAAEGISTAEDY
AT1G59620    FNDKNMSSVYHILHLSFEELPIYLKHCFLYLAQFPEDFTIDLEKLSYYWAAEGMPRPRYY
AT1G59780    SNENDSSSVNHVLSLSFEGLPGYLKHCLLYLASYPEDHEIEIERLSYYWAAEGITYPGNY
AT1G50180    LSDDNSNSVYRVLSLSYEDLPMQLKHCFFYLAHFPEDYKIDVKILFNYWVAEGIITP---F
AT1G53350    LSDDNSNSVYRVLSLSYEDLPMQLKHCFFYLAHFPEDYKIDVKILFNYWVAEGIITP---F
AT5G43470    LDDNSLNSVYRILSLSYEDLPTHLKHCFLNLAHFPEDSEISTYSLFYYWAAEGIY------
AT5G48620    LDDNSLNSVNRILSLSYEDLPTHLKHRFLYLAHFPEDSKIYTQDLFNYWAAEGIY------
AT5G35450    LDDNSLNSVYRILSLSYEDLPTDLKHCFLYLAHFPEDYKIKTRTLYSYWAAEGIY------
AT1G10920    LDDN-LNSIYRVLSLSYENLPMCLKHCFLYLAHFPEYYEIHVKRLFNYLAAEGIITS---S
                  .  .:   :*  :*:* **   ***   ::  **  :*:      *     *      .**   :

AT1G59124    D-GETIRDVGDVYIEELVRRNMVISERDVKTSRFETCHLHDMMREVCLLKAKEENFLQIT
AT1G58807    D-GETIRDVGDVYIEELVRRNMVISERDVKTSRFETCHLHDMMREVCLLKAKEENFLQIT
AT1G59218    D-GEIIRDVGDVYIEELVRRNMVISERDVKTSRFETCHLHDMMREVCLLKAKEENFLQIT
AT1G58848    D-GEIIRDVGDVYIEELVRRNMVISERDVKTSRFETCHLHDMMREVCLLKAKEENFLQIT
AT1G58602    D-GEIIRDVGDVYIEELVRRNMVISERDVKTSRFETCHLHDMMREVCLLKAKEENFLQIT
AT1G58410    D-GETIRDTGDSYIEELVRRNMVISERDVMTSRFETCRLHDMMREICLFKAKEENFLQIV
AT1G58400    H-GQTIRDVGESYIEELVRRNMVIAERDVTTLRFEACHLHDMMREVCLLKAKEENFVQIA
AT1G58390    HNGETIQDVGQSYLEELVRRNMIIWERDATASRFGTCHLHDMMREVCLFKAKEENFLQIA
AT1G59620    D-GATIRKVGDGYIEELVKRNMVISERDARTRRFETCHLHDIVREVCLLKAEEENLIETE
AT1G59780    E-GATIRDVADLYIEELVKRNMVISERDALTSRFEKCQLHDLMREICLLKAKEENFLQIV
AT1G50180    HDGSTIQDTGESYLEELVRRNMVVVEESYLTSRIEYCQMHDMMREVCLSKAKEENFIRVV
AT1G53350    HDGSTIQDTGESYLEELVRRNMVVVEESYLTSRIEYCQMHDMMREVCLSKAKEENFIRVV
AT5G43470    -DGSTIEDSGEYYLEELVRRNLVIADDNYLSWQSKYCQMHDMMREVCLSKAKEENFLQII
AT5G48620    -DGSTIQDSGEYYLEELVRRNLVIADNRYLSLEFNFCQMHDMMREVCLSKAKEENFLQII
AT5G35450    -DGLTILDSGEDYLEELVRRNLVIAEKSNLSWRLKLCQMHDMMREVCISKAKVENFLQII
AT1G10920    DDGTTIQDKGEDYLEELARRNMITIDKNYMFLRKKHCQMHDMMREVCLSKAKEENFLEIF
                  *  *   . :  :*:***:.**::   :           *::**:**:*:   **:  **: .
                                  (3)                                   (2)
```

Fig. 1-4

```
AT1G59124    S------SRPSTANLQSTVTSRRFVYQYPTTLHVEKDINNPKLRALVVVT-----LG--SW
AT1G58807    S------SRPSTANLQSTVTSRRFVYQYPTTLHVEKDINNPKLRALVVVT-----LG--SW
AT1G59218    S------SRTSTGNSLSIVTSRRLVYQYPITLDVEKDINDPKLRSLVVVANTYMFWGGWSW
AT1G58848    S------SRTSTGNSLSIVTSRRLVYQYPITLDVEKDINDPKLRSLVVVANTYMFWGGWSW
AT1G58602    S------NPPSTANFQSTVTSRRLVYQYPTTLHVEKDINNPKLRSLVVT-----LG--SW
AT1G58410    S------NHSPTSNPQTLGASRRFVLHNPTTLHVERYKNNPKLRSLVVVYDDIG---NRRW
AT1G58400    S------ILPPTANSQYPGTSRRFVSQNPTTLHVSRDINNPKLQSLLIVWENR----RKSW
AT1G58390    VKSVGVTSSSTGNSQSPCRSRRLVYQCPTTLHVERDINNPKLRSLVVLWHDLW---VENW
AT1G59620    N-----------SKSPSKPRRLVVKGGDKTDMEGKLKNPKLRSLLFIEELG-------GY
AT1G59780    TDP----TSSSSVHSLASSRSRRLVVYNTSIFSGENDMKNSKLRSLLFIPVG-------YSR
AT1G50180    KVP---TTTSTTINAQSPCRSRRLVLHSGNALHMLGHKDNKKARSVLIFGVEE---KFWKP
AT1G53350    KVP---TTTSTTINAQSPCRSRRLVLHSGNALHMLGHKDNKKARSVLIFGVEE---KFWKP
AT5G43470    IDP---TCTS-TINAQSPSRSRRLSIHSGKAFHILGHKNKTKVRSLIVPRFEE---DYWIR
AT5G48620    KDP---TSTS-TINAQSPSRSRRFSIHSGKAFHILGHRNNPKVRSLIVSRFEE---DFWIR
AT5G35450    KVP---TSTS-TIIAQSPSRSRRLTVHSGKAFHILGHKK--KVRSLLVLGLKE---DLWIQ
AT1G10920    KVS---TATS-AINARSLSKSRRLSVHGGNALPSLGQTINKKVRSLLYFAFED---EFCIL
                     .**:                   *  ::::

AT1G59124    NLAGSSFTRLELLRVLDLIEVKIKGGKLASCIGKLIHLRYLSLEYAEVTHIPYSLGNLKL
AT1G58807    NLAGSSFTRLELLRVLDLIEVKIKGGKLASCIGKLIHLRYLSLEYAEVTHIPYSLGNLKL
AT1G59218    MLLGSSFIRLELLRVLDIHRAKLKGGKLASSIGQLIHLRYLNLKHAEVTHIPYSLGNLKL
AT1G58848    MLLGSSFIRLELLRVLDIHRAKLKGGKLASSIGQLIHLRYLNLKHAEVTHIPYSLGNLKL
AT1G58602    NMAGSSFTRLELLRVLDLVQAKLKGGKLASCIGKLIHLRYLSLEYAEVTHIPYSLGNLKL
AT1G58410    MLSGSIFTRVKLLRVLDLVQAKFKGGKLPSDIGKLIHLRYLSLKDAKVSHLPSSLRNLVL
AT1G58400    KLLGSSFIRLELLRVLDLYKAKFEGRNLPSGIGKLIHLRYLNLDLARVSRLPSSLGNLRL
AT1G58390    KLLGTSFTRLKLLRVLDLFYVDFEGMKLPFGIGNLIHLRYLSLQDAKVSHLPSSLGNLML
AT1G59620    RGFEVWFTRLQLMRVLDLHGVEFGG-ELPSSIGLLIHLRYLSLYRAKASHLPSSMQNLKM
AT1G59780    FSMGSNFIELPLLRVLDLDGAKFKGGKLPSSIGKLIHLKYLSLYQASVTYLPSSLRNLKS
AT1G50180    RG-----FQCLPLLRVLDLSYVQFEGGKLPSSIGDLIHLRFLSLYEAGVSHLPSSLGNLKL
AT1G53350    RG-----FQCLPLLRVLDLSYVQFEGGKLPSSIGDLIHLRFLSLYEAGVSHLPSSLGNLKL
AT5G43470    SASV--FHNLTLLRVLDLSWVKFEGGKLPCSIGGLIHLRYLSLYEAKVSHLPSTMRNLKL
AT5G48620    SASV--FHNLTLLRVLDLSRVKFEGGKLPSSIGGLIHLRFLSLYGAVVSHLPSTMRNLKL
AT5G35450    SASR--FQSLPLLRVLDLSSVKFEGGKLPSSIGGLIHLRFLSLHQAVVSHLPSTIRNLKL
AT1G10920    ESTTPCFRSLPLLRVLDLSRVKFEGGKLPSSIGDLIHLRFLSLHRAWISHLPSSLRNLKL
              *  :  *:****:   .. : *  :*.   ** ****:*.*  *  :  :* ::  **

AT1G59124    LIYLNLASFGR--STFVPNVLMGMQELRYLALPSDMGRKTKLELSNLVKLETLENFSTEN
AT1G58807    LIYLNLASFGR--STFVPNVLMGMQELRYLALPSDMGRKTKLELSNLVKLETLENFSTEN
AT1G59218    LIYLNLVILVSG-STLVPNVLKEMQQLRYLALPKDMGRKTKLELSNLVKLETLKNFSTKN
AT1G58848    LIYLNLVILVSG-STLVPNVLKEMQQLRYLALPKDMGRKTKLELSNLVKLETLKNFSTKN
AT1G58602    LIYLNLHISLSSRSNFVPNVLMGMQELRYLALPSLIERKTKLELSNLVKLETLENFSTKN
AT1G58410    LIYLDIRTDFTD---IFVPNVFMGMRELRYLELPRFMHEKTKLELSNLEKLEALENFSTKS
AT1G58400    LIYLDINVCTKS--LFVPNCLMGMHELRYLRLPFNTSKEIKLGLCNLVNLETLENFSTEN
AT1G58390    LIYLNLDVDTEF--IFVPDVFMRMHELRYLKLPLHMHKKTRLSLRNLVKLETLVYFSTWH
AT1G59620    LLYLNLCVQESC-YIYIPNFLKEMLELKYLSLPLRMDDKSMGEWG---------------
AT1G59780    LLYLNLRINSGQ-LINVPNVFKEMLELRYLSLPWERSSLTKLELGNLLKLETLINFSTKD
AT1G50180    LLCLNLGVADRL-LVHVPNVKEMQELRYLRLPRSMPAKTKLELGDLVNLESLTNFSTKH
AT1G53350    LLCLNLGVADRL-LVHVPNVKEMQELRYLRLPRSMPAKTKLELGDLVNLESLTNFSTKH
AT5G43470    LLYLNLRVDTEE-PIHVPNVKEMIQLRYLSLPLKMDDKTKLELGDLVNLEYLYGFSTQH
AT5G48620    LLFLNLRVDNKE-PIHVPNVKEMLELRYLSLPQEMDDKTKLELGDLVNLEYLWYFSTQH
AT5G35450    MLYLNLHVAIGV-PVHVPNVKEMELRYLSLPLDMHDKTKLELGDLVNLEYLWCFSTQH
AT1G10920    LLYLNLGFNG----MVHVPNVKEMQELRYLQLPMSMHDKTKLELSDLVNLESLMNFSTKY
              ::  *::         :*:  :  * :*:** **
```

Fig. 1-5

```
AT1G59124    SSLEDLCGMVRLSTLNIKLI-EETSLETLAASIGGLKYLEKLEIYDHGS----EMRTKEAG
AT1G58807    SSLEDLCGMVRLSTLNIKLI-EETSLETLAASIGGLKYLEKLEIYDHGS----EMRTKEAG
AT1G59218    CSLEDLRGMVRLRTLTIELR-KETSLETLAASIGGLKYLESLTITDLGS----EMRTKEAG
AT1G58848    CSLEDLRGMVRLRTLTIELR-KETSLETLAASIGGLKYLESLTITDLGS----EMRTKEAG
AT1G58602    SSLEDLRGMVRLRTLTIELI-EETSLETLAASIGGLKYLEKLEIDDLGS----KMRTKEAG
AT1G58410    SSLEDLRGMVRLRTLVIILS-EGTSLQTLSASVCGLRHLENFKIMENAG----VNRMGEER
AT1G58400    SSLEDLRGMVSLRTLTIGLF-KHISKETLFASILGMRHLENLSIRTPDGSSKFKRIMEDG
AT1G58390    SSSKDLCGMTRLMTLAIRLT-RVTSTETLSASISGLRNLEYLYIVGTHS-----KKMREEG
AT1G59620    -----DLQFMTRLRALSIYIR-GRLNMKTLSSSLSKLRDLENLTICYYPMY--APMSGIEG
AT1G59780    SSVTDLHRMTKLRTLQILISGEGLHMETLSSALSMLGHLEDLTVTPSEN------------
AT1G50180    GSVTDLLRMTKLSVLNVIFS-GECTFETLLLSLRELRNLETLSFHDFQKVS-VANHGGEL
AT1G53350    GSVTDLLRMTKLSVLNVIFS-GECTFETLLLSLRELRNLETLSFHDFQKVS-VANHGGEL
AT5G43470    SSVTDLLRMTKLRYLAVSLS-ERCNFETLSSSLRELRNLETLNFLFSLETY-MVDYMGEF
AT5G48620    SSVTDLLRMTKLRNLGVSLS-ERCNFETLSSSLRELRNLEMLNVLFSPEIV-MVDHMGEF
AT5G35450    SSVTDLLRMTKLRFFGVSFS-ERCTFENLSSSLRQFRKLETLSFIYSRKTY-MVDYVGEF
AT1G10920    ASVMDLLHMTKLRELSLFIT-DGSS-DTLSSSLGQLRSLEVLHLYDRQEPR-VAYHGGEI
             **  *. *      :  :         ..*  ::   :  **  : .

AT1G59124    IVFDFVHLKRLWLKLYMPRLSTEQHFPSHLTTLYLESCRLEEDPMPILEKLLQLKELELG
AT1G58807    IVFDFVHLKRLWLKLYMPRLSTEQHFPSHLTTLYLESCRLEEDPMPILEKLLQLKELELG
AT1G59218    IVFDFVYLKTLTLKLYMPRLSKEQHFPSHLTTLYLQHCRLEEDPMPILEKLHQLKELELR
AT1G58848    IVFDFVYLKTLTLKLYMPRLSKEQHFPSHLTTLYLQHCRLEEDPMPILEKLHQLKELELR
AT1G58602    IVFDFVHLKRLRLELYMPRLSKEQHFPSHLTTLYLQHCRLEEDPMPILEKLLQLKELELG
AT1G58410    MVLDFTYLKKLTLSIEMPRLPKIQHLPSHLTVLDLSYCCLEEDPMPILEKLLELKDLSLD
AT1G58400    IVLDAIHLKQLNLRLYMPKLPDEQHFPSHLTSISLDGCCLVEDPLPILEKLLELKEVRLD
AT1G58390    IVLDFIHLKHLLLDLYMPRQ----QHFPSRLTFVKLSECGLEEDPMPILEKLLHLKGVILL
AT1G59620    LVLDCDQLKHLNLRIYMPRLPDEQHFPWHLRNISLAECCLKEDPMPILEKLLQLNEVSLS
AT1G59780    -SVQFKHPK-----LIYRPMLPDVQHFPSHLTTISLVYCFLEEDPMPTLEKLLQLKVVSLW
AT1G50180    LVLDFIHLKDLTLSMHLPRFPDQYRFPPHLAHIWLIGCRMEEDPMPILEKLLHLKSVYLS
AT1G53350    LVLDFIHLKDLTLSMHLPRFPDQYRFPPHLAHIWLIGCRMEEDPMPILEKLLHLKSVYLS
AT5G43470    VLDHFIHLKQLGLAVRMSKIPDQHQFPPHLVHLFLIYCGMEEDPMPILEKLLHLKSVRLA
AT5G48620    VLDHFIHLKQLGLAVRMSKIPDQHQFPPHLAHIHLVHCVMKEDPMPILEKLLHLKSVALS
AT5G35450    VLD-FIHLKKLSLGVHLSKIPDQHQLPPHIAHIYLLFCHMEEDPMPILEKLLHLKSVELR
AT1G10920    VLN-CIHLKELELAIHMPRFPDQYLFHPHLSHIYLWCCSMEEDPIPILERLLHLKSVILT
                *       : .      : ::  : * *: ***:* **:* .*: : *

AT1G59124    FESFSGKKMVCSSGGFPQLQRLSLLKLEEWEDWKVEESSMPLLRTLDIQIHCRL-------
AT1G58807    FESFSGKKMVCSSGGFPQLQRLSLLKLEEWEDWKVEESSMPLLRTLDIQVCRKLKQLPDE
AT1G59218    RKSFSGKEMVCSSGGFPQLQKLSIKGLEEWEDWKVEESSMPVLHTLDIRDCRKLKQLPDE
AT1G58848    RKSFSGKEMVCSSGGFPQLQKLSIKGLEEWEDWKVEESSMPVLHTLDIRDCRKLKQLPDE
AT1G58602    RKSFSGKEMVCSSGGFPQLQKLSISGLKEWEDWKVEESSMPLLLTLNIFDCRKLKQLPDE
AT1G58410    HKSFSGKKMVCSSCGFPQLQKLSISGLKEWEDWKVEESSMPLLLTLNIFDCRKLKQLPDE
AT1G58400    YLSFSGRKMVCSAGGFPQLRKLALDEQEEWEEWIVEEGSMSRLHTLSIWSS---------
AT1G58390    FRAFCGKRMVSSDGGFPQLHRLYIWGLAEWEEWIVEEGSMPRLHTLTIWNCQ---------
AT1G59620    KGSYCGRRMVCSGGGFPQLKKLEIVGLNKWEEWLVEEGSMPLLETLSILDCE---------
AT1G59780    HQSFCGKRMVCSDGGFPQLQKLDLCGLEEWEEWIVEEGSMPRLHKLTIRNDP---------
AT1G50180    YNAYVGRRMVCTGGGFPPLHRLEIWGLDALEEWIVEEGSMPLLHTLHIVDCK---------
AT1G53350    SGAFLGRRMVCSKGGFPQLLALKMSYKKELVEWRVEEGSMPCLRTLTIDNCK---------
AT5G43470    SGAFLGRRMVCSKGGFPQLLALKMSYKKELVEWRVEEGSMPCLRTLTIDNCK---------
AT5G48620    RKAFLGSRMVCSKGGFPQLCVIEISKESELEEWIVEEGSMPCLRTLTIDDCK---------
AT5G35450    YGAFIGRRVVCSKGGFPQLCALGISGESELEEWIVEEGSMPCLRTLTIHDCE---------
AT1G10920    RKAFIGRRMVCSKGGFPQLRALQISEQSELEEWIVEEGSMPCLRDLIIHSCE---------
             FGAFVGRRMVCSKGGFPQLCFLKLEELEELEEWIVEEGRCHFFVL-----------------
              ::  *  :*.:  *** *    ::          :* ***.         :
```

Fig. 1-6

```
AT1G59124    ----------------------------------------------------------------
AT1G58807    HLPSHLTSISLFFCCLEKDPLPTLGRLVYLKELQLGFRTFSGRIMVCSGG--------------
AT1G59218    HLPSHLTSISLFFCCLEEDPMPTLERLVHLKELQLLFRSFSGRIMVCAGSGFPQLHKLKL
AT1G58848    HLPSHLTSISLFFCCLEEDPMPTLERLVHLKELQLLFRSFSGRIMVCAGSGFPQLHKLKL
AT1G58602    HLPSHLTAISLKKCGLED-PIPTLERLVHLKELSLS--ELCGRIMVCTGGGFPQLHKLDL
AT1G58410    ----------------------------------------------------------------
AT1G58400    ----------------------------------------------------------------
AT1G58390    ----------------------------------------------------------------
AT1G59620    ----------------------------------------------------------------
AT1G59780    ----------------------------------------------------------------
AT1G50180    ----------------------------------------------------------------
AT1G53350    ----------------------------------------------------------------
AT5G43470    ----------------------------------------------------------------
AT5G48620    ----------------------------------------------------------------
AT5G35450    ----------------------------------------------------------------
AT1G10920    ----------------------------------------------------------------

AT1G59124    ----------------------------------------------------------------
AT1G58807    -------------------------------GFPQLQKLSIYRLEEWEE---------
AT1G59218    SELDGLEEWIVEDGSMPQLHTLEIRRCPKLKKLPNGFPQLQNLELNELEEWEE---------
AT1G58848    SELDGLEEWIVEDGSMPQLHTLEIRRCPKLKKLPNGFPQLQNLELNELEEWEE---------
AT1G58602    SELDGLEEWIVEDGSMPRLHTLEIRRCLKLKKLPNGFPQLQNLHLTEVEEWEEGMIVKQG
AT1G58410    ----------------------------------------------------------------
AT1G58400    ----------------------------------------------------------------
AT1G58390    ----------------------------------------------------------------
AT1G59620    ----------------------------------------------------------------
AT1G59780    ----------------------------------------------------------------
AT1G50180    ----------------------------------------------------------------
AT1G53350    ----------------------------------------------------------------
AT5G43470    ----------------------------------------------------------------
AT5G48620    ----------------------------------------------------------------
AT5G35450    ----------------------------------------------------------------
AT1G10920    ----------------------------------------------------------------

AT1G59124    ----------------------------------------------------------------
AT1G58807    ----------------------------------------------------------------
AT1G59218    ----------------------------------------------------------------
AT1G58848    ----------------------------------------------------------------
AT1G58602    SMPLLHTLYIWHCPKLPGEQHFPSHLTTVFLLGMYVEEDPMRILEKLLHLKNVSLFQSFS
AT1G58410    ----------------------------------------------------------------
AT1G58400    ----------------------------------------------------------------
AT1G58390    ----------------------------------------------------------------
AT1G59620    ----------------------------------------------------------------
AT1G59780    ----------------------------------------------------------------
AT1G50180    ----------------------------------------------------------------
AT1G53350    ----------------------------------------------------------------
AT5G43470    ----------------------------------------------------------------
AT5G48620    ----------------------------------------------------------------
AT5G35450    ----------------------------------------------------------------
AT1G10920    ----------------------------------------------------------------
```

Fig. 1-7

```
AT1G59124    ----------------------------------------------------------------
AT1G58807    -------------------------------WIVEQGSMPFLHTLYIDDCPKLKKLPDGLQFIYS
AT1G59218    -------------------------------WIVEDGSMPLLHTLRIWNCPKLKQLPDGLRFIYS
AT1G58848    -------------------------------WIVEDGSMPLLHTLRIWNCPKLKQLPDGLRFIYS
AT1G58602    GKRMVCSGGGFPQLQKLSIREIEWEEWIVEQGSMPLLHTLYIGVCPNLKELPDGLRFIYS
AT1G58410    ------------------------------------------------TLKELPDGLRFIYS
AT1G58400    -------------------------------------------------KLKQLPDGLRFIYS
AT1G58390    -------------------------------------------------ELKEIPDGLRFIYS
AT1G59620    -------------------------------------------------KLKELPDGLKFITS
AT1G59780    -------------------------------------------------KLKEIPDGLRFISS
AT1G50180    -------------------------------------------------KLKQLPDGLKYVTC
AT1G53350    -------------------------------------------------KLKQLPDGLKYVTC
AT5G43470    -------------------------------------------------KLKELPDGLKYITS
AT5G48620    -------------------------------------------------KLKELPDGLKYITS
AT5G35450    -------------------------------------------------KLEELPDGLKYVTS
AT1G10920    ----------------------------------------------------------------

AT1G59124    ----------------------------------------------------------------
AT1G58807    LKNLKISER----WKERLSEGGEEYYKVQHIPSVEFYHRVLHIFRSVGGDITGRLLMR
AT1G59218    LKNLTVPKR----WKKRLSKGGEDYYKVQHIPSVEFY---------------------
AT1G58848    LKNLTVPKR----WKKRLSKGGEDYYKVQHIPSVEFY---------------------
AT1G58602    LKNLIVSKR----WKKRLSEGGEDYYKVQHIPSVEFDD--------------------
AT1G58410    LKNLIMGKS----WMERLSERGEEFYKVQNIPFIKFSS--------------------
AT1G58400    IKDLDMDKK----WKEILSEGGEEYYKVQHIPSVKFEKDYK-----------------
AT1G58390    LELVMLGTR----WKKKFSVGGEDYYKVQHIPSVEFIGGYLK----------------
AT1G59620    LKEVHVILNNWDFKKKLSRGGEDYYKVQHIPLVRFL----------------------
AT1G59780    LKELAIRTNEKVFQKKVSKGGEDYYKMQHVPLIRYNWPQEPENNEVIYSFPSPII--
AT1G50180    LKELKIERMKREWTERLVIGGEDYYKVQHIPSVQFINCDH------------------
AT1G53350    LKELKIERMKREWTERLVIGGEDYYKVQHIPSVQFINCDH------------------
AT5G43470    LKELKIEGMKREWKEKLVPGGEDYYKVQHIPDVQFINCDQ------------------
AT5G48620    LKELKIREMKREWKEKLVPGGEDYYKVQHIPDVQFINCDL------------------
AT5G35450    LKELKIEGMKREWKEKLV---GEDYYKVQHIPDVQFFNCDDEQRE-------------
AT1G10920    ----------------------------------------------------------------
```

Fig. 2
 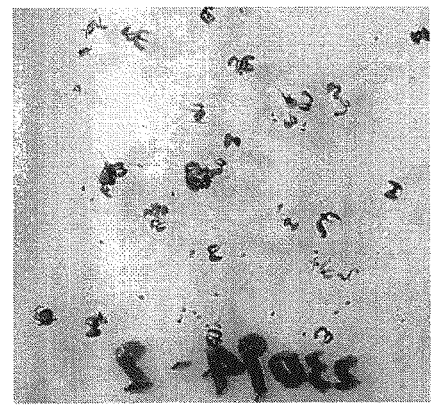
Wild-type plants     Transformed plants

US 8,822,758 B2

GENE CAPABLE OF INCREASING THE PRODUCTION OF PLANT BIOMASS AND METHOD FOR USING THE SAME

CROSS REFERENCE TO RELATED APPLICATION

This application is a National Stage of International Application No. PCT/JP2009/066650 filed Sep. 25, 2009, claiming priority based on Japanese Patent Application No. 2008-246233, filed Sep. 25, 2008, the contents of all of which are incorporated herein by reference in their entirety.

TECHNICAL FIELD

The present invention relates to a plant into which a given gene has been introduced or in which an expression control region of the gene that is endogenously presented has been altered, a method for increasing the production of biomass and imparting salt stress resistance to a plant by introducing a given gene thereinto or altering an expression control region of the gene that is endogenously presented therein, and a method for producing a plant with an increased production of biomass to which environmental stress resistance has been imparted.

BACKGROUND ART

The term "biomass" generally refers to the total amount of organisms that inhabit or exist in a given area. When such term is used with regard to plants, in particular, it refers to dry weight per unit area. Biomass units are quantified in terms of mass or energy. The expression "biomass" is synonymous with "the amount of living matter" or "the mass of an organism." In the case of plant biomass, the term "standing crop" is occasionally used for "biomass." Since plant biomass is generated by fixing atmospheric carbon dioxide with the use of solar energy, it can be regarded as so-called "carbon-neutral energy." Accordingly, an increase of plant biomass is effective for global environmental preservation, the prevention of global warming, and mitigation of greenhouse gas emissions. Thus, technologies for increasing the production of plant biomass have been industrially significant.

Plants are cultivated for the purpose of using some tissues thereof (e.g., seeds, roots, leaves, or stems) or for the purpose of producing various materials, such as fats and oils. Examples of fats and oils produced from plants that have been heretofore known include soybean oil, sesame oil, olive oil, coconut oil, rice oil, cottonseed oil, sunflower oil, corn oil, safflower oil, palm oil, and rapeseed oil. Such fats and oils are extensively used for household and industrial applications. Also, fats and oils produced from plants are used as raw materials for biodiesel fuel or bioplastic, and the applicability thereof is increasing for alternative energy to petroleum.

In particular, an energy crop such as sugar cane can be used as a raw material for biofuel. Hence, the increased production of the total mass of a plant itself (the amount of plant biomass) is expected. Under such circumstances, improvement in productivity per unit of cultivation area is required in order to increase the production of plant biomass. It has been found that if the number of cultivated plants is assumed to be constant per unit of cultivation area, improvement in the amount of biomass per plant would be necessary.

However, it is thought that since many genes are involved in the amount of plant biomass (a so-called "kind of quantitative trait"), individual gene introduction or individual genetic modification cannot lead to an effective increase in production. Meanwhile, a great deal of difficulties are associated with introduction of many genes in a desired state into a plant. Such gene introduction is also problematic in that if successful introduction takes place, desirable traits cannot always be acquired.

Various gene introduction techniques are known as techniques for increasing the production of plant biomass, as disclosed in Patent Documents 1-7, for example. However, in the case of all thereof, attention is focused on the effects of increasing biomass production, while no technique for imparting salt stress resistance to a plant is disclosed.

Patent Document 1: JP Patent Publication (Kohyo) No. 2001-505410 A
Patent Document 2: JP Patent Publication (Kohyo) No. 2001-519659 A
Patent Document 3: JP Patent Publication (Kohyo) No. 2007-530063 A
Patent Document 4: JP Patent Publication (Kokai) No. 2005-130770 A
Patent Document 5: JP Patent Publication (Kohyo) No. 2000-515020 A
Patent Document 6: JP Patent Publication (Kohyo) No. 9-503389 (1997) A
Patent Document 7: JP Patent Publication (Kokai) No. 2005-52114 A

DISCLOSURE OF THE INVENTION

Problem to be Solved by the Invention

In view of the above circumstances, an object of the present invention is to search for genes having novel functions of drastically improving the amount of plant biomass and thus to provide a technique with which the production of plant biomass can be drastically increased and salt stress resistance can be imparted to a plant.

Means for Solving Problem

As a result of intensive studies in order to attain the above object, the present inventors obtained a novel finding to the effect that the amount of plant biomass can be drastically improved and salt stress resistance can be imparted to a plant via the introduction of a gene encoding a protein having a coiled-coil structure, a nucleic acid binding site, and a leucine rich repeat structure in its molecules and comprising characteristic common sequences or the alteration of an expression control region of such gene that is endogenously presented. This has led to the completion of the present invention.

Specifically, the plant of the present invention is characterized in that a gene encoding a protein comprising a common sequence consisting of the amino acid sequence shown in SEQ ID NO: 3 and a common sequence consisting of the amino acid sequence shown in SEQ ID NO: 2 in such order from the N-terminal side and having a coiled-coil structure, a nucleic acid binding site, and a leucine rich repeat structure has been introduced thereinto or an expression control region of the gene that is endogenously presented has been altered therein.

In addition, the method for increasing the production of biomass and imparting salt stress resistance to a plant of the present invention is a method for introducing a gene encoding a protein comprising a common sequence consisting of the amino acid sequence shown in SEQ ID NO: 3 and a common sequence consisting of the amino acid sequence shown in SEQ ID NO: 2 in such order from the N-terminal side and having a coiled-coil structure, a nucleic acid binding site, and a leucine rich repeat structure into a plant or altering an expression control region of the gene that is endogenously presented in a plant.

Further, the plant production method of the present invention is a method comprising the steps of: preparing a transformed plant into which a gene encoding a protein comprising a common sequence consisting of the amino acid sequence shown in SEQ ID NO: 3 and a common sequence consisting of the amino acid sequence shown in SEQ ID NO: 2 in such order from the N-terminal side and having a coiled-coil structure, a nucleic acid binding site, and a leucine rich repeat structure has been introduced or in which an expression control region of the gene that is endogenously presented has been altered; and determining the amount of biomass and salt stress resistance of a progeny plant of the transformed plant and selecting a line that exhibits a significantly improved amount of biomass and salt stress resistance.

According to the present invention, preferably, the protein further comprises a common sequence consisting of the amino acid sequence shown in SEQ ID NO: 1 on the N-terminal side of a common sequence consisting of the amino acid sequence shown in SEQ ID NO: 3.

According to the present invention, the aforementioned gene can be at least one gene selected from the group consisting of AT1G59124, AT1G58807, AT1G59218, AT1G58848, AT1G58602, AT1G58410, AT1G58400, AT1G58390, AT1G59620, AT1G59780, AT1G50180, AT1G53350, AT5G43470, AT5G48620, AT5G35450, and AT1G10920 or a gene functionally equivalent thereto.

According to the present invention, preferably, the aforementioned gene is a gene encoding any one of the following proteins (a) to (c).

(a) A protein comprising the amino acid sequence shown in SEQ ID NO: 5.

(b) A protein comprising an amino acid sequence that has a deletion, a substitution, an addition, or an insertion of one or a plurality of amino acids with respect to the amino acid sequence shown in SEQ ID NO: 5 and having a coiled-coil structure, a nucleic acid binding site, and a leucine-rich repeat structure.

(c) A protein that is encoded by a polynucleotide hybridizing under stringent conditions to a polynucleotide comprising a nucleotide sequence complementary to the nucleotide sequence shown in SEQ ID NO: 4 and has a coiled-coil structure, a nucleic acid binding site, and a leucine rich repeat structure.

In addition, according to the present invention, an example of the above functionally equivalent gene is a gene from an organism other than *Arabidopsis thaliana* which encodes a protein having a coiled-coil structure, a nucleic acid binding site, and a leucine rich repeat structure. An example of an organism other than *Arabidopsis thaliana* is a grape.

Examples of plants to be subjected to the present invention include dicotyledons such as plants of the family Brassicaceae. Examples of plants of the family Brassicaceae include *Arabidopsis thaliana* and rapeseed. Other examples of plants to be subjected to the present invention include monocotyledons such as plants of the family Gramineae. Examples of plants of the family Gramineae include rice and sugarcane.

This description includes part or all of the contents as disclosed in the description and/or drawings of Japanese Patent Application No. 2008-246233, which is a priority document of the present application.

Effects of the Invention

The plant according to the present invention is a plant with a significantly increased amount of biomass compared with wild-type plants to which environmental stress resistance has been imparted. Also, the method for increasing the production of biomass and imparting salt stress resistance to a plant according to the present invention can realize the significantly increased production of biomass compared with target wild-type plants and salt stress resistance can be imparted to a plant. Furthermore, the method for producing a plant according to the present invention makes it possible to produce a plant with a drastically increased amount of biomass compared with wild-type plants which has salt stress resistance. Therefore, through application of the present invention, for example, productivity can be improved when the plant itself is a product and this can be achieved at lower cost. In addition, plants can grow in an environment with a high salt concentration.

BRIEF DESCRIPTION OF THE DRAWINGS

FIG. 1-1 is a characteristic diagram showing the results of alignment analysis using a CLUSTAL W (1.83) multiple sequence alignment program for amino acid sequences encoded by AT1G59124 (SEQ ID NO:29), AT1G58807 (SEQ ID NO:30), AT1G59218 (SEQ ID NO:31), AT1G58848 (SEQ ID NO:32), AT1G58602 (SEQ ID NO:5), AT1G58410 (SEQ ID NO:33), AT1G58400 (SEQ ID NO:34), AT1G58390 (SEQ ID NO:35), AT1G59620 (SEQ ID NO:36), AT1G59780 (SEQ ID NO:37), AT1G50180 (SEQ ID NO:38), AT1G53350 (SEQ ID NO:39), AT5G43470 (SEQ ID NO:40), AT5G48620 (SEQ ID NO:41), AT5G35450 (SEQ ID NO:42), and AT1G10920 (SEQ ID NO:43).

FIG. 1-2 is a characteristic diagram showing the results of alignment analysis using a CLUSTAL W (1.83) multiple sequence alignment program for amino acid sequences encoded by AT1G59124 (SEQ ID NO:29), AT1G58807 (SEQ ID NO:30), AT1G59218 (SEQ ID NO:31), AT1G58848 (SEQ ID NO:32), AT1G58602 (SEQ ID NO:5), AT1G58410 (SEQ ID NO:33), AT1G58400 (SEQ ID NO:34), AT1G58390 (SEQ ID NO:35), AT1G59620 (SEQ ID NO:36), AT1G59780 (SEQ ID NO:37), AT1G50180 (SEQ ID NO:38), AT1G53350 (SEQ ID NO:39), AT5G43470 (SEQ ID NO:40), AT5G48620 (SEQ ID NO:41), AT5G35450 (SEQ ID NO:42), and AT1G10920 (SEQ ID NO:43).

FIG. 1-3 is a characteristic diagram showing the results of alignment analysis using a CLUSTAL W (1.83) multiple sequence alignment program for amino acid sequences encoded by AT1G59124 (SEQ ID NO:29), AT1G58807 (SEQ ID NO:30), AT1G59218 (SEQ ID NO:31), AT1G58848 (SEQ ID NO:32), AT1G58602 (SEQ ID NO:5), AT1G58410 (SEQ ID NO:33), AT1G58400 (SEQ ID NO:34), AT1G58390 (SEQ ID NO:35), AT1G59620 (SEQ ID NO:36), AT1G59780 (SEQ ID NO:37), AT1G50180 (SEQ ID NO:38), AT1G53350 (SEQ ID NO:39), AT5G43470 (SEQ ID NO:40), AT5G48620 (SEQ ID NO:41), AT5G35450 (SEQ ID NO:42), and AT1G10920 (SEQ ID NO:43).

FIG. 1-4 is a characteristic diagram showing the results of alignment analysis using a CLUSTAL W (1.83) multiple sequence alignment program for amino acid sequences encoded by AT1G59124 (SEQ ID NO:29), AT1G58807 (SEQ ID NO:30), AT1G59218 (SEQ ID NO:31), AT1G58848 (SEQ ID NO:32), AT1G58602 (SEQ ID NO:5), AT1G58410 (SEQ ID NO:33), AT1G58400 (SEQ ID NO:34), AT1G58390 (SEQ ID NO:35), AT1G59620 (SEQ ID NO:36), AT1G59780 (SEQ ID NO:37), AT1G50180 (SEQ ID NO:38), AT1G53350 (SEQ ID NO:39), AT5G43470 (SEQ ID NO:40), AT5G48620 (SEQ ID NO:41), AT5G35450 (SEQ ID NO:42), and AT1G10920 (SEQ ID NO:43).

FIG. 1-5 is a characteristic diagram showing the results of alignment analysis using a CLUSTAL W (1.83) multiple sequence alignment program for amino acid sequences encoded by AT1G59124 (SEQ ID NO:29), AT1G58807 (SEQ ID NO:30), AT1G59218 (SEQ ID NO:31), AT1G58848 (SEQ ID NO:32), AT1G58602 (SEQ ID NO:5), AT1G58410 (SEQ ID NO:33), AT1G58400 (SEQ ID NO:34), AT1G58390 (SEQ ID NO:35), AT1G59620 (SEQ ID NO:36), AT1G59780 (SEQ ID NO:37), AT1G50180 (SEQ ID NO:38), AT1G53350 (SEQ ID NO:39), AT5G43470 (SEQ ID NO:40), AT5G48620 (SEQ ID NO:41), AT5G35450 (SEQ ID NO:42), and AT1G10920 (SEQ ID NO:43).

FIG. 1-6 is a characteristic diagram showing the results of alignment analysis using a CLUSTAL W (1.83) multiple sequence alignment program for amino acid sequences encoded by AT1G59124 (SEQ ID NO:29), AT1G58807 (SEQ ID NO:30), AT1G59218 (SEQ ID NO:31), AT1G58848 (SEQ ID NO:32), AT1G58602 (SEQ ID NO:5), AT1G58410 (SEQ ID NO:33), AT1G58400 (SEQ ID NO:34), AT1G58390 (SEQ ID NO:35), AT1G59620 (SEQ ID NO:36), AT1G59780 (SEQ ID NO:37), AT1G50180 (SEQ ID NO:38), AT1G53350 (SEQ ID NO:39), AT5G43470 (SEQ ID NO:40), AT5G48620 (SEQ ID NO:41), AT5G35450 (SEQ ID NO:42), and AT1G10920 (SEQ ID NO:43).

FIG. 1-7 is a characteristic diagram showing the results of alignment analysis using a CLUSTAL W (1.83) multiple sequence alignment program for amino acid sequences encoded by AT1G59124 (SEQ ID NO:29), AT1G58807 (SEQ ID NO:30), AT1G59218 (SEQ ID NO:31), AT1G58848 (SEQ ID NO:32), AT1G58602 (SEQ ID NO:5), AT1G58410 (SEQ ID NO:33), AT1G58400 (SEQ ID NO:34), AT1G58390 (SEQ ID NO:35), AT1G59620 (SEQ ID NO:36), AT1G59780 (SEQ ID NO:37), AT1G50180 (SEQ ID NO:38), AT1G53350 (SEQ ID NO:39), AT5G43470 (SEQ ID NO:40), AT5G48620 (SEQ ID NO:41), AT5G35450 (SEQ ID NO:42), and AT1G10920 (SEQ ID NO:43).

FIG. 2 is a photo of seeds sowed on a plate for wild-type plants and a photo of seeds sowed on a plate for transformed plants into which a fragment containing the AT1G58602 ORF was introduced.

FIG. 3 is a photo showing the aerial parts of wild-type plants and transformed plants into which a fragment containing the AT1G58602 ORF was introduced.

FIG. 4 is a characteristic chart showing results obtained by determining the total amount of biomass in the aerial parts of the wild type plant, the transformed plant into which the LRR-RLK protein gene (AT1G69990) was introduced, the transformed plant into which the LRR-RLK protein gene (AT5G39390) was introduced, the transformed plant into which the LRR protein gene (AT3G05650) was introduced, the transformed plant into which the LRR protein gene (AT2G33080) was introduced, and the transformed plant into which the CC-NBS-LRR protein gene (AT1G58602) was introduced.

BEST MODE FOR CARRYING OUT THE INVENTION

Hereinafter, the present invention is described in detail.

The plant of the present invention is a plant into which a gene encoding a protein comprising characteristic common sequences and having a coiled-coil structure, a nucleic acid binding site, and a leucine rich repeat structure (hereinafter abbreviated as "CC-NBS-LRR") has been introduced or a plant in which an expression control region of the gene that is endogenously presented has been altered. This plant exhibits a significantly improved amount of biomass compared with wild-type plants and salt stress resistance has been imparted thereto. An exogenous target gene is introduced into a plant or an expression control region of such gene that is endogenously presented in the plant is altered such that the expression level of the target gene can be significantly increased to a greater level than the expression of the same in wild-type plants. In addition, the CC-NBS-LRR gene described above may be expressed in all plant tissues of the plant of the present invention. It may also be expressed in at least some of the plant tissues. Here, the term "plant tissue(s)" refers to plant organ(s) such as leaves, stems, seeds, roots, and flowers.

In addition, the term "expression control region" includes in its meaning a promoter region for the binding of RNA polymerase and a region for the binding of a different transcription factor. For the alteration of the transcriptional control region, it is preferable to substitute, for example, a promoter region in the endogenous transcriptional control region with a promoter region that can be more highly expressed than the endogenous promoter region.

CC-NBS-LRR Gene

According to the present invention, the CC-NBS-LRR gene encodes a CC-NBS-LRR protein comprising a common sequence consisting of the amino acid sequence shown in SEQ ID NO: 3 and a common sequence consisting of the amino acid sequence shown in SEQ ID NO: 2 in such order from the N-terminal side. In addition, as described in reference (1) (The Plant Cell, Vol. 15, 809-834, April 2003), CC-NBS-LRR has a nucleic acid binding site and is classified as a kind of a plant resistant protein (also referred to as an "R protein"). In particular, CC-NBS-LRR comprising the above common sequences is classified as "CNL-D" in the above reference. CNL-D is similar to other CC-NBS-LRRs in that it has a coiled-coil structure, a nucleic acid binding site, and a leucine rich repeat structure from the N-terminal side. However, CNL-D is characterized by a portion of a nucleic acid binding motif located between a coiled-coil structure and a leucine rich repeat structure. Therefore, CNL-D is thought to have biological functions differing from those of other CC-NBS-LRRs.

Figure 3:
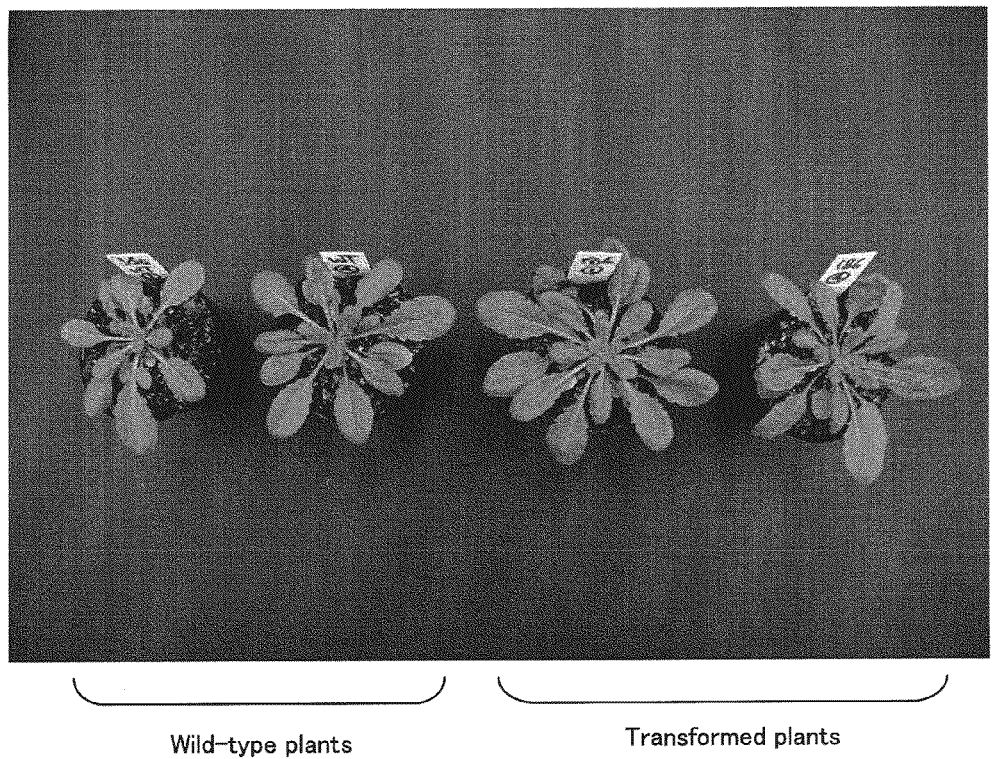
Figure 4:
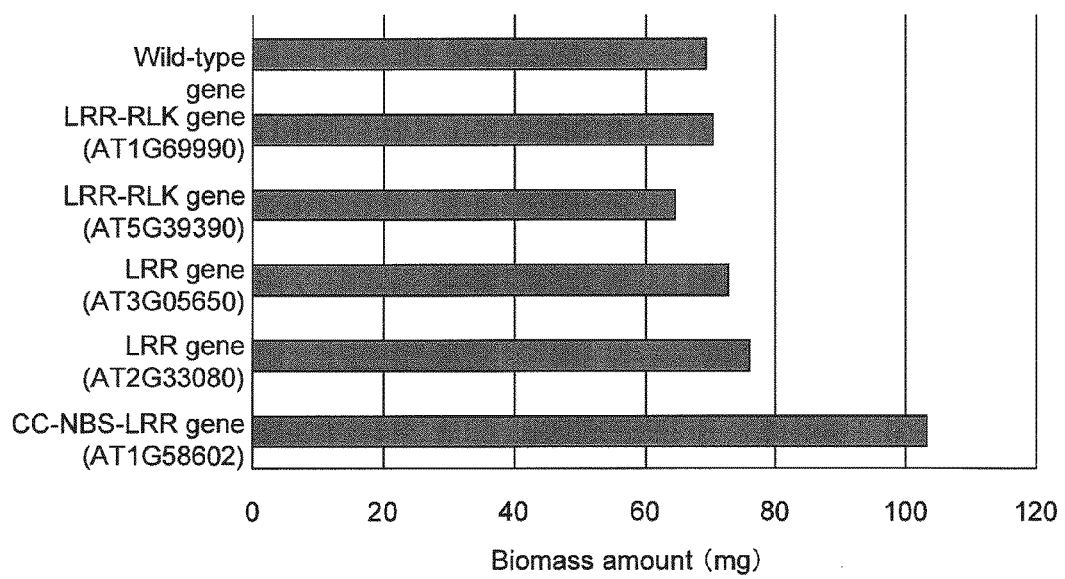

Examples of CC-NBS-LRR classifed as such CNL-D include AT1G59124, AT1G58807, AT1G59218, AT1G58848, AT1G58602, AT1G58410, AT1G58400, AT1G58390, AT1G59620, AT1G59780, AT1G50180, AT1G53350, AT5G43470, AT5G48620, AT5G35450, and AT1G10920 as shown in FIG. 4A of reference (1). FIGS. 1-1 to 1-7 shows the results of alignment analysis using a CLUSTAL W (1.83) multiple sequence alignment program (which can be used with the DDBJ of the National Institute of Genetics (on the web at clustalw.ddbj.nig.ac.jp/top-j)) for the above examples of CC-NBS-LRR classified as CNL-D (provided that the BLOSUM matrix comprising default values was used for an amino acid sequence substitution matrix table).

As shown in FIGS. 1-1 to 1-7, it is understood that the examples of CC-NBS-LRR classified as CNL-D have highly conserved regions (3) and (2) in such order from the N-terminal side. Specifically, these highly conserved regions (3) and (2) can be defined as corresponding to the common sequence consisting of the amino acid sequence shown in SEQ ID NO: 3 and the common sequence consisting of the amino acid sequence shown in SEQ ID NO: 2, respectively. In other words, the common sequence consisting of the amino acid sequence shown in SEQ ID NO: 3 and the common sequence consisting of the amino acid sequence shown in SEQ ID NO: 2 are sequences specific to CNL-D used for CC-NBS-LRR classification as described above. Therefore, the sequences can be used as standard sequences for clear distinguishment from other groups.

In addition, as shown in FIG. 1, it is understood that CC-NBS-LRR classified as CNL-D has a highly conserved region (1) located on the N-terminal side of region (3), in addition to regions (3) and (2). Specifically, this highly conserved region (1) can be defined as corresponding to the common sequence consisting of the amino acid sequence shown in SEQ ID NO: 1. That is to say, CC-NBS-LRR classified as CNL-D can be also defined as further having the common sequence consisting of the amino acid sequence shown in SEQ ID NO: 1 on the N-terminal side in the common sequence consisting of the amino acid sequence shown in SEQ ID NO: 3, in addition to the common sequence consisting of the amino acid sequence shown in SEQ ID NO: 3 and the common sequence consisting of the amino acid sequence shown in SEQ ID NO: 2.

Herein, an amino acid residue denoted by "Xaa" in the amino acid sequence shown in SEQ ID NO: 1 is an arbitrary amino acid and is not limited to any particular amino acid. Note that the 3rd amino acid residue from the N-terminal side in the amino acid sequence shown in SEQ ID NO: 1 is preferably isoleucine (three character code: Ile; single character code: I (and the same applies hereinafter)), leucine (Leu, L), or valine (Val, V). Preferably, the 4th amino acid residue from the N-terminal side in the amino acid sequence shown in SEQ ID NO: 1 is threonine (Thr, T), serine (Ser, S), or alanine (Ala, A). The 6th amino acid residue from the N-terminal side in the amino acid sequence shown in SEQ ID NO: 1 is preferably methionine (Met, M) or leucine (Leu, L). The 9th amino acid residue from the N-terminal side in the amino acid sequence shown in SEQ ID NO: 1 is preferably leucine (Leu, L) or isoleucine (Ile, I). The 16th amino acid residue from the N-terminal side in the amino acid sequence shown in SEQ ID NO: 1 is preferably lysine (Lys, K) or arginine (Arg, R). The 18th amino acid residue from the N-terminal side in the amino acid sequence shown in SEQ ID NO: 1 is preferably valine (Val, V) or isoleucine (Ile, I). The 20th amino acid residue from the N-terminal side in the amino acid sequence shown in SEQ ID NO: 1 is preferably asparagine (Asn, N), aspartic acid (Asp, D), or histidine (His, H). The 22nd amino acid residue from the N-terminal side in the amino acid sequence shown in SEQ ID NO: 1 is preferably glutamic acid (Glu, E) or aspartic acid (Asp, D). That is to say, a more specific example of the common sequence consisting of the amino acid sequence shown in SEQ ID NO: 1 is preferably VS(I/L/V)(T/S/A)G(M/L)GG(L/I)GKTTLA(K/R)Q(V/I)F(N/D/H)H(E/D). In such amino acid sequence, a plurality of amino acids in parentheses represent variations of amino acid residues that can be present at the relevant positions.

Herein, an amino acid residue denoted by "Xaa" in the amino acid sequence shown in SEQ ID NO: 2 is an arbitrary amino acid and is not limited to any particular amino acid. Note that the 2nd amino acid residue from the N-terminal side in the amino acid sequence shown in SEQ ID NO: 2 is preferably histidine (His, H), arginine (Arg, R), or glutamine (Gln, Q). The 3rd amino acid residue from the N-terminal side in the amino acid sequence shown in SEQ ID NO: 2 is preferably leucine (Leu, L) or methionine (Met, M). The 6th amino acid residue from the N-terminal side in the amino acid sequence shown in SEQ ID NO: 2 is preferably methionine (Met, M), isoleucine (Ile, I), or leucine (Leu, L). The 7th amino acid residue from the N-terminal side in the amino acid sequence shown in SEQ ID NO: 2 is preferably methionine (Met, M) or valine (Val, V). The 10th amino acid residue from the N-terminal side in the amino acid sequence shown in SEQ ID NO: 2 is preferably valine (Val, V) or isoleucine (Ile, I). The 12th amino acid residue from the N-terminal side in the amino acid sequence shown in SEQ ID NO: 2 is preferably leucine (Leu, L) or isoleucine (Ile, I). That is to say, a more specific example of the common sequence consisting of the amino acid sequence shown in SEQ ID NO: 2 is preferably C(H/R/Q)(L/M)HD(M/I/L)(M/V)RE(V/I)C(L/I). In such amino acid sequence, a plurality of amino acids in parentheses represent variations of amino acid residues that can be present at the relevant positions.

Herein, an amino acid residue denoted by "Xaa" in the amino acid sequence shown in SEQ ID NO: 3 is an arbitrary amino acid and is not limited to any particular amino acid. Note that the 2nd amino acid residue from the N-terminal side in the amino acid sequence shown in SEQ ID NO: 3 is preferably isoleucine (Ile, I) or leucine (Leu, L). The 6th amino acid residue from the N-terminal side in the amino acid sequence shown in SEQ ID NO: 3 is preferably valine (Val, V) or alanine (Ala, A). The 7th amino acid residue from the N-terminal side in the amino acid sequence shown in SEQ ID NO: 3 is preferably arginine (Arg, R) or lysine (Lys, K). The 10th amino acid residue from the N-terminal side in the amino acid sequence shown in SEQ ID NO: 3 is preferably methionine (Met, M) or leucine (Leu, L). The 11th amino acid residue from the N-terminal side in the amino acid sequence shown in SEQ ID NO: 3 is preferably valine (Val, V) or isoleucine (Ile, I). That is to say, a more specific example of the common sequence consisting of the amino acid sequence shown in SEQ ID NO: 3 is preferably Y(I/L)EEL(V/A)(R/K)RN(M/L)(V/I). In such amino acid sequence, a plurality of amino acids in parentheses represent variations of amino acid residues that can be present at the relevant positions.

Variations of amino acid residues that can be present at given positions are determined based on the following reasons. As described in Reference (2) ("McKee Biochemistry," $3^{rd}$ ed., Chapter 5 Amino Acid•Peptide•Protein 5.1 Amino Acid; editorial supervisor: Atsushi Ichikawa; translation supervisor: Shinichi Fukuoka; publisher: Ryosuke Sone; publishing office: Kagaku-Dojin Publishing Company, INC, ISBN4-7598-0944-9), it is well known that amino acids are classified based on side chains having similar properties (e.g., chemical properties and physical sizes). Also, it is well known that molecular evolutionary substitution frequently takes place among amino acid residues classified in a given group, while retaining protein activity. Based on these concepts, a substitution (mutation) score matrix for amino acid residues (BLOSUM: Blocks of Amino Acid Substitution Matrix) is proposed in FIG. 2 of Reference (3): Henikoff S., Henikoff J. G., Amino-acid substitution matrices from protein blocks, Proc. Natl. Acad. Sci. U.S.A., 89, 10915-10919 (1992) and is broadly used. Reference (2) is based on a finding that amino acid substitutions that take place among amino acids with side chains having similar chemical properties result in less structural or functional changes in the entire protein. According to References (2) and (3) above, amino acid side chain groups to be used in multiple alignment can be considered based on indices such as chemical properties and physical sizes. They are shown as amino acid groups with a score of 0 or higher and preferably as amino acid groups with a score of 1 or higher through the use of the score matrix (BLOSUM) disclosed in Reference (3). Typical groups are the following 8 groups. Further precisely grouped amino acid groups may be amino acid groups with a score of 0 or higher, preferably a score of 1 or higher, and further preferably a score of 2 or higher.

1) Aliphatic Hydrophobic Amino Acid Group (ILMV Group)

This group is a group of amino acids having aliphatic hydrophobic side chains, among neutral nonpolar amino acids disclosed in Reference (1) above, which is composed of V (Val, valine), L (Leu, leucine), I (Ile, isoleucine), and M (Met, methionine). Among amino acids classified as neutral nonpolar amino acids according to Reference (1), FGACWP is not included in this "aliphatic hydrophobic amino acid group" because of the following reasons: G (Gly, glycine) and A (Ala, alanine) are the same size as that of or smaller in size than a methyl group and have weak nonpolar effects; C (Cys, cysteine) may play an important role in S—S bonds and has a property of forming a hydrogen bond with an oxygen atom or a nitrogen atom; F (Phe, phenylalanine) and W (Trp, tryptophan) have side chains with significantly large molecular weights and have strong aromatic effects; P (Pro, proline) has strong imino acid effects, so as to fix the angle of the main chain of the polypeptide.

2) Group Having Hydroxymethylene Group (ST Group)

This group is a group of amino acids (from among neutral polar amino acids) having hydroxymethylene groups in side chains, which is composed of S (Ser, serine) and T (Thr, threonine). Hydroxy groups existing in the side chains of S and T constitute sugar-binding sites, so that these sites are often important for a polypeptide (protein) to have specific activity.

3) Acidic Amino Acid (DE Group)

This group is a group of amino acids having acidic carboxyl groups in side chains, which is composed of D (Asp, aspartic acid) and E (Glu, glutamic acid).

4) Basic Amino Acid (KR Group)

This group is a group of basic amino acids, which is composed of K (Lys, lysine) and R (Arg, arginine). These K and R are positively charged within a wide pH range and have basic properties. On the other hand, H (His, histidine) classified in basic amino acids is almost never ionized at pH 7, so that His not classified in this group.

5) Methylene Group=Polar Group (DHN Group)

This group is characterized in that: in all cases, a methylene group as a side chain binds to an α-carbon element beyond which a polar group is present; and the physical sizes of methylene groups that are nonpolar groups closely resemble from each other. This group is composed of N (Asn, asparagine; polar groups are amide groups), D (Asp, aspartic acid; polar groups are carboxyl groups), and H (His, histidine; polar groups are imidazole groups).

6) Dimethylene Group=Polar Group (EKQR Group)

This group is characterized in that: in all cases, linear hydrocarbon having a length longer than that of a dimethylene group binds as a side chain to an α-carbon element, beyond which a polar group is present; and the physical sizes of dimethylene groups that are nonpolar groups closely resemble from each other. This group is composed of E (Glu, glutamic acid, polar group is a carboxyl group), K (Lys, lysine; polar groups are amino groups), Q (Gln, glutamine; polar groups are amide groups), and R (Arg, arginine; polar groups are imino groups and amino groups).

7) Aromatic Series (FYW Group)

This group is a group of aromatic amino acids having benzene nuclei in the side chains and characterized by having chemical properties unique in aromatic series. This group is composed of F (Phe, phenylalanine), Y (Tyr, tyrosine), and W (Trp, tryptophan).

8) Ring & Polar (HY Group)

This group is a group of amino acids having both ring structures in the side chains and polarity, which is composed of H (H, histidine; both ring structures and polar groups are imidazole groups), and Y (Tyr, tyrosine; ring structures are benzene nuclei and polar groups are hydroxy groups).

As described above, it is understood that: in the given amino acid sequences shown in SEQ ID NOS: 1-3, an amino acid residue denoted as Xaa may be any amino acid; or amino acid residues denoted as Xaa may be substituted with each other within the above groups 1)-8). Hence, in the present invention, the CC-NBS-LRR gene may have any plant origin as long as it has two common sequences consisting of the amino acid sequences shown in SEQ ID NOS: 2 and 3 and preferably three common sequences consisting of the amino acid sequences shown in SEQ ID NOS: 1 to 3.

More specifically, for *Arabidopsis thaliana*, examples of the CC-NBS-LRR gene comprising a common sequence consisting of given amino acid sequences shown in SEQ ID NOS: 1 to 3 include AT1G59124, AT1G58807, AT1G59218, AT1G58848, AT1G58602, AT1G58410, AT1G58400, AT1G58390, AT1G59620, AT1G59780, AT1G50180, AT1G53350, AT5G43470, AT5G48620, AT5G35450, and AT1G10920. According to the present invention, at least one gene selected from the above group of genes is introduced into a plant or an expression control region of the gene that is endogenously presented is altered in a plant. In particular, according to the present invention, the genes identified with AT1G59124, AT1G58807, AT1G59218, AT1G58848, and AT1G58602 and preferably the gene identified with AT1G58602 are introduced into a plant or an expression control region of the relevant gene is altered in a plant.

As examples, the nucleotide sequence of the coding region of the gene identified with AT1G58602 is shown in SEQ ID NO: 4 and the amino acid sequence of CC-NBS-LRR encoded by the gene identified with AT1G58602 is shown in SEQ ID NO: 5.

In addition, according to the present invention, a gene that is functionally equivalent to an above described gene may be introduced into a plant. Here, the term "functionally equivalent gene" refers to, for example, a gene from an organism other than *Arabidopsis thaliana* that encodes CC-NBS-LRR comprising two common sequences consisting of the amino acid sequences shown in SEQ ID NOS: 2 and 3. Further, such a functionally equivalent gene is a gene encoding a protein comprising CC-NBS-LRR, which is an R protein that interacts directly or indirectly with an effector.

An example of an organism other than *Arabidopsis thaliana* is a grape (*Vitis vinifera*). More specifically, examples of the gene of such organism include genes identified with the following accession numbers as *Vitis vinifera* genes: A7Q3G8, A5BY93, A7Q3G6, A5C0R9, and A7Q3H1.

Genes from plants other than *Arabidopsis thaliana* that encode CC-NBS-LRR comprising two common sequences consisting of the amino acid sequences shown in SEQ ID NOS: 2 and 3, which are represented by the above examples, can be readily searched for or identified in the database such as GenBank based on the amino acid sequences encoded by the aforementioned *Arabidopsis thaliana*-derived AT1G58602 genes.

In addition, according to the present invention, a CC-NBS-LRR gene is not limited to the above described CC-NBS-LRR genes comprising the nucleotide sequences and the amino acid sequences identified with the above sequence numbers. Hence, the CC-NBS-LRR gene may be a gene that contains an amino acid sequence having a deletion, a substitution, an addition, or an insertion of one or a plurality of amino acids with respect to the amino acid sequences identified with the above sequence numbers and has activity of functioning as an CC-NBS-LRR gene. Here the term "a plurality of amino acids" refers to 1 to 20, preferably 1 to 10, more preferably 1 to 7, further preferably 1 to 5, and particularly preferably 1 to 3 amino acids, for example. In addition, amino acid deletion, substitution, or addition can be performed by altering a nucleotide sequence encoding the above CC-NBS-LRR gene by a technique known in the art. Mutation can be introduced into a nucleotide sequence by a known technique such as the Kunkel method or the Gapped duplex method or a method based thereon. For example, mutation is introduced with a mutagenesis kit using site-directed mutagenesis (e.g., Mutant-K or Mutant-G (both are trade names of TAKARA Bio)) or the like, or a LA PCR in vitro Mutagenesis series kit (trade name, TAKARA Bio). Also, a mutagenesis method may be: a method using a chemical mutation agent represented by EMS (ethyl methanesulfonate), 5-bromouracil, 2-aminopurine, hydroxylamine, N-methyl-N'-nitro-N nitrosoguanidine, or other carcinogenic compounds; or a method that involves radiation treatment or ultraviolet [UV] treatment typically using X-rays, alpha rays, beta rays, gamma rays, an ion beam, or the like.

Also, CC-NBS-LRR genes may be genes homologous to CC-NBS-LRR genes comprising the nucleotide sequences and the amino acid sequences identified with the above sequence numbers. Here, the term "homologous gene" generally refers to a gene that has evolutionarily branched off from a common ancestor gene, including a homologous gene (ortholog) of 2 types of species and a homologous gene (paralog) generated by overlapping branching that takes place within the same species. In other words, the above term "functionally equivalent gene" refers to a homologous gene such as an ortholog or a paralog. Furthermore, the above term "functionally equivalent gene" may also refer to a gene that does not evolve from a common gene, but simply has analogous functions.

Examples of genes similar to the CC-NBS-LRR genes comprising the nucleotide sequences and the amino acid sequences identified with the above sequence numbers include genes encoding proteins each having an amino acid sequence that has 70% or more, preferably 80% or more, more preferably 90% or more, and most preferably 95% or more similarity to any of such amino acid sequences, a common sequence consisting of the amino acid sequence shown in SEQ ID NO: 1, and having CC-NBS-LRR activity. Here, the value of similarity refers to a value that can be obtained based on default setting using a computer mounted with a BLAST (Basic Local Alignment Search Tool) program and a database containing gene sequence information.

Also, genes similar to the CC-NBS-LRR2C genes comprising the nucleotide sequences and the amino acid sequences identified with the above sequence numbers can be identified by, when the plant genome information remains unclarified, extracting the genome from a target plant or constructing a cDNA library for a target plant and then isolating a genomic region or cDNA hybridizing under stringent conditions to at least some portions of the CC-NBS-LRR genes comprising the nucleotide sequences and the amino acid sequences identified with the above sequence numbers. Here, the term "stringent conditions" refers to conditions under which namely a specific hybrid is formed, but a non-specific hybrid is never formed. For example, such conditions comprise hybridization at 45° C. with 6×SSC (sodium chloride/sodium citrate), followed by washing at 50° C. to 65° C. with 0.2-1×SSC and 0.1% SDS. Alternatively, such conditions comprise hybridization at 65° C. to 70° C. with 1×SSC, followed by washing at 65° C. to 70° C. with 0.3×SSC. Hybridization can be performed by a conventionally known method such as a method described in J. Sambrook et al. Molecular Cloning, A Laboratory Manual, 2nd Ed., Cold Spring Harbor Laboratory (1989).

The plant of the present invention is obtained as a plant that exhibits a significantly improved amount of biomass compared with wild-type plants and salt stress resistance via the introduction of a gene encoding CC-NBS-LRR comprising two common sequences consisting of the amino acid sequences shown in SEQ ID NOS: 2 and 3 thereinto or the alteration of an expression control region of the gene that is endogenously presented therein. An example of a technique for introducing such CC-NBS-LRR gene into a plant is a technique for introducing an expression vector in which an exogenous CC-NBS-LRR gene is arranged under control of a promoter that enables expression within a plant. An example of a technique for altering an expression control region of the gene that is endogenously presented is a technique for altering a promoter for the CC-NBS-LRR gene that is endogenously presented in a target plant.

A preferred example of such technique is a technique for introducing an expression vector, in which the above described CC-NBS-LRR gene is arranged under control of a promoter that enables expression within a plant, into a target plant.

Expression Vector

An expression vector is constructed to contain a promoter that enables expression within a plant and the above described CC-NBS-LRR gene. As a vector serving as a mother body for an expression vector, various conventionally known vectors can be used. For example, plasmids, phages, cosmids, or the like can be used and such vector can be appropriately selected depending on plant cells into which it is introduced and introduction methods. Specific examples of such vector include pBR322, pBR325, pUC19, pUC119, pBluescript, pBluescriptSK, and pBI vectors. Particularly, when a method for introduction of a vector into a plant uses *Agrobacterium*, a pBI binary vector is preferably used. Specific examples of such pBI binary vector include pBIG, pBIN19, pBI101, pBI121, and pBI221.

A promoter to be used herein is not particularly limited, as long as it enables expression of the CC-NBS-LRR gene within a plant. Any known promoter can be appropriately used. Examples of such promoter include a cauliflower mosaic virus 35S promoter (CaMV35S), various actin gene promoters, various ubiquitin gene promoters, a nopaline synthase gene promoter, a tobacco PR1a gene promoter, a tomato ribulose 1,5-bisphosphate carboxylase•oxidase small subunit gene promoter, and a napin gene promoter. Of these, a cauliflower mosaic virus 35S promoter, an actin gene promoter, or a ubiquitin gene promoter can be more preferably used. The use of each of the above promoters enables strong expression of any gene when it is introduced into plant cells.

Also, a promoter having functions of causing site-specific expression in a plant can also be used herein. As such promoter, any conventionally known promoter can be used. When the above described CC-NBS-LRR gene is site-specifically expressed using such promoter, organs of a plant in which the gene is expressed can grow larger than those of wild-type plants.

In addition, an expression vector may further contain other DNA segments in addition to a promoter and the above CC-NBS-LRR gene. Such other DNA segments are not particularly limited and examples thereof include a terminator, a selection marker, an enhancer, and a nucleotide sequence for enhancing translation efficiency. Also, the above recombinant expression vector may further have a T-DNA region. A T-DNA region can enhance efficiency for gene introduction particularly when the above recombinant expression vector is introduced into a plant using *Agrobacterium*.

A transcription terminator is not particularly limited, as long as it has functions as a transcription termination site and may be any known transcription terminator. For example, specifically, a transcription termination region (Nos terminator) of a nopaline synthase gene, a transcription termination region (CaMV35S terminator) of cauliflower mosaic virus 35S, or the like can be preferably used. Of them, the Nos terminator can be more preferably used. In the case of the above recombinant vector, a phenomenon such that an unnecessarily long transcript is synthesized and that a strong promoter decreases the number of copies of a plasmid after introduction into plant cells can be prevented by arranging a transcription terminator at an appropriate position.

As a transformant selection marker, a drug resistance gene can be used, for example. Specific examples of such drug resistance gene include drug resistance genes against hygromycin, bleomycin, kanamycin, gentamicin, chloramphenicol, and the like. Transformed plants can be easily selected by selecting plants that can grow in medium containing the above antibiotics.

An example of a nucleotide sequence for increasing translation efficiency is an omega sequence from tobacco mosaic virus. This omega sequence is arranged in an untranslated region (5'UTR) of a promoter, so that the translation efficiency of the fusion gene can be increased. As such, the recombinant expression vector may contain various DNA segments depending on purposes.

A method for constructing a recombinant expression vector is not particularly limited. To an appropriately selected vector serving as a mother body, the above promoter and the above CC-NBS-LRR gene, a transcription repressor converting polynucleotide, and if necessary, the above other DNA segments may be introduced in an predetermined order. For example, the above gene and a promoter (and, if necessary, a transcription terminator or the like) are linked to construct an expression cassette and then the cassette may be introduced into a vector. In construction of an expression cassette, for example, cleavage sites of DNA segments are prepared to have protruding ends complementary to each other and then performing a reaction with a ligation enzyme, making it possible to specify the order of the DNA segments. In addition, when an expression cassette contains a terminator, DNA segments may be arranged in the following order from upstream: a promoter, the above CC-NBS-LRR gene, and a terminator. Also, reagents for construction of an expression vector (that is, types of restriction enzymes, ligation enzymes, and the like) are also not particularly limited. Hence, commercially available reagents can be appropriately selected and used.

Also, a method for replicating (a method for producing) the above expression vector is not particularly limited and conventionally known replication methods can be used herein. In general, such expression vector may be replicated within *Escherichia coli* as a host. At this time, preferred types of *Escherichia coli* may be selected depending on the types of vector.

Transformation

The above-described expression vector is introduced into a target plant by a general transformation method. A method for introducing an expression vector into plant cells (transformation method) is not particularly limited. Conventionally known appropriate introduction methods can be used depending on plant cells. Specifically, a method using *Agrobacterium* or a method that involves direct introduction into plant cells can be used, for example. As a method using *Agrobacterium*, a method described in Bechtold, E., Ellis, J. and Pelletier, G. (1993) In Planta *Agrobacterium*-mediated gene transfer by infiltration of adult *Arabidopsis* plants. C. R. Acad. Sci. Paris Sci. Vie, 316, 1194-1199, or a method described in Zyprian E, Kado Cl, *Agrobacterium*-mediated plant transformation by novel mini-T vectors in conjunction with a high-copy vir region helper plasmid, Plant Molecular Biology, 1990, 15(2), 245-256 can be employed, for example.

As a method for directly introducing an expression vector into plant cells, microinjection, electroporation, a polyethylene glycol method, a particle gun method, protoplast fusion, a calcium phosphate method, or the like can be employed.

Also, when a method for directly introducing DNA into plant cells is employed, DNA that can be used herein contains transcriptional units required for the expression of a target gene, such as a promoter and a transcription terminator, and a target gene. Vector functions are not essential in such case. Moreover, a DNA that contains a protein coding region alone of a target gene having no transcriptional unit may be used herein, as long as it is integrated into a host's transcriptional unit and then the target gene can be expressed.

Examples of plant cells into which the above expression vector or an expression cassette containing no expression vector, but a target gene is introduced include cells of each tissue of plant organs such as flowers, leaves, and roots, calluses, and suspension-cultured cells. At this time, an appropriate expression vector may be constructed according to the type of plant to be produced or a versatile expression vector may be constructed in advance and then introduced into plant cells.

Plants into which an expression vector is introduced or in other words, target plants for the increase of biomass production are not particularly limited. Specifically, any plant can be expected to have effects of increasing biomass production by introducing the above CC-NBS-LRR gene thereinto. Examples of target plants include, but are not limited to, dicotyledons and monocotyledons, such as plants (see below) belonging to the families Brassicaceae, Gramineae, Solanaceae, Leguminosae, Salicaceae, and the like.

Family Brassicaceae: *Arabidopsis thaliana*, oilseed rape (*Brassica rapa, Brassica napus*), cabbage (*Brassica oleracea* var. *capitata*), rapeseed (*Brassica rapa, Brassica napus*), field mustard (*Brassica rapa, Brassica napus*), napa (*Brassica rapa* var. *pekinensis*), ging-geng-cai (*Brassica rapa* var. *chinensis*), turnip (*Brassica rapa* var. *rapa*), turnip greens (*Brassica rapa* var. *hakabura*), potherb mustard (*Brassica rapa* var. *lancinifolia*), Komatsuna (*Brassica rapa* var. *peruviridis*), pak choi (*Brassica rapa* var. *chinensis*), daikon (*Brassica Raphanus sativus*), Japanese horseradish (*Wasabia japonica*), and the like.

Family Solanaceae: tobacco (*Nicotiana tabacum*), eggplant (*Solanum melongena*), potato (*Solaneum tuberosum*), tomato (*Lycopersicon lycopersicum*), chile pepper (*Capsicum annuum*), petunia (*Petunia*), and the like.

Family Leguminosae: soy (*Glycine max*), pea (*Pisum sativum*), broad bean (*Vicia faba*), Wisteria (*Wisteria floribunda*), peanuts (*Arachis hypogaea*), bird's foot trefoil (*Lotus corniculatus* var. *japonicus*), common bean (*Phaseolus vulgaris*), azuki bean (*Vigna angularis*), acacia (*Acacia*), and the like.

Family Asteraceae: florists' daisy (*Chrysanthemum morifolium*), sunflower (*Helianthus annuus*), and the like.

Family Arecaceae: oil palm (*Elaeis guineensis, Elaeis oleifera*), coconut (*Cocos nucifera*), date palm (*Phoenix dactylifera*), copernicia (*Copernicia*), and the like.

Family Anacardiaceae: wax tree (*Rhus succedanea*), cashew nut (*Anacardium occidentale*), lacquer tree (*Toxicodendron vernicifluum*), mango (*Mangifera indica*), pistachio (*Pistacia vera*), and the like.

Family Cucurbitaceae: pumpkin (*Cucurbita maxima, Cucurbita moschata, Cucurbita pepo*), cucumber (*Cucumis sativus*), snake gourd (*Trichosanthes cucumeroides*), gourd (*Lagenaria siceraria* var. *gourda*), and the like.

Family Rosaceae: almond (*Amygdalus communis*), rose (*Rosa*), strawberry (*Fragaria*), cherry (*Prunus*), apple (*Malus pumila* var. *domestica*), and the like.
Family Caryophyllaceae: carnation (*Dianthus caryophyllus*) and the like.
Family Salicaceae: poplar (*Populus trichocarpa, Populus nigra*, or *Populus tremula*) and the like.
Family Gramineae: corn (*Zea mays*), rice (*Oryza sativa*), barley (*Hordeum vulgare*), wheat (*Triticum aestivum*), bamboo (*Phyllostachys*), sugarcane (*Saccharum officinarum*), napier grass (*Pennisetum pupureum*), erianthus (*Erianthus ravenae*), miscanthus (Japanese silver grass) (*Miscanthus virgatum*), sorghum (*Sorghum*), switchgrass (*Panicum*), and the like.
Family Liliaceae: tulip (*Tulipa*), lily (*Lilium*), and the like.

Of these examples, energy crops such as sugarcane, corn, rapeseed, and sunflower, which can serve as raw materials for biofuel, may be preferable targets. This is because the costs of biofuels such as bioethanol, biodiesel, biomethanol, bioDME, bioGTL (BTL), and biobutanol can be reduced by increasing the production of biomass of such energy crop Also, as described above, CC-NBS-LRR genes that can be used in the present invention can be isolated from various plants and used. Such CC-NBS-LRR genes can be appropriately selected and used, depending on the types of target plants for the increase of biomass production. Specifically, when a target plant for the increase of biomass production is a monocotyledon, a CC-NBS-LRR gene that has been isolated from a monocotyledon is preferably introduced.

In addition, in the present invention, even when a target plant for the increase of biomass production is a monocotyledon, a dicotyledon-derived CC-NBS-LRR gene may be introduced. Specifically, for example, the *Arabidopsis thaliana*-derived CC-NBS-LRR gene (SEQ ID NO: 4) may be introduced into not only dicotyledons, but also a variety of plants that are classified as monocotyledons.

Other Steps and Methods

After the above transformation, a step of selecting proper transformants from plants can be performed by a conventionally known method. Such selection method is not particularly limited. For example, selection can be made based on drug resistance such as hygromycin resistance. Alternatively, after the growth of transformants, a transformant with a significant increase in biomass production compared with a wild type plant may be selected by determining the weight of a plant itself or its arbitrary organ or tissue.

Also, progeny plants can be obtained from transformed plants obtained by transformation according to a conventional method. Progeny plants retaining a trait into which the CC-NBS-LRR gene has been introduced or in which an expression control region of the CC-NBS-LRR gene that is endogenously presented has been altered are selected based on their amounts of biomass. Therefore, a stable plant line capable of exerting the increased production of biomass because of having the above trait can be produced. Also, plant cells or reproductive materials, such as seeds, fruits, stocks, calluses, tubers, cut ears, or lumps, may be obtained from a transformed plant or an offspring plant thereof. A stable plant line capable of exerting the increased production of biomass because of having the above trait can be mass-produced from such cells or materials.

In addition, the plant of the present invention may include a matter comprising at least any one of an adult plant, plant cells, plant tissue, callus, and seeds. That is, according to the present invention, any matter in a state that allows it to eventually grow to become a plant can be regarded as a plant. In addition, the above plant cells include plant cells in various forms. Examples of such plant cells include suspension-cultured cells, protoplasts, and leaf sections. As a result of proliferation/differentiation of such plant cells, a plant can be obtained. In addition, a plant can be reproduced from plant cells by a conventionally known method depending on the types of plant cells.

As explained above, according to the present invention, plants capable of exerting the significantly increased production of biomass per plant compared with wild-type plants and having salt stress resistance can be provided by introducing a CC-NBS-LRR gene comprising the above specific common sequences thereinto or altering an expression control region of the gene that is endogenously presented therein. Here, the term "significantly increased production of biomass" refers to a situation in which the total weight of each plant is statistically significantly increased compared with the same of a wild-type plant. In this case, even when some plant tissues become specifically large and the sizes of the other tissues are equivalent to those of a wild-type plant, it is concluded that the production of biomass is increased if the total weight of the entire plant is large. In addition, the term "salt stress resistance" refers to a situation in which the upper limit of the salt concentration at which the plant can grow is significantly greater than in the case of a wild-type plant. In other words, the term "salt stress resistance" refers to a situation in which a plant does not experience poor growth or death caused by withering even if the concentration of salt in a growth environment such as soil or medium is sufficiently high to cause a wild-type plant to experience poor growth or death due to withering. Specifically, a plant into which the CC-NBS-LRR gene comprising the above specific common sequences has been introduced or in which an expression control region of the CC-NBS-LRR gene that is endogenously presented has been altered can exhibit salt stress resistance and thus can grow in a medium with a salt concentration of 300 mM, preferably 250 mM, more preferably 200 mM, and most preferably 150 mM.

According to the present invention, the production of biomass by plants is increased. Hence, improvement in productivity can be achieved in both of the following cases: a case in which a purpose is to produce the whole plant; and a case in which a purpose is to produce some plant tissues (e.g., seeds) or components contained in plants. For example, when a purpose is to produce fats and oils contained in plant seeds, the amounts of fats and oils that can be harvested per area under cultivation can be greatly improved. Here, examples of fats and oils include, but are not particularly limited to, plant-derived fats and oils such as soybean oil, sesame oil, olive oil, coconut oil, rice oil, cottonseed oil, sunflower oil, corn oil, safflower oil, and rapeseed oil. Also, the thus produced fats and oils can be broadly used for household uses or industrial uses and can be further used as raw materials for biodiesel fuel. Hence, according to the present invention, the above fats and oils for household uses or industrial uses, biodiesel fuel, and the like can be produced at low cost with the use of plants into which the above CC-NBS-LRR gene has been introduced or in which an expression control region of the gene that is endogenously presented has been altered.

Further, according to the present invention, salt stress resistance of a plant is improved, allowing growth of the plant in soil with a high salt concentration that would not permit a wild-type plant to grow. An example of soil with a high salt concentration is soil collected in a coastal area. The use of such soil allows planting in soil that has been considered unavailable for planting. Accordingly, high production of a plant can be realized with the exhibition of the above effects of increasing biomass production. Further, also in a case in which a product of interest is fat and/or oil contained in plant seeds, high production can be achieved with the use of soil with a high salt concentration. In addition, the above fats and oils used for household and industrial applications, biodiesel fuel, and the like can be produced at low cost.

EXAMPLES

The present invention is hereafter described in greater detail with reference to the following examples, although the technical scope of the present invention is not limited thereto.

Example 1

1. Materials and Methods
1-1. Experimental Materials

As experimental materials, seeds of *Arabidopsis thaliana* mutants (Activation-tag lines: Weigel T-DNA lines, Total of 20072 lines) were used. In addition, the seeds were purchased from the Nottingham *Arabidopsis* Stock Centre (NASC). Regarding the seeds used as experimental materials, experimental materials, Weigel, D., et al., Plant Physiol., 122, 1003-1013 (2000) can be referred to.

1-2. Methods
1-2-1. Selection of Salt-Resistant Mutants

Seeds of Weigel T-DNA lines were aseptically sowed on 125 mM or 150 mM NaCl-containing modified MS agar (1%) medium [vitamins in B5 medium, 10 g/l sucrose, and 8 g/L agar (for bacterial medium; Wako Pure Chemical Industries, Ltd.)] and then cultured at 22° C. under 30-100 µmol/m$^2$/sec illumination (a cycle of 16 hours in the light/8 hours in the dark). Two to four weeks after sowing, salt-resistant mutant candidates were selected. In addition, regarding MS medium, see Murashige, T. et al. (1962) Physiol. Plant., 15, 473-497. Also, regarding the B5 medium, see Gamborg, O. L. et al. (1968) Experimental Cell Research, 50, 151-158.

1-2-2. DNA Preparation

A site for insertion of T-DNA into the genome of the thus selected salt-resistant *Arabidopsis thaliana* line was determined by a TAIL-PCR method. First, young leaves were harvested from the cultivated *Arabidopsis thaliana* plants and then crushed under liquid nitrogen freezing. DNA was prepared using a DNA preparation kit (DNeasy Plant Mini Kit, QIAGEN) according to the standard protocols included with the kit.

1-2-3. TAIL-PCR Method and Presumption of T-DNA Insertion Site

Three types of specific primers, TL1, TL2, and TL3, were determined to be located near the left T-DNA sequence (T-DNA left border) of an activation-tagging vector (pSKI015: GenBank accession No. AF187951) used in Weigel T-DNA lines. With the use of an arbitrary primer P1 and the following PCR reaction solutions and reaction conditions, TAIL-PCR (supervisors, Isao Shimamoto and Takuji Sasaki, New Edition, Plant PCR Experimental Protocols, 2000, pp. 83-89, Shujunsha, Tokyo, Japan; Genomics 25, 674-681, 1995; Plant J., 8, 457-463, 1995) was performed, so that genomic DNA adjacent to T-DNA was amplified.

The specific sequences of the primers TL1, TL2, TL3, and P1 are as follows.

```
                                            (SEQ ID NO: 6)
TL1:    5'-TGC TTT CGC CAT TAA ATA GCG ACG G-3'

(SEQ ID NO: 7)
TL2:    5'-CGC TGC GGA CAT CTA CAT TTT TG-3'

(SEQ ID NO: 8)
TL3:    5'-TCC GGA ACA TGA AGC CAT TTA C-3'

(SEQ ID NO: 9)
P1:     5'-NGT CGA SWG ANA WGA A-3'
```

In addition, in SEQ ID NO: 9, "n" represents "a," "g," "c," or "t" (location: 1 and 11), "s" represents "g" or "c" (location: 7), and "w" represents "a" or "t" (location: 8 and 13).

The 1$^{st}$ PCR reaction solution composition and reaction conditions are shown in Table 1 and Table 2, respectively.

TABLE 1

| | |
|---|---|
| Template (genomic DNA) | 10 ng |
| 10 × PCR buffer (Takara Bio) | 2 µl |
| 2.5 mM dNTPs (Takara Bio) | 1.6 µl |
| 1$^{st}$ specific primer (TL1: SEQ ID NO: 6) | 0.5 pmol |
| Arbitrary primer P1 (SEQ ID NO: 9) | 100 pmol |
| TaKaRa Ex Taq (Takara Bio) | 1.0 unit |
| Total volume | 20 µl |

TABLE 2

| | |
|---|---|
| #1: | 94° C. (30 seconds)/95° C. (30 seconds) |
| #2: | 5 cycles of 94° C. (30 seconds)/65° C. (30 seconds)/72° C. (1 minute) |
| #3: | 1 cycle of 94° C. (30 seconds)/25° C. (1 minute)→raised to 72° C. within 3 minutes/72° C. (3 minutes) |
| #4: | 94° C. (15 seconds)/65° C. (30 seconds)/72° C. (1 minute), 94° C. (15 seconds)/68° C. (30 seconds)/72° C. (1 minute), and 15 cycles of 94° C. (15 seconds)/44° C. (30 seconds)/72° C. (1 minute) |
| #5: | 72° C. (3 minutes) |

The 2$^{nd}$ PCR reaction solution composition and reaction conditions are shown in Table 3 and Table 4, respectively.

TABLE 3

| | |
|---|---|
| Template (50-fold dilution of the 1$^{st}$ PCR product) | 1 µl |
| 10 × PCR buffer (Takara Bio) | 2 µl |
| 2.5 mM dNTPs (Takara Bio) | 1.5 µl |
| 2$^{nd}$ specific primer (TL2: SEQ ID NO: 7) | 5 pmol |
| Arbitrary primer P1 (SEQ ID NO: 9) | 100 pmol |
| TaKaRa Ex Taq (Takara Bio) | 0.8 unit |
| Total volume | 20 µl |

TABLE 4

| | |
|---|---|
| #6: | 94° C. (15 seconds)/64° C. (30 seconds)/72° C. (1 minute), 94° C. (15 seconds)/64° C. (30 seconds)/72° C. (1 minute), and 12 cycles of 94° C. (15 seconds)/44° C. (30 seconds)/72° C. (1 minute) |
| #5: | 72° C. (5 minutes) |

The 3$^{rd}$ PCR reaction solution composition and reaction conditions are shown in Table 5 and Table 6, respectively.

TABLE 5

| | |
|---|---|
| Template (50-fold dilution of the 2$^{nd}$ PCR product) | 1 µl |
| 10 × PCR buffer (Takara Bio) | 5 µl |
| 2.5 mM dNTPs (Takara Bio) | 0.5 µl |
| 3$^{rd}$ specific primer (TL3: SEQ ID NO: 8) | 10 pmol |
| Arbitrary primer P1 (SEQ ID NO: 9) | 100 pmol |
| TaKaRa Ex Taq (Takara Bio) | 1.5 unit |
| Total volume | 50 µl |

TABLE 6

| | |
|---|---|
| #7: | 20 cycles of 94° C. (30 seconds)/44° C. (30 seconds)/72° C. (1 minute) |
| #5: | 72° C. (3 minutes) |

Subsequently, the 2$^{nd}$ and the 3$^{rd}$ reaction products were subjected to agarose gel electrophoresis and then the presence or the absence of amplification and the specificity of reaction products were confirmed. Also, the 3$^{rd}$ amplification products were subjected to a sequencing reaction directly using a Big-Dye Terminator Cycle Sequencing Kit Ver. 3. 1 (Applied Biosystems) and the specific primer TL3. Thus, nucleotide sequences were determined using an ABI PRISM 3100 Genetic Analyzer (Applied Biosystems).

As a result, 5 different nucleotide sequences were determined. Specifically, the 538-bp sequence information, the 311-bp sequence information, the 498-bp sequence information, the 633-bp sequence information, and the 448-bp sequence information were obtained. The obtained sequences are shown in SEQ ID NOS: 10 to 14.

The *Arabidopsis* Information Resource (on the web at TAIR: arabidopsis.org) was subjected to a BLAST search with the use of the obtained sequence information. Thus, the T-DNA insertion sites were found to exist in the following order: a site between the *Arabidopsis* chromosome 1 gene [AGI (The *Arabidopsis* Genome Initiative gene code) code: At1g69990] and the gene [AGI (The *Arabidopsis* Genome Initiative gene code) code: At1g70000]; a site of the *Arabidopsis* chromosome 5 gene [AGI (The *Arabidopsis* Genome Initiative gene code) code: At5g39400]; a site of the *Arabidopsis* chromosome 3 gene [AGI (The *Arabidopsis* Genome Initiative gene code) code: At3g05630]; a site of the *Arabidopsis* chromosome 2 gene [AGI (The *Arabidopsis* Genome Initiative gene code) code: At2g33110]; and a site of the *Arabidopsis* chromosome 1 gene [AGI (The *Arabidopsis* Genome Initiative gene code) code: At1g58520].

1-2-4. Prediction of Activated Genes

Activated genes were predicted based on the sequences of presumed open reading frame (ORF) genes existing within 10-Kb ranges near the respective T-DNA insertion sites (the site between At1g69990 and At1g70000, the site of At5g39400, the site of At3g05630, the site of At2g33110, and the site of At1g58520) revealed in 1-2-3 above.

1-2-5. Preparation of mutants via introduction of predicted genes

For amplification of fragments containing the ORF regions of the LRR-RLK (leucine-rich repeat receptor-like protein kinase) gene (AT1G69990), the LRR-RLK (leucine-rich repeat receptor-like protein kinase) gene (AT5G39390), the LRR (leucine-rich repeat) protein gene (AT3G05650), and the LRR (leucine-rich repeat) protein gene (AT2G33080) that had been predicted to be activated in 1-2-4, a pair of PCR primers were designed and synthesized for each fragment based on the sequence information disclosed at the TAIR (on the web at *arabidopsis*.org/home) (table 7). In addition, each pair of primers was designed so that a restriction enzyme site required for introduction into expression vectors was added to each primer (table 7).

TABLE 7

| Gene | Forward | Reverse | Restriction enzyme site | |
|---|---|---|---|---|
| AT1G69990 | 5'-ACG CGT CGA CCC ATC ATG AAA ACG ATC TCA ATC TTC TTC GTC-3' (SEQ ID NO: 15) | 5'-TGT ACA TGT ACA AGT GAG AAC GGT AGA TAA GTA AGT GG-3' (SEQ ID NO: 16) | Sal I | BsrG I |
| AT5G39390 | 5'-ACG CGT CGA CCA AAC GAC GTA TCT CAT AAG TCG ACG CA-3' (SEQ ID NO: 17) | 5'-TGT ACA TGT ACA GGA GAA CTT TGA AGA TCA TCG AGA GG-3' (SEQ ID NO: 18) | Sal I | BsrG I |
| AT3G05650 | 5'-ACG CGT CGA CCC ATC ACA CAC ACA TAC ACA CAC-3' (SEQ ID NO: 19) | 5'-TGT ACA TGT ACA CAG CGT AAA TGA AGA ACA CCC CAA ACT GAA C-3' (SEQ ID NO: 20) | Sal I | BsrG I |
| AT2G33080 | 5'-ACG CGT CGA CAT GTC AGG ATC ACA TCT GCG TTT GC-3' (SEQ ID NO: 21) | 5'-TGT ACA TGT ACA TCA GCA CTT GCT CCT GTT CTT CG-3' (SEQ ID NO: 22) | Sal I | BsrG I |

In order to amplify a fragment containing the ORF region of the CC (coiled-coil)-NBS (nucleotide binding site)-LRR (leucine-rich repeat) protein gene (AT1G58602), three pairs of primers were designed and synthesized based on the sequence information disclosed in TAR (on the web at arabidopsis.org/home) (table 8). Here, among the three sets of primers, the primers (Forward 1 and Reverse 3) were designed so that a restriction enzyme site required for introduction into expression vectors was added to each primer (table 8).

TABLE 8

| Gene | Forward | Reverse | Restriction enzyme site |
|---|---|---|---|
| AT1G58602 | Forward 1<br>5'-ACG CGT CGA CAT GGC AGG GGA ACT TGT GTC GTT TGC-3'<br>(SEQ ID NO: 23) | Reverse 1<br>5'-CCT TCT TCC ATA TGT CGT CGA GG-3'<br>(SEQ ID NO: 24) | Sal I |
| | Forward 2<br>5'-CCT CGA CGA CAT ATG GAA GAA GG-3'<br>(SEQ ID NO: 25) | Reverse 2<br>5'-CCA TAT TCC TCC TCA CCA GCT CCT CTA TG-3'<br>(SEQ ID NO: 26) | |
| | Forward 3<br>5'-CAT AGA GGA GCT GGT GAG GAG GAA TAT GG-3'<br>(SEQ ID NO: 27) | Reverse 3<br>5'-AAG GAA AAA AGC GGC CGC CTC TGT GAT TGC TGA GAG CAT TCC TAG TCG TCG-3'<br>(SEQ ID NO: 28) | Not I |

According to the method described in 1-2-2, a template DNA was prepared from wild-type *Arabidopsis thaliana* (eco-type Col-0). Takara Ex Taq (Takara Bio Inc.) and Platinum Pfx DNA Polymerase (Invitrogen) or Phusion High-Fidelity DNA Polymerase (New England BioLabs: NEB) were used as enzymes and a pair of primers listed in table 7 were used as primers. For the PCR reaction solution composition and reaction conditions, the protocols attached to each enzyme were referred to. In addition, for the CC-NBS-LRR protein gene (AT1G58602), PCR was performed using the three pairs of primers listed in table 8 and Platinum Pfx DNA Polymerase (Invitrogen) as an enzyme such that the three pairs of PCR amplification products were obtained. PCR amplification products were subjected to electrophoresis with 2% agarose gel (TAE buffer) and then fragments were stained with ethidium bromide. A gel containing target fragments was excised using a scalpel. Target DNA fragments were eluted and purified using GFX PCR DNA and a GEL Band Purification Kit (Amersham). Overlapping PCR was conducted with the use of the three DNA fragments as templates and Forward 1 and Reverse 3 as primers.

As in the above case, each PCR amplification product was subjected to agarose gel electrophoresis, followed by excision and purification. Adenin was added to the thus obtained DNA fragment using an A-Addition Kit (QIAGEN). The amplified DNA to which adenine had been added was ligated to a TA-Cloning pCR2.1 vector using a TOPO TA Cloning Kit (Invitrogen) and then transformed into competent cells (*E. coli* TOP 10) included with the kit. After transformation, cells were cultured in LB medium supplemented with 50 μl/ml kanamycin and then transformants were selected. Colonies that had appeared were subjected to liquid culture in LB medium supplemented with 50 μl/ml kanamycin. Plasmid DNA was prepared from the thus obtained microorganisms using a Plasmid Mini Kit (QIAGEN).

A fragment containing the ORF of the LRR-RLK gene (AT1G69990), a fragment containing the ORF of the LRR-RLK gene (AT5G39390), a fragment containing the ORF of the LRR protein gene (AT3G05650), a fragment containing the ORF of the LRR protein gene (AT2G33080), and a fragment containing the ORF of the CC-NBS-LRR protein gene (AT1G58602) were separately cloned into vectors, followed by determination of the nucleotide sequence and sequence analysis.

1-2-6. Construction of Plant Expression Vectors

Fragments containing ORFs of the LRR-RLK gene (AT1G69990), the LRR-RLK gene (AT5G39390), the LRR protein gene (AT3G05650), the LRR protein gene (AT2G33080), and the CC-NBS-LRR protein gene (AT1G58602) were inserted into a plant expression vector pBI121 containing an omega sequence from tobacco mosaic virus. Thus, constructs were prepared.

First, the pCR2.1 vector, in which a fragment containing ORF of the LRR-RLK gene (AT1G69990) had been cloned in 1-2-5, was treated with restriction enzymes Sal I and BsrG I.

Next, similarly pBI121 containing an omega sequence was treated with restriction enzymes Sal I and BsrG I. The products digested with these restriction enzymes were subjected to 0.8% agarose gel electrophoresis. A fragment of about 1850 bp containing ORF of the LRR-RLK gene (AT1G69990) and pBI121 containing the omega sequence were each fractioned and purified from the gel using GFX PCR DNA and a GEL Band Purification Kit (Amersham).

For introduction of a fragment containing ORF of the LRR-RLK gene (AT1G69990) using a pBI121 fragment containing the omega sequence as a vector, the vector and the insert were mixed at a ratio of 1:10, followed by an overnight ligation reaction at 16° C. using an equivalent amount of a TaKaRa Ligation Kit ver. 2 (Takara Bio Inc.).

The total amount of the reaction solution was added to 100 μl of competent cells (*E. coli* strain DH5α, TOYOBO), so that transformation was performed according to protocols included with the kit. Cells were applied to LB agar medium supplemented with 50 μg/ml kanamycin and then cultured overnight. Colonies that had appeared were subjected to liquid culture in LB medium supplemented with 50 μg/ml kanamycin. Plasmid DNA was prepared from the thus obtained microorganisms using a Plasmid Mini Kit (QIAGEN).

The thus obtained fragment containing ORF of the LRR-RLK gene (AT1G69990) was subcloned into an expression vector, followed by determination of the nucleotide sequence and sequence analysis.

The LRR-RLK gene (AT5G39390) and LRR protein gene (AT2G33080) were incorporated into expression vectors in the manner described above except that primers listed in table 7 were used, followed by nucleotide sequence determination and sequence analysis. The LRR protein gene (AT3G05650) was cloned into a TA-Cloning pCR2.1 vector, treated with an EcoR I restriction enzyme, and blunt-ended with a DNA Blunting Kit (Takara Bio Inc.), followed by treatment with phenol chloroform and then with a BsrG I restriction enzyme. pBI121 containing the omega sequence was treated with a Sal I restriction enzyme and blunt-ended with a DNA Blunting Kit (Takara Bio Inc.), followed by treatment with phenol chloroform and then with a BsrG I restriction enzyme. Each gene was incorporated into an expression vector in the manner described above, followed by nucleotide sequence determination and sequence analysis. The CC-NBS-LRR protein gene (AT1G58602) was treated with a Not I restriction enzyme and blunt-ended with a DNA Blunting Kit (Takara Bio Inc.), followed by treatment with phenol chloroform and then with a Sal I restriction enzyme. Similarly, pBI121 containing the omega sequence was treated with a BsrG I restriction enzyme and blunt-ended with a DNA Blunting Kit (Takara Bio Inc.), followed by treatment with phenol chloroform and then with a Sal I restriction enzyme. Each gene was incorporated into an expression vector in the manner described above, followed by nucleotide sequence determination and sequence analysis.

1-2-7. Gene Introduction into *Arabidopsis thaliana* Using *Agrobacterium* Method Each plant expression vector constructed in 1-2-6 was introduced into the *Agrobacterium tumefaciens* C58C1 strain by electroporation (Plant Molecular Biology Manual, Second Edition, B. G. Stanton, A. S. Robbert, Kluwer Acdemic Publishers, 1994). Subsequently, *Agrobacterium tumefaciens* into which the plant expression vector had been introduced was introduced into wild-type *Arabidopsis thaliana* (ecotype Col-0) by an infiltration method described by Clough et al. (Plant J., 16, 735-743, 1998).

Transformants were selected using kanamycin-containing medium. T2 generation plants were produced by self-pollination from the transformants.

1-2-8. Confirmation of the Phenotype of Transformant

Salt Resistance Test:

Seeds prepared in 1-2-7 and seeds of a non-recombinant wild-type plant (*Arabidopsis thaliana*) used as a control were aseptically sowed on an MS agar medium containing 150 mM NaCl. They were cultivated under conditions of 22° C. and 16 hours in the light/8 hours in the dark, and with a light intensity ranging from about 30 to 45 µE/cm² for 10 days, followed by salt resistance test.

Determination of the Amount of Biomass:

T2 seeds produced in 1-2-7 were aseptically sowed on an MS agar medium supplemented with 50 mg/L kanamycin and 0.5% sucrose and replanted in a pot with a diameter of 50 mm containing vermiculite mixed soil 2 weeks after sowing. As a control, seeds of a non-recombinant plant (*Arabidopsis thaliana*) were aseptically sowed on an MS agar medium supplemented with 0.5% sucrose and then replanted in the above manner. The resulting plants were cultivated under conditions of 23° C. and 8 hours in the light/16 hours in the dark (short-day conditions), and with a light intensity of approximately 160 µE/cm² for 6 weeks in total after replanting. After cultivation, aerial parts of the plants were placed in paper bag and dried at 22° C. at a humidity of 60% for 2 weeks. Then, the total amount of biomass was determined by an electronic scale.

2. Results

FIG. 2 is a photo of a plate for the wild-type plant and a photo of a plate for the transformed plant into which a fragment containing the ORF of the CC-NBS-LRR protein gene (AT1G58602) was introduced. The photographs indicate the results of the salt resistance test described in 1-2-8 above. FIG. 2 shows that the transformed plant into which a fragment containing the ORF of the CC-NBS-LRR protein gene (AT1G58602) had been introduced germinated and grew in a medium with a high salt concentration. The results revealed that the transformed plant exhibited improvement over the wild-type plant in terms of salt resistance.

In addition, FIG. 3 is a photo showing the aerial parts of wild-type plants and transformed plants into which a fragment containing the ORF of the CC-NBS-LRR protein gene (AT1G58602) was introduced. The photograph indicates the results of determination of the amount of biomass obtained in 1-2-8 above. Also, FIG. 4 shows results obtained by determining the total amount of biomass in the aerial parts of the wild type plant, the transformed plant into which the LRR-RLK protein gene (AT1G69990) was introduced, the transformed plant into which the LRR-RLK protein gene (AT5G39390) was introduced, the transformed plant into which the LRR protein gene (AT3G05650) was introduced, the transformed plant into which the LRR protein gene (AT2G33080) was introduced, and the transformed plant into which the CC-NBS-LRR protein gene (AT1G58602) was introduced.

FIGS. 3 and 4 revealed that, in the case of a transformed plant into which a fragment containing the ORF of the CC-NBS-LRR protein gene (AT1G58602) had been introduced, the total amount of biomass in the areial part was drastically improved to a greater extent (approximately 1.5 times greater) than that in the case of a wild-type plant. On the other hand, in the case of a transformed plant into which the LRR-RLK gene (AT1G69990), the LRR-RLK gene (AT5G39390), the LRR protein gene (AT3G05650), or the LRR protein gene (AT2G33080) had been introduced, the amount of biomass was found to be substantially comparable to that in the case of a wild-type plant.

The above results revealed that a plant into which the AT1G58602 gene has been introduced exhibits salt stress resistance and a significantly improved amount of biomass.

All publications, patents, and patent applications cited herein are incorporated herein by reference in their entirety.

The invention claimed is:

1. A plant, transformed with an expression construct comprising a promoter operably linked to a nucleotide sequence encoding SEQ ID NO: 5,
wherein said transformed plant has increased biomass and/or increased salt resistance as compared to a plant not transformed with said expression construct.

2. The plant according to claim 1, wherein SEQ ID NO: 5 is encoded by a polynucleotide hybridizing under stringent conditions to a polynucleotide comprising a nucleotide sequence complementary to the nucleotide sequence shown in SEQ ID NO: 4 and has a coiled-coil structure, a nucleic acid binding site, and a leucine rich repeat structure, wherein said stringent conditions are hybridization at about 45° C. with about 6×sodium chloride/sodium citrate (SSC), washing at about 50° C. to 65° C. with 0.2-1×SSC and about 0.1% SDS.

3. A method for increasing the production of biomass and imparting salt stress resistance to a plant,
comprising (i) generating an expression construct comprising a promoter operably linked to a polynucleotide that encodes SEQ ID NO: 5, (ii) introducing said expression construct into a plant, and (iii) growing said plant under conditions such that SEQ ID NO: 5 is expressed.

4. The method according to claim 3, wherein SEQ ID NO: 5 is encoded by a polynucleotide hybridizing under stringent conditions to a polynucleotide comprising a nucleotide sequence complementary to the nucleotide sequence shown in SEQ ID NO: 4 and has a coiled-coil structure, a nucleic acid binding site, and a leucine rich repeat structure, wherein said stringent conditions are hybridization at about 45° C. with about 6×sodium chloride/sodium citrate (SSC), washing at about 50° C. to 65° C. with 0.2-1×SSC and about 0.1% SDS.

5. A plant production method, comprising (i) transforming a plant with an expression construct comprising a promoter operably linked to a polynucleotide sequence encoding SEQ ID NO: 5, (ii) growing said transformed plant, (iii) determining the amount of biomass and salt stress resistance of a progeny plant of the transformed plant, wherein said progeny plant comprises said expression construct, and (iv) selecting a line that exhibits an improved amount of biomass and salt stress resistance in comparison to a plant not comprising said expression construct.

6. The production method according to claim 5, wherein SEQ ID NO: 5 is encoded by a polynucleotide hybridizing under stringent conditions to a polynucleotide comprising a nucleotide sequence complementary to the nucleotide sequence shown in SEQ ID NO: 4 and has a coiled-coil structure, a nucleic acid binding site, and a leucine rich repeat structure, wherein said stringent conditions are hybridization at about 45° C. with about 6×sodium chloride/sodium citrate (SSC), washing at about 50° C. to 65° C. with 0.2-1×SSC and about 0.1% SDS.

* * * * *

SEQUENCE LISTING

```
<160> NUMBER OF SEQ ID NOS: 43

<210> SEQ ID NO 1
<211> LENGTH: 22
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid,
      or preferably I, L or V
<220> FEATURE:
<221> NAME/KEY: misc_feature
<222> LOCATION: (4)..(4)
```

```
<223> OTHER INFORMATION: Xaa can be any naturally occurring amino acid,
      or preferably T, S or A
<220> FEATURE:
<221> NAME/KEY: misc_feature
<222> LOCATION: (6)..(6)
<223> OTHER INFORMATION: Xaa can be any naturally occurring amino acid,
      or preferably M or L
<220> FEATURE:
<221> NAME/KEY: misc_feature
<222> LOCATION: (9)..(9)
<223> OTHER INFORMATION: Xaa can be any naturally occurring amino acid,
      or preferably L or I
<220> FEATURE:
<221> NAME/KEY: misc_feature
<222> LOCATION: (16)..(16)
<223> OTHER INFORMATION: Xaa can be any naturally occurring amino acid,
      or preferably K or R
<220> FEATURE:
<221> NAME/KEY: misc_feature
<222> LOCATION: (18)..(18)
<223> OTHER INFORMATION: Xaa can be any naturally occurring amino acid,
      or preferably V or I
<220> FEATURE:
<221> NAME/KEY: misc_feature
<222> LOCATION: (20)..(20)
<223> OTHER INFORMATION: Xaa can be any naturally occurring amino acid,
      or preferably N, D or H
<220> FEATURE:
<221> NAME/KEY: misc_feature
<222> LOCATION: (22)..(22)
<223> OTHER INFORMATION: Xaa can be any naturally occurring amino acid,
      or preferably E or D

<400> SEQUENCE: 1

Val Ser Xaa Xaa Gly Xaa Gly Gly Xaa Gly Lys Thr Thr Leu Ala Xaa
1               5                   10                  15

Gln Xaa Phe Xaa His Xaa
            20

<210> SEQ ID NO 2
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid,
      or preferably H, R or Q
<220> FEATURE:
<221> NAME/KEY: misc_feature
<222> LOCATION: (3)..(3)
<223> OTHER INFORMATION: Xaa can be any naturally occurring amino acid,
      or preferably L or M
<220> FEATURE:
<221> NAME/KEY: misc_feature
<222> LOCATION: (6)..(6)
<223> OTHER INFORMATION: Xaa can be any naturally occurring amino acid,
      or preferably M, I or L
<220> FEATURE:
<221> NAME/KEY: misc_feature
<222> LOCATION: (7)..(7)
<223> OTHER INFORMATION: Xaa can be any naturally occurring amino acid,
      or preferably M or V
<220> FEATURE:
<221> NAME/KEY: misc_feature
<222> LOCATION: (10)..(10)
<223> OTHER INFORMATION: Xaa can be any naturally occurring amino acid,
      or preferably V or I
<220> FEATURE:
<221> NAME/KEY: misc_feature
<222> LOCATION: (12)..(12)
<223> OTHER INFORMATION: Xaa can be any naturally occurring amino acid,
      or preferably L or I
```

<400> SEQUENCE: 2

Cys Xaa Xaa His Asp Xaa Xaa Arg Glu Xaa Cys Xaa
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid,
      or preferably I or L
<220> FEATURE:
<221> NAME/KEY: misc_feature
<222> LOCATION: (6)..(6)
<223> OTHER INFORMATION: Xaa can be any naturally occurring amino acid,
      or preferably V or A
<220> FEATURE:
<221> NAME/KEY: misc_feature
<222> LOCATION: (7)..(7)
<223> OTHER INFORMATION: Xaa can be any naturally occurring amino acid,
      or preferably R or K
<220> FEATURE:
<221> NAME/KEY: misc_feature
<222> LOCATION: (10)..(10)
<223> OTHER INFORMATION: Xaa can be any naturally occurring amino acid,
      or preferably M or L
<220> FEATURE:
<221> NAME/KEY: misc_feature
<222> LOCATION: (11)..(11)
<223> OTHER INFORMATION: Xaa can be any naturally occurring amino acid,
      or preferably V or I

<400> SEQUENCE: 3

Tyr Xaa Glu Glu Leu Xaa Xaa Arg Asn Xaa Xaa
1               5                   10

<210> SEQ ID NO 4
<211> LENGTH: 3417
<212> TYPE: DNA
<213> ORGANISM: Arabidopsis thaliana
<220> FEATURE:
<221> NAME/KEY: CDS
<222> LOCATION: (1)..(3417)

<400> SEQUENCE: 4

```
atg gca ggg gaa ctt gtg tcg ttt gca gta aac aag ctt tgg gac cta      48
Met Ala Gly Glu Leu Val Ser Phe Ala Val Asn Lys Leu Trp Asp Leu
1               5                   10                  15 ctg agc cat gaa tac acg cta ttt cag gga gtc gaa gat caa gta gct      96
Leu Ser His Glu Tyr Thr Leu Phe Gln Gly Val Glu Asp Gln Val Ala
            20                  25                  30 gaa cta aaa agt gat cta aac ttg cta aag tcg ttt ttg aaa gat gca     144
Glu Leu Lys Ser Asp Leu Asn Leu Leu Lys Ser Phe Leu Lys Asp Ala
        35                  40                  45 gat gcc aag aaa cac aca agc gca ttg gtg aga tac tgt gtg gag gag     192
Asp Ala Lys Lys His Thr Ser Ala Leu Val Arg Tyr Cys Val Glu Glu
    50                  55                  60 ata aag gat att gtt tat gac gca gag gat gta ctc gaa aca ttt gta     240
Ile Lys Asp Ile Val Tyr Asp Ala Glu Asp Val Leu Glu Thr Phe Val
65                  70                  75                  80 caa aag gaa aag ctt ggt aca aca agt gga atc agg aag cat atc aaa     288
Gln Lys Glu Lys Leu Gly Thr Thr Ser Gly Ile Arg Lys His Ile Lys
                85                  90                  95 aga ctt act tgc att gtt cca gat cgc agg gaa att gca tta tat atc     336
```

```
Arg Leu Thr Cys Ile Val Pro Asp Arg Arg Glu Ile Ala Leu Tyr Ile
            100                 105                 110 gga cac gta agt aag agg atc acc agg gtt ata cgt gat atg cag agt      384
Gly His Val Ser Lys Arg Ile Thr Arg Val Ile Arg Asp Met Gln Ser
        115                 120                 125 ttt gga gta caa caa atg att gtc gat gac tat atg cat cct cta cgt      432
Phe Gly Val Gln Gln Met Ile Val Asp Asp Tyr Met His Pro Leu Arg
130                 135                 140 aat aga gaa agg gag ata cga cga aca ttt cct aag gac aat gaa agt      480
Asn Arg Glu Arg Glu Ile Arg Arg Thr Phe Pro Lys Asp Asn Glu Ser
145                 150                 155                 160 ggt ttt gtg gcg ttg gag gaa aat gtt aaa aag tta gtt gga tat ttt      528
Gly Phe Val Ala Leu Glu Glu Asn Val Lys Lys Leu Val Gly Tyr Phe
                165                 170                 175 gtg gag gaa gat aac tat caa gtg gtt tcc ata act gga atg ggt ggt      576
Val Glu Glu Asp Asn Tyr Gln Val Val Ser Ile Thr Gly Met Gly Gly
            180                 185                 190 ctc ggt aaa acc acc ctt gct aga caa gtt ttt aac cac gat atg gtt      624
Leu Gly Lys Thr Thr Leu Ala Arg Gln Val Phe Asn His Asp Met Val
        195                 200                 205 aca aag aag ttt gat aaa cta gca tgg gtg agt gtt tca caa gat ttt      672
Thr Lys Lys Phe Asp Lys Leu Ala Trp Val Ser Val Ser Gln Asp Phe
210                 215                 220 acc ctg aag aat gta tgg caa aat att ttg ggg gat ctc aaa ccc aaa      720
Thr Leu Lys Asn Val Trp Gln Asn Ile Leu Gly Asp Leu Lys Pro Lys
225                 230                 235                 240 gaa gaa gaa acc aaa gaa gaa gaa aag aaa atc ttg gag atg aca gaa      768
Glu Glu Glu Thr Lys Glu Glu Glu Lys Lys Ile Leu Glu Met Thr Glu
                245                 250                 255 tat aca ctc caa cgt gaa cta tat caa ttg ttg gaa atg tct aag tcg      816
Tyr Thr Leu Gln Arg Glu Leu Tyr Gln Leu Leu Glu Met Ser Lys Ser
            260                 265                 270 tta att gtc ctc gac gac ata tgg aag aag gaa gat tgg gaa gta atc      864
Leu Ile Val Leu Asp Asp Ile Trp Lys Lys Glu Asp Trp Glu Val Ile
        275                 280                 285 aag cca ata ttt cca ccg aca aaa ggt tgg aaa ctg ctg ctt act tct      912
Lys Pro Ile Phe Pro Pro Thr Lys Gly Trp Lys Leu Leu Leu Thr Ser
290                 295                 300 cga aat gag agt atc gtt gcg cct aca aat aca aaa tat ttc aac ttt      960
Arg Asn Glu Ser Ile Val Ala Pro Thr Asn Thr Lys Tyr Phe Asn Phe
305                 310                 315                 320 aaa cca gaa tgc cta aag act gat gac agt tgg aaa ctt ttt caa agg     1008
Lys Pro Glu Cys Leu Lys Thr Asp Asp Ser Trp Lys Leu Phe Gln Arg
                325                 330                 335 ata gca ttt cct ata aat gat gca tct gaa ttt gag att gat gag gaa     1056
Ile Ala Phe Pro Ile Asn Asp Ala Ser Glu Phe Glu Ile Asp Glu Glu
            340                 345                 350 atg gaa aag ttg ggt gag aaa atg atc gaa cat tgt gga ggg cta cca     1104
Met Glu Lys Leu Gly Glu Lys Met Ile Glu His Cys Gly Gly Leu Pro
        355                 360                 365 ttg gct atc aaa gtg tta gga ggt atg tta gct gaa aaa tac aca tcg     1152
Leu Ala Ile Lys Val Leu Gly Gly Met Leu Ala Glu Lys Tyr Thr Ser
370                 375                 380 cat gat tgg aga aga tta tct gag aat att gga tct cat ctc gtg gga     1200
His Asp Trp Arg Arg Leu Ser Glu Asn Ile Gly Ser His Leu Val Gly
385                 390                 395                 400 gga aga act aac ttt aat gac gac aac aac aat tca tgt aac tat gta     1248
Gly Arg Thr Asn Phe Asn Asp Asp Asn Asn Asn Ser Cys Asn Tyr Val
                405                 410                 415
```

```
                                              -continued ttg tct ttg agc ttt gaa gaa ttg cca agt tat ttg aag cat tgt ttc    1296
Leu Ser Leu Ser Phe Glu Glu Leu Pro Ser Tyr Leu Lys His Cys Phe
        420                 425                 430 ctc tac ttg gcc cat ttt cca gaa gat tat gag ata aag gta gag aat    1344
Leu Tyr Leu Ala His Phe Pro Glu Asp Tyr Glu Ile Lys Val Glu Asn
            435                 440                 445 ttg tca tat tac tgg gct gca gaa gaa ata ttc caa cct agg cat tac    1392
Leu Ser Tyr Tyr Trp Ala Ala Glu Glu Ile Phe Gln Pro Arg His Tyr
    450                 455                 460 gat gga gaa atc att cga gat gtt gga gat gtc tac ata gag gag ctg    1440
Asp Gly Glu Ile Ile Arg Asp Val Gly Asp Val Tyr Ile Glu Glu Leu
465                 470                 475                 480 gtg agg agg aat atg gtc att tcc gaa aga gat gta aag act tcg aga    1488
Val Arg Arg Asn Met Val Ile Ser Glu Arg Asp Val Lys Thr Ser Arg
                485                 490                 495 ttt gaa act tgt cat ttg cat gac atg atg aga gaa gtt tgt ttg tta    1536
Phe Glu Thr Cys His Leu His Asp Met Met Arg Glu Val Cys Leu Leu
            500                 505                 510 aaa gct aaa gaa gaa aac ttc cta caa att acc agt aac ccc cct tca    1584
Lys Ala Lys Glu Glu Asn Phe Leu Gln Ile Thr Ser Asn Pro Pro Ser
    515                 520                 525 act gca aat ttt cag tct act gtc aca tct cgc agg ctt gtc tac caa    1632
Thr Ala Asn Phe Gln Ser Thr Val Thr Ser Arg Arg Leu Val Tyr Gln
530                 535                 540 tat cct act act tta cat gtt gag aaa gat ata aac aat cca aaa ctt    1680
Tyr Pro Thr Thr Leu His Val Glu Lys Asp Ile Asn Asn Pro Lys Leu
545                 550                 555                 560 cga tct ctc gtg gtt gtt acc ttg gga agt tgg aac atg gca ggt tca    1728
Arg Ser Leu Val Val Val Thr Leu Gly Ser Trp Asn Met Ala Gly Ser
                565                 570                 575 agc ttt aca agg tta gaa ctt cta agg gtg tta gat ctc gtt caa gcc    1776
Ser Phe Thr Arg Leu Glu Leu Leu Arg Val Leu Asp Leu Val Gln Ala
            580                 585                 590 aag ttg aaa gga ggg aag tta gct tct tgc att gga aag ctc atc cac    1824
Lys Leu Lys Gly Gly Lys Leu Ala Ser Cys Ile Gly Lys Leu Ile His
    595                 600                 605 tta aga tac ttg agc tta gag tat gca gag gta act cat ata cct tac    1872
Leu Arg Tyr Leu Ser Leu Glu Tyr Ala Glu Val Thr His Ile Pro Tyr
610                 615                 620 tca cta gga aat ctg aag ttg ttg atc tat ctg aat tta cat atc tca    1920
Ser Leu Gly Asn Leu Lys Leu Leu Ile Tyr Leu Asn Leu His Ile Ser
625                 630                 635                 640 tta tca tca aga tcc aac ttt gtg ccc aat gtc ttg atg ggg atg caa    1968
Leu Ser Ser Arg Ser Asn Phe Val Pro Asn Val Leu Met Gly Met Gln
                645                 650                 655 gaa ctg aga tac ctt gcg tta cca agc ctt atc gag agg aag aca aaa    2016
Glu Leu Arg Tyr Leu Ala Leu Pro Ser Leu Ile Glu Arg Lys Thr Lys
            660                 665                 670 cta gaa ttg agt aat cta gta aaa ttg gag act tta gag aat ttc tca    2064
Leu Glu Leu Ser Asn Leu Val Lys Leu Glu Thr Leu Glu Asn Phe Ser
    675                 680                 685 aca aag aat agc agc ttg gag gat ctt cgt ggt atg gtc agg ctg aga    2112
Thr Lys Asn Ser Ser Leu Glu Asp Leu Arg Gly Met Val Arg Leu Arg
690                 695                 700 acg ctc acc atc gaa tta att gag gag acg agt tta gaa act cta gct    2160
Thr Leu Thr Ile Glu Leu Ile Glu Glu Thr Ser Leu Glu Thr Leu Ala
705                 710                 715                 720 gca tct ata ggt gga ttg aaa tac ctg gaa aaa ctt gaa ata gat gat    2208
Ala Ser Ile Gly Gly Leu Lys Tyr Leu Glu Lys Leu Glu Ile Asp Asp
                725                 730                 735
```

```
ctc ggt tct aag atg agg acg aag gaa gcg ggg atc gta ttt gat ttc      2256
Leu Gly Ser Lys Met Arg Thr Lys Glu Ala Gly Ile Val Phe Asp Phe
        740                 745                 750 gtt cat ctc aaa agg cta agg ttg gaa ctg tat atg cct agg ctt tct      2304
Val His Leu Lys Arg Leu Arg Leu Glu Leu Tyr Met Pro Arg Leu Ser
        755                 760                 765 aaa gaa caa cac ttc cct tct cac ctt aca acc tta tat cta caa cat      2352
Lys Glu Gln His Phe Pro Ser His Leu Thr Thr Leu Tyr Leu Gln His
770                 775                 780 tgt cgg ttg gaa gag gat ccc atg ccg att cta gag aag ttg cta cag      2400
Cys Arg Leu Glu Glu Asp Pro Met Pro Ile Leu Glu Lys Leu Leu Gln
785                 790                 795                 800 ttg aaa gag ctt gaa tta ggg cat aaa tct ttc agt gga aag aaa atg      2448
Leu Lys Glu Leu Glu Leu Gly His Lys Ser Phe Ser Gly Lys Lys Met
                805                 810                 815 gtt tgc tcg agc tgt ggg ttt cct caa ttg cag aag ctt tca ata agc      2496
Val Cys Ser Ser Cys Gly Phe Pro Gln Leu Gln Lys Leu Ser Ile Ser
            820                 825                 830 gga cta aag gaa tgg gaa gat tgg aaa gta gaa gaa agc tcc atg cca      2544
Gly Leu Lys Glu Trp Glu Asp Trp Lys Val Glu Glu Ser Ser Met Pro
        835                 840                 845 ctt ctt ctt act ctc aat atc ttt gat tgt cga aaa tta aag cag ctt      2592
Leu Leu Leu Thr Leu Asn Ile Phe Asp Cys Arg Lys Leu Lys Gln Leu
    850                 855                 860 cct gat gaa cac ctc cct tct cac ctt aca gcc ata tct cta aaa aag      2640
Pro Asp Glu His Leu Pro Ser His Leu Thr Ala Ile Ser Leu Lys Lys
865                 870                 875                 880 tgt ggg ttg gag gat cca atc cca act cta gag aga ttg gtt cac ttg      2688
Cys Gly Leu Glu Asp Pro Ile Pro Thr Leu Glu Arg Leu Val His Leu
                885                 890                 895 aaa gag cta tca tta tct gaa cta tgt ggg agg ata atg gtt tgc acg      2736
Lys Glu Leu Ser Leu Ser Glu Leu Cys Gly Arg Ile Met Val Cys Thr
            900                 905                 910 ggc ggt ggg ttt cct caa ttg cac aag cta gac tta tct gaa cta gat      2784
Gly Gly Gly Phe Pro Gln Leu His Lys Leu Asp Leu Ser Glu Leu Asp
        915                 920                 925 ggg ttg gaa gag tgg ata gtt gag gat ggc tcc atg cca cgg ctt cat      2832
Gly Leu Glu Glu Trp Ile Val Glu Asp Gly Ser Met Pro Arg Leu His
    930                 935                 940 act cta gaa att cgt agg tgt cta aag tta aag aag cta cct aat ggg      2880
Thr Leu Glu Ile Arg Arg Cys Leu Lys Leu Lys Lys Leu Pro Asn Gly
945                 950                 955                 960 ttt cca caa ttg cag aat ctt cac tta act gag gta gag gaa tgg gaa      2928
Phe Pro Gln Leu Gln Asn Leu His Leu Thr Glu Val Glu Glu Trp Glu
                965                 970                 975 gag ggg atg ata gta aaa caa ggc tcc atg ccc ctt ctt cat act ctc      2976
Glu Gly Met Ile Val Lys Gln Gly Ser Met Pro Leu Leu His Thr Leu
            980                 985                 990 tat atc tgg cat tgt cca aag ctt cct ggt gaa caa cac ttc cct tct      3024
Tyr Ile Trp His Cys Pro Lys Leu Pro Gly Glu Gln His Phe Pro Ser
        995                 1000                1005 cac ctt aca acc gta ttt cta ctc ggt atg tat gtg gag gag gat           3069
His Leu Thr Thr Val Phe Leu Leu Gly Met Tyr Val Glu Glu Asp
    1010                1015                1020 cca atg cgg att cta gag aag ctg ctt cac ttg aaa aat gtt tct           3114
Pro Met Arg Ile Leu Glu Lys Leu Leu His Leu Lys Asn Val Ser
1025                1030                1035 ttg ttt caa tct ttc agt ggg aag aga atg gtt tgc tcg ggc ggt           3159
Leu Phe Gln Ser Phe Ser Gly Lys Arg Met Val Cys Ser Gly Gly
```

```
                    1040              1045              1050
ggg  ttt  cct  caa  ttg  cag  aag  ctt  tca  ata  cgg  gaa  ata  gag  tgg      3204
Gly  Phe  Pro  Gln  Leu  Gln  Lys  Leu  Ser  Ile  Arg  Glu  Ile  Glu  Trp
1055                1060                    1065 gaa  gag  tgg  ata  gta  gaa  caa  ggc  tcc  atg  ccc  ctt  ctt  cat  act      3249
Glu  Glu  Trp  Ile  Val  Glu  Gln  Gly  Ser  Met  Pro  Leu  Leu  His  Thr
     1070                1075                    1080 ctc  tat  atc  ggg  gtt  tgt  cca  aac  tta  aag  gag  ctt  cct  gat  ggg      3294
Leu  Tyr  Ile  Gly  Val  Cys  Pro  Asn  Leu  Lys  Glu  Leu  Pro  Asp  Gly
1085                1090                    1095 ctg  cga  ttt  atc  tat  tca  tta  aaa  aat  ttg  ata  gta  tca  aaa  aga      3339
Leu  Arg  Phe  Ile  Tyr  Ser  Leu  Lys  Asn  Leu  Ile  Val  Ser  Lys  Arg
     1100                1105                    1110 tgg  aag  aag  aga  ttg  tcg  gaa  gga  gga  gaa  gat  tat  tac  aaa  gtc      3384
Trp  Lys  Lys  Arg  Leu  Ser  Glu  Gly  Gly  Glu  Asp  Tyr  Tyr  Lys  Val
1115                1120                    1125 caa  cac  att  cct  tct  gtt  gaa  ttc  gac  gac  tag                           3417
Gln  His  Ile  Pro  Ser  Val  Glu  Phe  Asp  Asp
     1130                1135

<210> SEQ ID NO 5
<211> LENGTH: 1138
<212> TYPE: PRT
<213> ORGANISM: Arabidopsis thaliana

<400> SEQUENCE: 5

Met Ala Gly Glu Leu Val Ser Phe Ala Val Asn Lys Leu Trp Asp Leu
1               5                   10                  15

Leu Ser His Glu Tyr Thr Leu Phe Gln Gly Val Glu Asp Gln Val Ala
            20                  25                  30

Glu Leu Lys Ser Asp Leu Asn Leu Leu Lys Ser Phe Leu Lys Asp Ala
        35                  40                  45

Asp Ala Lys Lys His Thr Ser Ala Leu Val Arg Tyr Cys Val Glu Glu
    50                  55                  60

Ile Lys Asp Ile Val Tyr Asp Ala Glu Asp Val Leu Glu Thr Phe Val
65              70                  75                  80

Gln Lys Glu Lys Leu Gly Thr Thr Ser Gly Ile Arg Lys His Ile Lys
                85                  90                  95

Arg Leu Thr Cys Ile Val Pro Asp Arg Arg Glu Ile Ala Leu Tyr Ile
            100                 105                 110

Gly His Val Ser Lys Arg Ile Thr Arg Val Ile Arg Asp Met Gln Ser
        115                 120                 125

Phe Gly Val Gln Gln Met Ile Val Asp Asp Tyr Met His Pro Leu Arg
    130                 135                 140

Asn Arg Glu Arg Glu Ile Arg Arg Thr Phe Pro Lys Asp Asn Glu Ser
145                 150                 155                 160

Gly Phe Val Ala Leu Glu Glu Asn Val Lys Lys Leu Val Gly Tyr Phe
                165                 170                 175

Val Glu Glu Asp Asn Tyr Gln Val Val Ser Ile Thr Gly Met Gly Gly
            180                 185                 190

Leu Gly Lys Thr Thr Leu Ala Arg Gln Val Phe Asn His Asp Met Val
        195                 200                 205

Thr Lys Lys Phe Asp Lys Leu Ala Trp Val Ser Val Ser Gln Asp Phe
    210                 215                 220

Thr Leu Lys Asn Val Trp Gln Asn Ile Leu Gly Asp Leu Lys Pro Lys
225                 230                 235                 240
```

```
Glu Glu Glu Thr Lys Glu Glu Lys Lys Ile Leu Glu Met Thr Glu
                245                 250                 255
Tyr Thr Leu Gln Arg Glu Leu Tyr Gln Leu Leu Glu Met Ser Lys Ser
            260                 265                 270
Leu Ile Val Leu Asp Asp Ile Trp Lys Lys Glu Asp Trp Glu Val Ile
        275                 280                 285
Lys Pro Ile Phe Pro Pro Thr Lys Gly Trp Lys Leu Leu Leu Thr Ser
    290                 295                 300
Arg Asn Glu Ser Ile Val Ala Pro Thr Asn Thr Lys Tyr Phe Asn Phe
305                 310                 315                 320
Lys Pro Glu Cys Leu Lys Thr Asp Asp Ser Trp Lys Leu Phe Gln Arg
                325                 330                 335
Ile Ala Phe Pro Ile Asn Asp Ala Ser Glu Phe Glu Ile Asp Glu Glu
            340                 345                 350
Met Glu Lys Leu Gly Glu Lys Met Ile Glu His Cys Gly Gly Leu Pro
        355                 360                 365
Leu Ala Ile Lys Val Leu Gly Gly Met Leu Ala Glu Lys Tyr Thr Ser
    370                 375                 380
His Asp Trp Arg Arg Leu Ser Glu Asn Ile Gly Ser His Leu Val Gly
385                 390                 395                 400
Gly Arg Thr Asn Phe Asn Asp Asp Asn Asn Ser Cys Asn Tyr Val
                405                 410                 415
Leu Ser Leu Ser Phe Glu Glu Leu Pro Ser Tyr Leu Lys His Cys Phe
            420                 425                 430
Leu Tyr Leu Ala His Phe Pro Glu Asp Tyr Glu Ile Lys Val Glu Asn
        435                 440                 445
Leu Ser Tyr Tyr Trp Ala Ala Glu Glu Ile Phe Gln Pro Arg His Tyr
    450                 455                 460
Asp Gly Glu Ile Ile Arg Asp Val Gly Asp Val Tyr Ile Glu Glu Leu
465                 470                 475                 480
Val Arg Arg Asn Met Val Ile Ser Glu Arg Asp Val Lys Thr Ser Arg
                485                 490                 495
Phe Glu Thr Cys His Leu His Asp Met Met Arg Glu Val Cys Leu Leu
            500                 505                 510
Lys Ala Lys Glu Glu Asn Phe Leu Gln Ile Thr Ser Asn Pro Pro Ser
        515                 520                 525
Thr Ala Asn Phe Gln Ser Thr Val Thr Ser Arg Arg Leu Val Tyr Gln
    530                 535                 540
Tyr Pro Thr Thr Leu His Val Glu Lys Asp Ile Asn Asn Pro Lys Leu
545                 550                 555                 560
Arg Ser Leu Val Val Thr Leu Gly Ser Trp Asn Met Ala Gly Ser
                565                 570                 575
Ser Phe Thr Arg Leu Glu Leu Leu Arg Val Leu Asp Leu Val Gln Ala
            580                 585                 590
Lys Leu Lys Gly Gly Lys Leu Ala Ser Cys Ile Gly Lys Leu Ile His
        595                 600                 605
Leu Arg Tyr Leu Ser Leu Glu Tyr Ala Glu Val Thr His Ile Pro Tyr
    610                 615                 620
Ser Leu Gly Asn Leu Lys Leu Leu Ile Tyr Leu Asn Leu His Ile Ser
625                 630                 635                 640
Leu Ser Ser Arg Ser Asn Phe Val Pro Asn Val Leu Met Gly Met Gln
                645                 650                 655
Glu Leu Arg Tyr Leu Ala Leu Pro Ser Leu Ile Glu Arg Lys Thr Lys
```

```
                    660             665             670
Leu Glu Leu Ser Asn Leu Val Lys Leu Glu Thr Leu Glu Asn Phe Ser
            675             680             685

Thr Lys Asn Ser Ser Leu Glu Asp Leu Arg Gly Met Val Arg Leu Arg
        690             695             700

Thr Leu Thr Ile Glu Leu Ile Glu Glu Thr Ser Leu Glu Thr Leu Ala
705             710             715             720

Ala Ser Ile Gly Gly Leu Lys Tyr Leu Glu Lys Leu Glu Ile Asp Asp
                725             730             735

Leu Gly Ser Lys Met Arg Thr Lys Glu Ala Gly Ile Val Phe Asp Phe
            740             745             750

Val His Leu Lys Arg Leu Arg Leu Glu Leu Tyr Met Pro Arg Leu Ser
        755             760             765

Lys Glu Gln His Phe Pro Ser His Leu Thr Thr Leu Tyr Leu Gln His
    770             775             780

Cys Arg Leu Glu Glu Asp Pro Met Pro Ile Leu Glu Lys Leu Leu Gln
785             790             795             800

Leu Lys Glu Leu Glu Leu Gly His Lys Ser Phe Ser Gly Lys Met
                805             810             815

Val Cys Ser Ser Cys Gly Phe Pro Gln Leu Gln Lys Leu Ser Ile Ser
            820             825             830

Gly Leu Lys Glu Trp Glu Asp Trp Lys Val Glu Glu Ser Ser Met Pro
        835             840             845

Leu Leu Leu Thr Leu Asn Ile Phe Asp Cys Arg Lys Leu Lys Gln Leu
    850             855             860

Pro Asp Glu His Leu Pro Ser His Leu Thr Ala Ile Ser Leu Lys Lys
865             870             875             880

Cys Gly Leu Glu Asp Pro Ile Pro Thr Leu Glu Arg Leu Val His Leu
                885             890             895

Lys Glu Leu Ser Leu Ser Glu Leu Cys Gly Arg Ile Met Val Cys Thr
            900             905             910

Gly Gly Gly Phe Pro Gln Leu His Lys Leu Asp Leu Ser Glu Leu Asp
        915             920             925

Gly Leu Glu Glu Trp Ile Val Glu Asp Gly Ser Met Pro Arg Leu His
    930             935             940

Thr Leu Glu Ile Arg Arg Cys Leu Lys Leu Lys Lys Leu Pro Asn Gly
945             950             955             960

Phe Pro Gln Leu Gln Asn Leu His Leu Thr Glu Val Glu Glu Trp Glu
                965             970             975

Glu Gly Met Ile Val Lys Gln Gly Ser Met Pro Leu Leu His Thr Leu
            980             985             990

Tyr Ile Trp His Cys Pro Lys Leu Pro Gly Glu Gln His Phe Pro Ser
        995             1000            1005

His Leu Thr Thr Val Phe Leu Leu Gly Met Tyr Val Glu Glu Asp
    1010            1015            1020

Pro Met Arg Ile Leu Glu Lys Leu Leu His Leu Lys Asn Val Ser
1025            1030            1035

Leu Phe Gln Ser Phe Ser Gly Lys Arg Met Val Cys Ser Gly Gly
    1040            1045            1050

Gly Phe Pro Gln Leu Gln Lys Leu Ser Ile Arg Glu Ile Glu Trp
    1055            1060            1065

Glu Glu Trp Ile Val Glu Gln Gly Ser Met Pro Leu Leu His Thr
    1070            1075            1080
```

Leu Tyr Ile Gly Val Cys Pro Asn Leu Lys Glu Leu Pro Asp Gly
    1085                1090                1095

Leu Arg Phe Ile Tyr Ser Leu Lys Asn Leu Ile Val Ser Lys Arg
    1100                1105                1110

Trp Lys Lys Arg Leu Ser Glu Gly Gly Glu Asp Tyr Tyr Lys Val
    1115                1120                1125

Gln His Ile Pro Ser Val Glu Phe Asp Asp
    1130                1135

```
<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 6
tgctttcgcc attaaatagc gacgg                                             25

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 7
cgctgcggac atctacattt ttg                                               23

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 8
tcccggacat gaagccattt ac                                                22

<210> SEQ ID NO 9
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 9
ngtcgaswga nawgaa                                                       16

<210> SEQ ID NO 10
<211> LENGTH: 538
<212> TYPE: DNA
<213> ORGANISM: Arabidopsis thaliana

<400> SEQUENCE: 10
cgatgcttgt ccatatccaa acatttcagc catttagtgc tctcactaaa catctttta       60
```

```
caaaatatga aataacattc ccaaaattgc gatcaaaagg ctagaaacat cttcaacaat    120
tatgacagtc ctaaaccaac agttcaaaca cgttttatat ctgtttggcc aaattaaacg    180
aatataacat aaaaatacga ttgatcttag acaattacta aagtttctaa ataataatct    240
atactttcac aaaacaagaa atacaaattg attcttgcgc agaaagtgct ttggtaccta    300 cttttttac caccttcct tttcaattga gacatcaaca cattcactaa aacaaactct      360
caaactgctc taaacgacac cgtttagtta cagataactt tacttgtatt taaagtcacc    420
aaaagtttga attttatt gtgccttcca caaagcttta agcttaaaca cagtcaatgg      480
ccgtccttcc gccataaaag gacaaaaaaa aagcttccct cttttcacaa acccctaa     538

<210> SEQ ID NO 11
<211> LENGTH: 311
<212> TYPE: DNA
<213> ORGANISM: Arabidopsis thaliana
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t

<400> SEQUENCE: 11
gaatcctgtc cgtctgttaa ccacatttta taatagttcc attatcgacg aaaaaacntg     60
tcttgattnc tactttgaca aacctgtgag agtaagtcac aaaacaaata ttcttcagac    120 aatgttttg ataagatttt gataagcata tgattcttgg acaggttagt ggtgacatac     180
gcatcacatt ctaccagaaa atgattggaa gccgcctttt ttatacttgc ttcaacacag    240
cttttataac caatggctta cttcaggtaa agaattctcc agatgcctca aactcattct    300
tctcactcga c                                                          311

<210> SEQ ID NO 12
<211> LENGTH: 498
<212> TYPE: DNA
<213> ORGANISM: Arabidopsis thaliana
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t

<400> SEQUENCE: 12
taaccttacg ctttgctcgg tcccagacgc aagattacat ctctttctat ggnttgagat     60
cgnacggacg gctgtttgag gacggtccaa ttgccactag ccagatttac gtgcatagca    120
agttaatgat tgttgatgac cggatcgcag tgatcggatc ttctaatata aacgatagga    180
gcttactagg ttcacgagac tctgaggtac tttcaaaaat ccaattcatt ctttattgca    240
gcaaaacaga gttatgtatt catttgaatc aatcatgttt cagatcggtg ttgtgattga    300
agacaaagaa ttcgtggaat cttcgatgaa cggaatgaag tggatggccg ggaagttctc    360
ttacagtctt agatgttcct tgtggtcaga gcatctcggc cttcacgccg agaggtaat     420 tttaaaaaat ttctagaaac gcctactact atacattttt gacttcagaa acctttattt    480
tcatctcact cgaccaaa                                                   498
```

```
<210> SEQ ID NO 13
<211> LENGTH: 633
<212> TYPE: DNA
<213> ORGANISM: Arabidopsis thaliana
<220> FEATURE:
<221> NAME/KEY: misc_feature
<222> LOCATION: (56)..(57)
<223> OTHER INFORMATION: n is a, c, g, or t

<400> SEQUENCE: 13
tctttggtct gttgatgaga ctctagttgc ggattgcagt gaggtataag catagnncca      60
cagccggtta atattaaatg gagatgaata tgtaattaac acggtttcgt ctgaccgatt     120
caccagagtc tccggttagt tcattaaggg tttgctcaaa cgctttctcc tctgcttccc     180
taatttcgga aacattcgcc tgattttctg agattttgga atttcttcga attgattgcc     240
atgctgagct caagatttcg actgctgaaa tcgaggcgac ttgcggagcc acctccggct     300
gatgtcgcgg ttatgtgtat ttgcaggaaa tgaaagtgat ctccttattg cggcaaatca     360
gccacttcct gtcgactaaa actgtggtgc agcatgtaag aacaaatgca agttcggaca     420
aacgtgttgt cttggtcagt ggttttactt ggcttagtct tcgattctct acgcgtttca     480
gcgtcaagtt ttctagatct ctaaagcttt cgtgctcgcc gatataaatc tctaatatcg     540
gtcccgtaag atcgaattag attcgcgtcg tttttaagg aaccaaaata atggcgcaac     600
aatcgttgtt ctacagtttc atcctcactc gac                                 633

<210> SEQ ID NO 14
<211> LENGTH: 448
<212> TYPE: DNA
<213> ORGANISM: Arabidopsis thaliana
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t

<400> SEQUENCE: 14
ganttcctga taatgatatg tggatggttt gtgcttgtga taaagtattt gaantttaat      60
gttctatgtc agataaaaag tgtgacgttt agattattcc aatttctgtc tcagcgtgat     120
gcggagagga tgtgccagac tctaaaacac gtttctcctg aaatcaattg taaaccgagt     180
ttaaggccat gcacctttg tggaggacct acagccacaa gttcttttca tatcctatcg      240
aatgaggcag acagtgtgaa aggaatggag cttggtgagt tgactatgac tacgactacg     300
acagagcaag taaggaattc ttctgtcttt ccctgancta ggcataggat gtggatatct     360
gttatttctt ctgtccagtg gagaggatcg tttcaactaa cattacaaac tgatttagaa     420
gtttccactg catttcatct cactcgac                                       448

<210> SEQ ID NO 15
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 15
```
acgcgtcgac ccatcatgaa aacgatctca atcttcttcg tc    42

<210> SEQ ID NO 16
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 16
tgtacatgta caagtgagaa cggtagataa gtaagtgg    38

<210> SEQ ID NO 17
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 17
acgcgtcgac caaacgacgt atctcataag tcgacgca    38

<210> SEQ ID NO 18
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 18
tgtacatgta caggagaact ttgaagatca tcgagagg    38

<210> SEQ ID NO 19
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 19
acgcgtcgac ccatcacaca cacatacaca cac    33

<210> SEQ ID NO 20
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 20
tgtacatgta cacagcgtaa atgaagaaca ccccaaactg aac    43

<210> SEQ ID NO 21
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 21
acgcgtcgac atgtcaggat cacatctgcg tttgc    35

<210> SEQ ID NO 22
<211> LENGTH: 35
<212> TYPE: DNA
<213> ORGANISM: Artificial Sequence

```
<220> FEATURE:
<223> OTHER INFORMATION: Synthetic oligonucleotide

<400> SEQUENCE: 22
tgtacatgta catcagcact tgctcctgtt cttcg                              35

<210> SEQ ID NO 23
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 23
acgcgtcgac atggcagggg aacttgtgtc gtttgc                             36

<210> SEQ ID NO 24
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 24
ccttcttcca tatgtcgtcg agg                                           23

<210> SEQ ID NO 25
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 25
cctcgacgac atatggaaga agg                                           23

<210> SEQ ID NO 26
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 26
ccatattcct cctcaccagc tcctctatg                                     29

<210> SEQ ID NO 27
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 27
catagaggag ctggtgagga ggaatatgg                                     29

<210> SEQ ID NO 28
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 28
aaggaaaaaa gcggccgcct ctgtgattgc tgagagcatt cctagtcgtc g            51
```

<210> SEQ ID NO 29
<211> LENGTH: 855
<212> TYPE: PRT
<213> ORGANISM: Arabidopsis thaliana

<400> SEQUENCE: 29

| | | | | | | | | | | | | | | | |
|---|---|---|---|---|---|---|---|---|---|---|---|---|---|---|---|
| Met | Ala | Gly | Glu | Leu | Ile | Ser | Phe | Gly | Ile | Gln | Asn | Leu | Trp | Asn | Leu |
| 1 | | | | 5 | | | | | 10 | | | | | 15 | |
| Leu | Ser | Gln | Glu | Cys | Glu | Leu | Phe | Gln | Gly | Val | Glu | Asp | Gln | Val | Thr |
| | | | 20 | | | | | 25 | | | | | 30 | | |
| Glu | Leu | Lys | Arg | Asp | Leu | Asn | Met | Leu | Ser | Ser | Phe | Leu | Lys | Asp | Ala |
| | | | 35 | | | | | 40 | | | | | 45 | | |
| Asn | Ala | Lys | Lys | His | Thr | Ser | Ala | Val | Val | Lys | Asn | Cys | Val | Glu | Glu |
| | 50 | | | | | 55 | | | | | 60 | | | | |
| Ile | Lys | Glu | Ile | Ile | Tyr | Asp | Gly | Glu | Asp | Thr | Ile | Glu | Thr | Phe | Val |
| 65 | | | | | 70 | | | | | 75 | | | | | 80 |
| Leu | Glu | Gln | Asn | Leu | Gly | Lys | Thr | Ser | Gly | Ile | Lys | Lys | Ser | Ile | Arg |
| | | | | 85 | | | | | 90 | | | | | 95 | |
| Arg | Leu | Ala | Cys | Ile | Ile | Pro | Asp | Arg | Arg | Tyr | Ala | Leu | Gly | Ile |
| | | | 100 | | | | | 105 | | | | | 110 | | |
| Gly | Gly | Leu | Ser | Asn | Arg | Ile | Ser | Lys | Val | Ile | Arg | Asp | Met | Gln | Ser |
| | | | 115 | | | | | 120 | | | | | 125 | | |
| Phe | Gly | Val | Gln | Gln | Ala | Ile | Val | Asp | Gly | Gly | Tyr | Lys | Gln | Pro | Gln |
| | | 130 | | | | | 135 | | | | | 140 | | | |
| Gly | Asp | Lys | Gln | Arg | Glu | Met | Arg | Gln | Lys | Phe | Ser | Lys | Asp | Asp |
| 145 | | | | | 150 | | | | | 155 | | | | | 160 |
| Ser | Asp | Phe | Val | Gly | Leu | Glu | Ala | Asn | Val | Lys | Lys | Leu | Val | Gly | Tyr |
| | | | | 165 | | | | | 170 | | | | | 175 | |
| Leu | Val | Asp | Glu | Ala | Asn | Val | Gln | Val | Val | Ser | Ile | Thr | Gly | Met | Gly |
| | | | 180 | | | | | 185 | | | | | 190 | | |
| Gly | Leu | Gly | Lys | Thr | Thr | Leu | Ala | Lys | Gln | Val | Phe | Asn | His | Glu | Asp |
| | | | 195 | | | | | 200 | | | | | 205 | | |
| Val | Lys | His | Gln | Phe | Asp | Gly | Leu | Ser | Trp | Val | Cys | Val | Ser | Gln | Asp |
| | 210 | | | | | 215 | | | | | 220 | | | | |
| Phe | Thr | Arg | Met | Asn | Val | Trp | Gln | Lys | Ile | Leu | Arg | Asp | Leu | Lys | Pro |
| 225 | | | | | 230 | | | | | 235 | | | | | 240 |
| Lys | Glu | Glu | Lys | Lys | Ile | Met | Glu | Met | Thr | Gln | Asp | Thr | Leu | Gln |
| | | | | 245 | | | | | 250 | | | | | 255 | |
| Gly | Glu | Leu | Ile | Arg | Leu | Leu | Glu | Thr | Ser | Lys | Ser | Leu | Ile | Val | Leu |
| | | | 260 | | | | | 265 | | | | | 270 | | |
| Asp | Asp | Ile | Trp | Glu | Lys | Glu | Asp | Trp | Glu | Leu | Ile | Lys | Pro | Ile | Phe |
| | | | 275 | | | | | 280 | | | | | 285 | | |
| Pro | Pro | Thr | Lys | Gly | Trp | Lys | Val | Leu | Leu | Thr | Ser | Arg | Asn | Glu | Ser |
| | | 290 | | | | | 295 | | | | | 300 | | | |
| Val | Ala | Met | Arg | Arg | Asn | Thr | Ser | Tyr | Ile | Asn | Phe | Lys | Pro | Glu | Cys |
| 305 | | | | | 310 | | | | | 315 | | | | | 320 |
| Leu | Thr | Thr | Glu | Asp | Ser | Trp | Thr | Leu | Phe | Gln | Arg | Ile | Ala | Leu | Pro |
| | | | | 325 | | | | | 330 | | | | | 335 | |
| Met | Lys | Asp | Ala | Ala | Glu | Phe | Lys | Ile | Asp | Glu | Glu | Lys | Glu | Glu | Leu |
| | | | 340 | | | | | 345 | | | | | 350 | | |
| Gly | Lys | Leu | Met | Ile | Lys | His | Cys | Gly | Gly | Leu | Pro | Leu | Ala | Ile | Arg |
| | | | 355 | | | | | 360 | | | | | 365 | | |
| Val | Leu | Gly | Gly | Met | Leu | Ala | Glu | Lys | Tyr | Thr | Ser | His | Asp | Trp | Arg |
| | 370 | | | | | 375 | | | | | 380 | | | | |

```
Arg Leu Ser Glu Asn Ile Gly Ser His Leu Val Gly Gly Arg Thr Asn
385                 390                 395                 400

Phe Asn Asp Asp Asn Asn Thr Cys Asn Asn Val Leu Ser Leu Ser
            405                 410                 415

Phe Glu Glu Leu Pro Ser Tyr Leu Lys His Cys Phe Leu Tyr Leu Ala
            420                 425                 430

His Phe Pro Glu Asp Tyr Glu Ile Lys Val Glu Asn Leu Ser Tyr Tyr
            435                 440                 445

Trp Ala Ala Glu Gly Ile Phe Gln Pro Arg His Tyr Asp Gly Glu Thr
            450                 455                 460

Ile Arg Asp Val Gly Asp Val Tyr Ile Glu Leu Val Arg Arg Asn
465                 470                 475                 480

Met Val Ile Ser Glu Arg Asp Val Lys Thr Ser Arg Phe Glu Thr Cys
            485                 490                 495

His Leu His Asp Met Met Arg Glu Val Cys Leu Leu Lys Ala Lys Glu
            500                 505                 510

Glu Asn Phe Leu Gln Ile Thr Ser Ser Arg Pro Ser Thr Ala Asn Leu
            515                 520                 525

Gln Ser Thr Val Thr Ser Arg Arg Phe Val Tyr Gln Tyr Pro Thr Thr
530                 535                 540

Leu His Val Glu Lys Asp Ile Asn Asn Pro Lys Leu Arg Ala Leu Val
545                 550                 555                 560

Val Val Thr Leu Gly Ser Trp Asn Leu Ala Gly Ser Ser Phe Thr Arg
            565                 570                 575

Leu Glu Leu Leu Arg Val Leu Asp Leu Ile Glu Val Lys Ile Lys Gly
            580                 585                 590

Gly Lys Leu Ala Ser Cys Ile Gly Lys Leu Ile His Leu Arg Tyr Leu
            595                 600                 605

Ser Leu Glu Tyr Ala Glu Val Thr His Ile Pro Tyr Ser Leu Gly Asn
            610                 615                 620

Leu Lys Leu Leu Ile Tyr Leu Asn Leu Ala Ser Phe Gly Arg Ser Thr
625                 630                 635                 640

Phe Val Pro Asn Val Leu Met Gly Met Gln Glu Leu Arg Tyr Leu Ala
            645                 650                 655

Leu Pro Ser Asp Met Gly Arg Lys Thr Lys Leu Glu Leu Ser Asn Leu
            660                 665                 670

Val Lys Leu Glu Thr Leu Glu Asn Phe Ser Thr Glu Asn Ser Ser Leu
            675                 680                 685

Glu Asp Leu Cys Gly Met Val Arg Leu Ser Thr Leu Asn Ile Lys Leu
            690                 695                 700

Ile Glu Glu Thr Ser Leu Glu Thr Leu Ala Ala Ser Ile Gly Gly Leu
705                 710                 715                 720

Lys Tyr Leu Glu Lys Leu Glu Ile Tyr Asp His Gly Ser Glu Met Arg
            725                 730                 735

Thr Lys Glu Ala Gly Ile Val Phe Asp Phe Val His Leu Lys Arg Leu
            740                 745                 750

Trp Leu Lys Leu Tyr Met Pro Arg Leu Ser Thr Glu Gln His Phe Pro
            755                 760                 765

Ser His Leu Thr Thr Leu Tyr Leu Glu Ser Cys Arg Leu Glu Glu Asp
            770                 775                 780

Pro Met Pro Ile Leu Glu Lys Leu Leu Gln Leu Lys Glu Leu Glu Leu
785                 790                 795                 800
```

```
Gly Phe Glu Ser Phe Ser Gly Lys Lys Met Val Cys Ser Ser Gly Gly
                805                 810                 815

Phe Pro Gln Leu Gln Arg Leu Ser Leu Leu Lys Leu Glu Glu Trp Glu
            820                 825                 830

Asp Trp Lys Val Glu Ser Ser Met Pro Leu Leu Arg Thr Leu Asp
        835                 840                 845

Ile Gln Ile His Cys Arg Leu
850                 855

<210> SEQ ID NO 30
<211> LENGTH: 1017
<212> TYPE: PRT
<213> ORGANISM: Arabidopsis thaliana

<400> SEQUENCE: 30

Met Ala Gly Glu Leu Ile Ser Phe Gly Ile Gln Asn Leu Trp Asn Leu
1               5                   10                  15

Leu Ser Gln Glu Cys Glu Leu Phe Gln Gly Val Glu Asp Gln Val Thr
            20                  25                  30

Glu Leu Lys Arg Asp Leu Asn Met Leu Ser Ser Phe Leu Lys Asp Ala
        35                  40                  45

Asn Ala Lys Lys His Thr Ser Ala Val Val Lys Asn Cys Val Glu Glu
    50                  55                  60

Ile Lys Glu Ile Ile Tyr Asp Gly Glu Asp Thr Ile Glu Thr Phe Val
65                  70                  75                  80

Leu Glu Gln Asn Leu Gly Lys Thr Ser Gly Ile Lys Lys Ser Ile Arg
                85                  90                  95

Arg Leu Ala Cys Ile Ile Pro Asp Arg Arg Tyr Ala Leu Gly Ile
            100                 105                 110

Gly Gly Leu Ser Asn Arg Ile Ser Lys Val Ile Arg Asp Met Gln Ser
            115                 120                 125

Phe Gly Val Gln Gln Ala Ile Val Asp Gly Tyr Lys Gln Pro Gln
        130                 135                 140

Gly Asp Lys Gln Arg Glu Met Arg Gln Lys Phe Ser Lys Asp Asp
145                 150                 155                 160

Ser Asp Phe Val Gly Leu Glu Ala Asn Val Lys Lys Leu Val Gly Tyr
                165                 170                 175

Leu Val Asp Glu Ala Asn Val Gln Val Val Ser Ile Thr Gly Met Gly
            180                 185                 190

Gly Leu Gly Lys Thr Thr Leu Ala Lys Gln Val Phe Asn His Glu Asp
        195                 200                 205

Val Lys His Gln Phe Asp Gly Leu Ser Trp Val Cys Val Ser Gln Asp
    210                 215                 220

Phe Thr Arg Met Asn Val Trp Gln Lys Ile Leu Arg Asp Leu Lys Pro
225                 230                 235                 240

Lys Glu Glu Lys Lys Ile Met Glu Met Thr Gln Asp Thr Leu Gln
                245                 250                 255

Gly Glu Leu Ile Arg Leu Leu Glu Thr Ser Lys Ser Leu Ile Val Leu
            260                 265                 270

Asp Asp Ile Trp Glu Lys Glu Asp Trp Glu Leu Ile Lys Pro Ile Phe
        275                 280                 285

Pro Pro Thr Lys Gly Trp Lys Val Leu Leu Thr Ser Arg Asn Glu Ser
    290                 295                 300

Val Ala Met Arg Arg Asn Thr Ser Tyr Ile Asn Phe Lys Pro Glu Cys
305                 310                 315                 320
```

```
Leu Thr Thr Glu Asp Ser Trp Thr Leu Phe Gln Arg Ile Ala Leu Pro
            325                 330                 335

Met Lys Asp Ala Ala Glu Phe Lys Ile Asp Glu Glu Lys Glu Glu Leu
            340                 345                 350

Gly Lys Leu Met Ile Lys His Cys Gly Gly Leu Pro Leu Ala Ile Arg
            355                 360                 365

Val Leu Gly Gly Met Leu Ala Glu Lys Tyr Thr Ser His Asp Trp Arg
        370                 375                 380

Arg Leu Ser Glu Asn Ile Gly Ser His Leu Val Gly Arg Thr Asn
385                 390                 395                 400

Phe Asn Asp Asp Asn Asn Thr Cys Asn Asn Val Leu Ser Leu Ser
                405                 410                 415

Phe Glu Glu Leu Pro Ser Tyr Leu Lys His Cys Phe Leu Tyr Leu Ala
            420                 425                 430

His Phe Pro Glu Asp Tyr Glu Ile Lys Val Glu Asn Leu Ser Tyr Tyr
        435                 440                 445

Trp Ala Ala Glu Gly Ile Phe Gln Pro Arg His Tyr Asp Gly Glu Thr
        450                 455                 460

Ile Arg Asp Val Gly Asp Val Tyr Ile Glu Glu Leu Val Arg Arg Asn
465                 470                 475                 480

Met Val Ile Ser Glu Arg Asp Val Lys Thr Ser Arg Phe Glu Thr Cys
                485                 490                 495

His Leu His Asp Met Met Arg Glu Val Cys Leu Leu Lys Ala Lys Glu
            500                 505                 510

Glu Asn Phe Leu Gln Ile Thr Ser Ser Arg Pro Ser Thr Ala Asn Leu
            515                 520                 525

Gln Ser Thr Val Thr Ser Arg Arg Phe Val Tyr Gln Tyr Pro Thr Thr
        530                 535                 540

Leu His Val Glu Lys Asp Ile Asn Asn Pro Lys Leu Arg Ala Leu Val
545                 550                 555                 560

Val Val Thr Leu Gly Ser Trp Asn Leu Ala Gly Ser Ser Phe Thr Arg
                565                 570                 575

Leu Glu Leu Leu Arg Val Leu Asp Leu Ile Glu Val Lys Ile Lys Gly
            580                 585                 590

Gly Lys Leu Ala Ser Cys Ile Gly Lys Leu Ile His Leu Arg Tyr Leu
            595                 600                 605

Ser Leu Glu Tyr Ala Glu Val Thr His Ile Pro Tyr Ser Leu Gly Asn
        610                 615                 620

Leu Lys Leu Leu Ile Tyr Leu Asn Leu Ala Ser Phe Gly Arg Ser Thr
625                 630                 635                 640

Phe Val Pro Asn Val Leu Met Gly Met Gln Glu Leu Arg Tyr Leu Ala
                645                 650                 655

Leu Pro Ser Asp Met Gly Arg Lys Thr Lys Leu Glu Leu Ser Asn Leu
            660                 665                 670

Val Lys Leu Glu Thr Leu Glu Asn Phe Ser Thr Glu Asn Ser Ser Leu
            675                 680                 685

Glu Asp Leu Cys Gly Met Val Arg Leu Ser Thr Leu Asn Ile Lys Leu
        690                 695                 700

Ile Glu Glu Thr Ser Leu Glu Thr Leu Ala Ala Ser Ile Gly Gly Leu
705                 710                 715                 720

Lys Tyr Leu Glu Lys Leu Glu Ile Tyr Asp His Gly Ser Glu Met Arg
                725                 730                 735
```

-continued

Thr Lys Glu Ala Gly Ile Val Phe Asp Phe Val His Leu Lys Arg Leu
            740                 745                 750

Trp Leu Lys Leu Tyr Met Pro Arg Leu Ser Thr Glu Gln His Phe Pro
            755                 760                 765

Ser His Leu Thr Thr Leu Tyr Leu Glu Ser Cys Arg Leu Glu Glu Asp
            770                 775                 780

Pro Met Pro Ile Leu Glu Lys Leu Leu Gln Leu Lys Glu Leu Glu Leu
785                 790                 795                 800

Gly Phe Glu Ser Phe Ser Gly Lys Lys Met Val Cys Ser Ser Gly Gly
                    805                 810                 815

Phe Pro Gln Leu Gln Arg Leu Ser Leu Leu Lys Leu Glu Glu Trp Glu
            820                 825                 830

Asp Trp Lys Val Glu Glu Ser Ser Met Pro Leu Leu Arg Thr Leu Asp
            835                 840                 845

Ile Gln Val Cys Arg Lys Leu Lys Gln Leu Pro Asp Glu His Leu Pro
            850                 855                 860

Ser His Leu Thr Ser Ile Ser Leu Phe Phe Cys Cys Leu Glu Lys Asp
865                 870                 875                 880

Pro Leu Pro Thr Leu Gly Arg Leu Val Tyr Leu Lys Glu Leu Gln Leu
                    885                 890                 895

Gly Phe Arg Thr Phe Ser Gly Arg Ile Met Val Cys Ser Gly Gly Gly
                    900                 905                 910

Phe Pro Gln Leu Gln Lys Leu Ser Ile Tyr Arg Leu Glu Glu Trp Glu
            915                 920                 925

Glu Trp Ile Val Glu Gln Gly Ser Met Pro Leu His Thr Leu Tyr
            930                 935                 940

Ile Asp Asp Cys Pro Lys Leu Lys Lys Leu Pro Asp Gly Leu Gln Phe
945                 950                 955                 960

Ile Tyr Ser Leu Lys Asn Leu Lys Ile Ser Glu Arg Trp Lys Glu Arg
                    965                 970                 975

Leu Ser Glu Gly Gly Glu Glu Tyr Tyr Lys Val Gln His Ile Pro Ser
            980                 985                 990

Val Glu Phe Tyr His Arg Val Leu His Ile Phe Arg Ser Val Gly Gly
            995                 1000                1005

Asp Ile Thr Gly Arg Leu Leu Met Arg
    1010                1015

<210> SEQ ID NO 31
<211> LENGTH: 1049
<212> TYPE: PRT
<213> ORGANISM: Arabidopsis thaliana

<400> SEQUENCE: 31

Met Ala Gly Glu Leu Ile Ser Phe Gly Ile Gln Asn Leu Trp Asn Leu
1               5                   10                  15

Leu Ser Gln Glu Cys Glu Leu Phe Gln Gly Val Glu Asp Gln Val Thr
            20                  25                  30

Glu Leu Lys Arg Asp Leu Asn Leu Leu Ser Ser Phe Leu Lys Asp Ala
            35                  40                  45

Asp Ala Lys Lys His Thr Ser Ala Val Val Lys Asn Cys Val Glu Glu
            50                  55                  60

Ile Lys Glu Ile Ile Tyr Asp Gly Glu Asp Thr Ile Glu Thr Phe Val
65                  70                  75                  80

Leu Glu Gln Asn Leu Gly Lys Ser Gly Ile Lys Lys Ser Ile Arg
                    85                  90                  95

```
Arg Leu Ala Cys Ile Ile Pro Asp Arg Arg Tyr Ala Leu Gly Ile
            100                 105                 110

Gly Gly Leu Ser Asn Arg Ile Ser Lys Val Ile Arg Asp Met Gln Ser
        115                 120                 125

Phe Gly Val Gln Gln Ala Ile Val Asp Gly Gly Tyr Lys Gln Pro Gln
    130                 135                 140

Gly Asp Lys Gln Arg Glu Met Arg Pro Arg Phe Ser Lys Asp Asp
145                 150                 155                 160

Ser Asp Phe Val Gly Leu Glu Ala Asn Val Lys Lys Leu Val Gly Tyr
                165                 170                 175

Leu Val Asp Glu Ala Asn Val Gln Val Ser Ile Thr Gly Met Gly
            180                 185                 190

Gly Leu Gly Lys Thr Thr Leu Ala Lys Gln Val Phe Asn His Glu Asp
        195                 200                 205

Val Lys His Gln Phe Asp Gly Leu Ser Trp Val Cys Val Ser Gln Asp
    210                 215                 220

Phe Thr Arg Met Asn Val Trp Gln Lys Ile Leu Arg Asp Leu Lys Pro
225                 230                 235                 240

Lys Glu Glu Lys Lys Ile Met Glu Met Thr Gln Asp Thr Leu Gln
            245                 250                 255

Gly Glu Leu Ile Arg Leu Leu Glu Thr Ser Lys Ser Leu Ile Val Leu
        260                 265                 270

Asp Asp Ile Trp Glu Lys Glu Asp Trp Glu Leu Ile Lys Pro Ile Phe
    275                 280                 285

Pro Pro Thr Lys Gly Trp Lys Val Leu Leu Thr Ser Arg Asn Glu Ser
290                 295                 300

Val Ala Met Arg Arg Asn Thr Ser Tyr Ile Asn Phe Lys Pro Glu Cys
305                 310                 315                 320

Leu Thr Thr Glu Asp Ser Trp Thr Leu Phe Gln Arg Ile Ala Leu Pro
            325                 330                 335

Met Lys Asp Ala Ala Glu Phe Lys Ile Asp Glu Glu Lys Glu Leu
        340                 345                 350

Gly Lys Leu Met Ile Lys His Cys Gly Gly Leu Pro Leu Ala Ile Arg
    355                 360                 365

Val Leu Gly Gly Met Leu Ala Glu Lys Tyr Thr Ser His Asp Trp Arg
370                 375                 380

Arg Leu Ser Glu Asn Ile Gly Ser His Leu Val Gly Gly Arg Thr Asn
385                 390                 395                 400

Phe Asn Asp Asp Asn Asn Thr Cys Asn Tyr Val Leu Ser Leu Ser
            405                 410                 415

Phe Glu Glu Leu Pro Ser Tyr Leu Lys His Cys Phe Leu Tyr Leu Ala
        420                 425                 430

His Phe Pro Asp Asp Tyr Glu Ile Asn Val Lys Asn Leu Ser Tyr Tyr
    435                 440                 445

Trp Ala Ala Glu Gly Ile Phe Gln Pro Arg His Tyr Asp Gly Glu Ile
450                 455                 460

Ile Arg Asp Val Gly Asp Val Tyr Ile Glu Glu Leu Val Arg Arg Asn
465                 470                 475                 480

Met Val Ile Ser Glu Arg Asp Val Lys Thr Ser Arg Phe Glu Thr Cys
            485                 490                 495

His Leu His Asp Met Met Arg Glu Val Cys Leu Leu Lys Ala Lys Glu
        500                 505                 510
```

-continued

Glu Asn Phe Leu Gln Ile Thr Ser Ser Arg Thr Ser Thr Gly Asn Ser
            515                 520                 525

Leu Ser Ile Val Thr Ser Arg Arg Leu Val Tyr Gln Tyr Pro Ile Thr
530                 535                 540

Leu Asp Val Glu Lys Asp Ile Asn Asp Pro Lys Leu Arg Ser Leu Val
545                 550                 555                 560

Val Val Ala Asn Thr Tyr Met Phe Trp Gly Trp Ser Trp Met Leu
            565                 570                 575

Leu Gly Ser Ser Phe Ile Arg Leu Glu Leu Leu Arg Val Leu Asp Ile
                580                 585                 590

His Arg Ala Lys Leu Lys Gly Gly Lys Leu Ala Ser Ser Ile Gly Gln
            595                 600                 605

Leu Ile His Leu Arg Tyr Leu Asn Leu Lys His Ala Glu Val Thr His
            610                 615                 620

Ile Pro Tyr Ser Leu Gly Asn Leu Lys Leu Leu Ile Tyr Leu Asn Leu
625                 630                 635                 640

Val Ile Leu Val Ser Gly Ser Thr Leu Val Pro Asn Val Leu Lys Glu
                645                 650                 655

Met Gln Gln Leu Arg Tyr Leu Ala Leu Pro Lys Asp Met Gly Arg Lys
            660                 665                 670

Thr Lys Leu Glu Leu Ser Asn Leu Val Lys Leu Glu Thr Leu Lys Asn
            675                 680                 685

Phe Ser Thr Lys Asn Cys Ser Leu Glu Asp Leu Arg Gly Met Val Arg
            690                 695                 700

Leu Arg Thr Leu Thr Ile Glu Leu Arg Lys Glu Thr Ser Leu Glu Thr
705                 710                 715                 720

Leu Ala Ala Ser Ile Gly Gly Leu Lys Tyr Leu Glu Ser Leu Thr Ile
                725                 730                 735

Thr Asp Leu Gly Ser Glu Met Arg Thr Lys Glu Ala Gly Ile Val Phe
            740                 745                 750

Asp Phe Val Tyr Leu Lys Thr Leu Thr Leu Lys Leu Tyr Met Pro Arg
            755                 760                 765

Leu Ser Lys Glu Gln His Phe Pro Ser His Leu Thr Thr Leu Tyr Leu
770                 775                 780

Gln His Cys Arg Leu Glu Glu Asp Pro Met Pro Ile Leu Glu Lys Leu
785                 790                 795                 800

His Gln Leu Lys Glu Leu Gly Leu Arg Arg Lys Ser Phe Ser Gly Lys
                805                 810                 815

Glu Met Val Cys Ser Ser Gly Gly Phe Pro Gln Leu Gln Lys Leu Ser
            820                 825                 830

Ile Lys Gly Leu Glu Glu Trp Glu Asp Trp Lys Val Glu Glu Ser Ser
            835                 840                 845

Met Pro Val Leu His Thr Leu Asp Ile Arg Asp Cys Arg Lys Leu Lys
850                 855                 860

Gln Leu Pro Asp Glu His Leu Pro Ser His Leu Thr Ser Ile Ser Leu
865                 870                 875                 880

Phe Phe Cys Cys Leu Glu Glu Asp Pro Met Pro Thr Leu Glu Arg Leu
                885                 890                 895

Val His Leu Lys Glu Leu Gln Leu Leu Phe Arg Ser Phe Ser Gly Arg
            900                 905                 910

Ile Met Val Cys Ala Gly Ser Gly Phe Pro Gln Leu His Lys Leu Lys
            915                 920                 925

Leu Ser Glu Leu Asp Gly Leu Glu Glu Trp Ile Val Glu Asp Gly Ser

```
                930                935                940
Met Pro Gln Leu His Thr Leu Glu Ile Arg Arg Cys Pro Lys Leu Lys
945                950                955                960

Lys Leu Pro Asn Gly Phe Pro Gln Leu Gln Asn Leu Glu Leu Asn Glu
                965                970                975

Leu Glu Glu Trp Glu Trp Ile Val Glu Asp Gly Ser Met Pro Leu
            980                985                990

Leu His Thr Leu Arg Ile Trp Asn Cys Pro Lys Leu Lys Gln Leu Pro
            995                1000               1005

Asp Gly Leu Arg Phe Ile Tyr Ser Leu Lys Asn Leu Thr Val Pro
        1010               1015               1020

Lys Arg Trp Lys Lys Arg Leu Ser Lys Gly Gly Glu Asp Tyr Tyr
        1025               1030               1035

Lys Val Gln His Ile Pro Ser Val Glu Phe Tyr
        1040               1045

<210> SEQ ID NO 32
<211> LENGTH: 1049
<212> TYPE: PRT
<213> ORGANISM: Arabidopsis thaliana

<400> SEQUENCE: 32

Met Ala Gly Glu Leu Ile Ser Phe Gly Ile Gln Asn Leu Trp Asn Leu
1               5                   10                  15

Leu Ser Gln Glu Cys Glu Leu Phe Gln Gly Val Glu Asp Gln Val Thr
                20                  25                  30

Glu Leu Lys Arg Asp Leu Asn Leu Ser Ser Phe Leu Lys Asp Ala
            35                  40                  45

Asp Ala Lys Lys His Thr Ser Ala Val Val Lys Asn Cys Val Glu Glu
50                  55                  60

Ile Lys Glu Ile Ile Tyr Asp Gly Glu Asp Thr Ile Glu Thr Phe Val
65                  70                  75                  80

Leu Glu Gln Asn Leu Gly Lys Thr Ser Gly Ile Lys Lys Ser Ile Arg
                85                  90                  95

Arg Leu Ala Cys Ile Ile Pro Asp Arg Arg Tyr Ala Leu Gly Ile
                100                 105                 110

Gly Gly Leu Ser Asn Arg Ile Ser Lys Val Ile Arg Asp Met Gln Ser
            115                 120                 125

Phe Gly Val Gln Gln Ala Ile Val Asp Gly Gly Tyr Lys Gln Pro Gln
130                 135                 140

Gly Asp Lys Gln Arg Glu Met Arg Pro Arg Phe Ser Lys Asp Asp
145                 150                 155                 160

Ser Asp Phe Val Gly Leu Glu Ala Asn Val Lys Lys Leu Val Gly Tyr
                165                 170                 175

Leu Val Asp Glu Ala Asn Val Gln Val Val Ser Ile Thr Gly Met Gly
                180                 185                 190

Gly Leu Gly Lys Thr Thr Leu Ala Lys Gln Val Phe Asn His Glu Asp
            195                 200                 205

Val Lys His Gln Phe Asp Gly Leu Ser Trp Val Cys Val Ser Gln Asp
        210                 215                 220

Phe Thr Arg Met Asn Val Trp Gln Lys Ile Leu Arg Asp Leu Lys Pro
225                 230                 235                 240

Lys Glu Glu Glu Lys Lys Ile Glu Met Thr Gln Asp Thr Leu Gln
                245                 250                 255
```

-continued

```
Gly Glu Leu Ile Arg Leu Leu Glu Thr Ser Lys Ser Leu Ile Val Leu
            260                 265                 270

Asp Asp Ile Trp Glu Lys Glu Asp Trp Glu Leu Ile Lys Pro Ile Phe
        275                 280                 285

Pro Pro Thr Lys Gly Trp Lys Val Leu Leu Thr Ser Arg Asn Glu Ser
290                 295                 300

Val Ala Met Arg Arg Asn Thr Ser Tyr Ile Asn Phe Lys Pro Glu Cys
305                 310                 315                 320

Leu Thr Thr Glu Asp Ser Trp Thr Leu Phe Gln Arg Ile Ala Leu Pro
                325                 330                 335

Met Lys Asp Ala Ala Glu Phe Lys Ile Asp Glu Glu Lys Glu Glu Leu
            340                 345                 350

Gly Lys Leu Met Ile Lys His Cys Gly Gly Leu Pro Leu Ala Ile Arg
        355                 360                 365

Val Leu Gly Gly Met Leu Ala Glu Lys Tyr Thr Ser His Asp Trp Arg
370                 375                 380

Arg Leu Ser Glu Asn Ile Gly Ser His Leu Val Gly Gly Arg Thr Asn
385                 390                 395                 400

Phe Asn Asp Asp Asn Asn Thr Cys Asn Tyr Val Leu Ser Leu Ser
                405                 410                 415

Phe Glu Glu Leu Pro Ser Tyr Leu Lys His Cys Phe Leu Tyr Leu Ala
            420                 425                 430

His Phe Pro Asp Asp Tyr Glu Ile Asn Val Lys Asn Leu Ser Tyr Tyr
        435                 440                 445

Trp Ala Ala Glu Gly Ile Phe Gln Pro Arg His Tyr Asp Gly Glu Ile
    450                 455                 460

Ile Arg Asp Val Gly Asp Val Tyr Ile Glu Glu Leu Val Arg Arg Asn
465                 470                 475                 480

Met Val Ile Ser Glu Arg Asp Val Lys Thr Ser Arg Phe Glu Thr Cys
                485                 490                 495

His Leu His Asp Met Met Arg Glu Val Cys Leu Leu Lys Ala Lys Glu
            500                 505                 510

Glu Asn Phe Leu Gln Ile Thr Ser Ser Arg Thr Ser Thr Gly Asn Ser
        515                 520                 525

Leu Ser Ile Val Thr Ser Arg Arg Leu Val Tyr Gln Tyr Pro Ile Thr
530                 535                 540

Leu Asp Val Glu Lys Asp Ile Asn Asp Pro Lys Leu Arg Ser Leu Val
545                 550                 555                 560

Val Val Ala Asn Thr Tyr Met Phe Trp Gly Gly Trp Ser Trp Met Leu
                565                 570                 575

Leu Gly Ser Ser Phe Ile Arg Leu Glu Leu Leu Arg Val Leu Asp Ile
            580                 585                 590

His Arg Ala Lys Leu Lys Gly Gly Lys Leu Ala Ser Ser Ile Gly Gln
        595                 600                 605

Leu Ile His Leu Arg Tyr Leu Asn Leu Lys His Ala Glu Val Thr His
    610                 615                 620

Ile Pro Tyr Ser Leu Gly Asn Leu Lys Leu Leu Ile Tyr Leu Asn Leu
625                 630                 635                 640

Val Ile Leu Val Ser Gly Ser Thr Leu Val Pro Asn Val Leu Lys Glu
                645                 650                 655

Met Gln Gln Leu Arg Tyr Leu Ala Leu Pro Lys Asp Met Gly Arg Lys
            660                 665                 670

Thr Lys Leu Glu Leu Ser Asn Leu Val Lys Leu Glu Thr Leu Lys Asn
```

```
                    675                 680                 685
       Phe Ser Thr Lys Asn Cys Ser Leu Glu Asp Leu Arg Gly Met Val Arg
           690                 695                 700

Leu Arg Thr Leu Thr Ile Glu Leu Arg Lys Glu Thr Ser Leu Glu Thr
       705                 710                 715                 720

Leu Ala Ala Ser Ile Gly Gly Leu Lys Tyr Leu Glu Ser Leu Thr Ile
                       725                 730                 735

Thr Asp Leu Gly Ser Glu Met Arg Thr Lys Glu Ala Gly Ile Val Phe
                   740                 745                 750

Asp Phe Val Tyr Leu Lys Thr Leu Thr Leu Lys Leu Tyr Met Pro Arg
               755                 760                 765

Leu Ser Lys Glu Gln His Phe Pro Ser His Leu Thr Thr Leu Tyr Leu
       770                 775                 780

Gln His Cys Arg Leu Glu Glu Asp Pro Met Pro Ile Leu Glu Lys Leu
       785                 790                 795                 800

His Gln Leu Lys Glu Leu Glu Leu Arg Arg Lys Ser Phe Ser Gly Lys
                       805                 810                 815

Glu Met Val Cys Ser Ser Gly Gly Phe Pro Gln Leu Gln Lys Leu Ser
                   820                 825                 830

Ile Lys Gly Leu Glu Glu Trp Glu Asp Trp Lys Val Glu Ser Ser
               835                 840                 845

Met Pro Val Leu His Thr Leu Asp Ile Arg Asp Cys Arg Lys Leu Lys
       850                 855                 860

Gln Leu Pro Asp Glu His Leu Pro Ser His Leu Thr Ser Ile Ser Leu
       865                 870                 875                 880

Phe Phe Cys Cys Leu Glu Glu Asp Pro Met Pro Thr Leu Glu Arg Leu
                       885                 890                 895

Val His Leu Lys Glu Leu Gln Leu Leu Phe Arg Ser Phe Ser Gly Arg
                   900                 905                 910

Ile Met Val Cys Ala Gly Ser Gly Phe Pro Gln Leu His Lys Leu Lys
               915                 920                 925

Leu Ser Glu Leu Asp Gly Leu Glu Glu Trp Ile Val Glu Asp Gly Ser
       930                 935                 940

Met Pro Gln Leu His Thr Leu Glu Ile Arg Arg Cys Pro Lys Leu Lys
       945                 950                 955                 960

Lys Leu Pro Asn Gly Phe Pro Gln Leu Gln Asn Leu Glu Leu Asn Glu
                       965                 970                 975

Leu Glu Glu Trp Glu Glu Trp Ile Val Glu Asp Gly Ser Met Pro Leu
                   980                 985                 990

Leu His Thr Leu Arg Ile Trp Asn Cys Pro Lys Leu Lys Gln Leu Pro
               995                 1000                1005

Asp Gly Leu Arg Phe Ile Tyr Ser Leu Lys Asn Leu Thr Val Pro
           1010                1015                1020

Lys Arg Trp Lys Lys Arg Leu Ser Lys Gly Gly Glu Asp Tyr Tyr
           1025                1030                1035

Lys Val Gln His Ile Pro Ser Val Glu Phe Tyr
           1040                1045

<210> SEQ ID NO 33
<211> LENGTH: 899
<212> TYPE: PRT
<213> ORGANISM: Arabidopsis thaliana

<400> SEQUENCE: 33
```

-continued

```
Met Glu Leu Val Ser Phe Gly Val Glu Lys Leu Trp Asp Arg Leu Ser
1               5                   10                  15

Gln Glu Tyr Asp Gln Phe Lys Gly Val Glu Asp Gln Val Thr Glu Leu
            20                  25                  30

Lys Ser Asn Leu Asn Leu Leu Lys Ser Phe Leu Lys Asp Ala Asp Ala
        35                  40                  45

Lys Lys His Ile Ser Glu Met Val Arg His Cys Val Glu Glu Ile Lys
50                  55                  60

Asp Ile Val Tyr Asp Thr Glu Asp Ile Ile Glu Thr Phe Ile Leu Lys
65                  70                  75                  80

Glu Lys Val Glu Met Lys Arg Gly Ile Met Lys Arg Ile Lys Arg Phe
                85                  90                  95

Ala Ser Thr Ile Met Asp Arg Arg Glu Leu Ala Ser Asp Ile Gly Gly
            100                 105                 110

Ile Ser Lys Arg Ile Ser Lys Val Ile Gln Asp Met Gln Ser Phe Gly
        115                 120                 125

Val Gln Gln Ile Ile Thr Asp Gly Ser Arg Ser His Pro Leu Gln
    130                 135                 140

Glu Arg Gln Arg Glu Met Arg His Thr Phe Ser Arg Asp Ser Glu Asn
145                 150                 155                 160

Asp Phe Val Gly Met Glu Ala Asn Val Lys Lys Leu Val Gly Tyr Leu
                165                 170                 175

Val Glu Lys Asp Asp Tyr Gln Ile Val Ser Leu Thr Gly Met Gly Gly
            180                 185                 190

Leu Gly Lys Thr Thr Leu Ala Arg Gln Val Phe Asn His Asp Val Val
        195                 200                 205

Lys Asp Arg Phe Asp Gly Phe Ala Trp Val Ser Val Ser Gln Glu Phe
    210                 215                 220

Thr Arg Ile Ser Val Trp Gln Thr Ile Leu Gln Asn Leu Thr Ser Lys
225                 230                 235                 240

Glu Arg Lys Asp Glu Ile Gln Asn Met Lys Glu Ala Asp Leu His Asp
                245                 250                 255

Asp Leu Phe Arg Leu Leu Glu Ser Ser Lys Thr Leu Ile Val Leu Asp
            260                 265                 270

Asp Ile Trp Lys Glu Glu Asp Trp Asp Leu Ile Lys Pro Ile Phe Pro
        275                 280                 285

Pro Lys Lys Gly Trp Lys Val Leu Leu Thr Ser Arg Thr Glu Ser Ile
    290                 295                 300

Ala Met Arg Gly Asp Thr Thr Tyr Ile Ser Phe Lys Pro Lys Cys Leu
305                 310                 315                 320

Ser Ile Pro Asp Ser Trp Thr Leu Phe Gln Ser Ile Ala Met Pro Arg
                325                 330                 335

Lys Asp Thr Ser Glu Phe Lys Val Asp Glu Glu Met Glu Asn Met Gly
            340                 345                 350

Lys Lys Met Ile Lys His Cys Gly Gly Leu Ser Leu Ala Val Lys Val
        355                 360                 365

Leu Gly Gly Leu Leu Ala Ala Lys Tyr Thr Leu His Asp Trp Lys Arg
    370                 375                 380

Leu Ser Glu Asn Ile Gly Ser His Ile Val Glu Arg Thr Ser Gly Asn
385                 390                 395                 400

Asn Ser Ser Ile Asp His Val Leu Ser Val Ser Phe Glu Glu Leu Pro
                405                 410                 415

Asn Tyr Leu Lys His Cys Phe Leu Tyr Leu Ala His Phe Pro Glu Asp
```

```
                420             425             430
His Glu Ile Asp Val Glu Lys Leu His Tyr Tyr Trp Ala Ala Glu Gly
        435                 440                 445

Ile Ser Glu Arg Arg Arg Tyr Asp Gly Glu Thr Ile Arg Asp Thr Gly
        450                 455                 460

Asp Ser Tyr Ile Glu Glu Leu Val Arg Arg Asn Met Val Ile Ser Glu
465                 470                 475                 480

Arg Asp Val Met Thr Ser Arg Phe Glu Thr Cys Arg Leu His Asp Met
                485                 490                 495

Met Arg Glu Ile Cys Leu Phe Lys Ala Lys Glu Glu Asn Phe Leu Gln
                500                 505                 510

Ile Val Ser Asn His Ser Pro Thr Ser Asn Pro Gln Thr Leu Gly Ala
            515                 520                 525

Ser Arg Arg Phe Val Leu His Asn Pro Thr Thr Leu His Val Glu Arg
        530                 535                 540

Tyr Lys Asn Asn Pro Lys Leu Arg Ser Leu Val Val Tyr Asp Asp
545                 550                 555                 560

Ile Gly Asn Arg Arg Trp Met Leu Ser Gly Ser Ile Phe Thr Arg Val
                565                 570                 575

Lys Leu Leu Arg Val Leu Asp Leu Val Gln Ala Lys Phe Lys Gly Gly
                580                 585                 590

Lys Leu Pro Ser Asp Ile Gly Lys Leu Ile His Leu Arg Tyr Leu Ser
            595                 600                 605

Leu Lys Asp Ala Lys Val Ser His Leu Pro Ser Ser Leu Arg Asn Leu
        610                 615                 620

Val Leu Leu Ile Tyr Leu Asp Ile Arg Thr Asp Phe Thr Asp Ile Phe
625                 630                 635                 640

Val Pro Asn Val Phe Met Gly Met Arg Glu Leu Arg Tyr Leu Glu Leu
                645                 650                 655

Pro Arg Phe Met His Glu Lys Thr Lys Leu Glu Leu Ser Asn Leu Glu
                660                 665                 670

Lys Leu Glu Ala Leu Glu Asn Phe Ser Thr Lys Ser Ser Ser Leu Glu
            675                 680                 685

Asp Leu Arg Gly Met Val Arg Leu Arg Thr Leu Val Ile Ile Leu Ser
        690                 695                 700

Glu Gly Thr Ser Leu Gln Thr Leu Ser Ala Ser Val Cys Gly Leu Arg
705                 710                 715                 720

His Leu Glu Asn Phe Lys Ile Met Glu Asn Ala Gly Val Asn Arg Met
                725                 730                 735

Gly Glu Glu Arg Met Val Leu Asp Phe Thr Tyr Leu Lys Lys Leu Thr
                740                 745                 750

Leu Ser Ile Glu Met Pro Arg Leu Pro Lys Ile Gln His Leu Pro Ser
            755                 760                 765

His Leu Thr Val Leu Asp Leu Ser Tyr Cys Cys Leu Glu Glu Asp Pro
        770                 775                 780

Met Pro Ile Leu Glu Lys Leu Leu Glu Leu Lys Asp Leu Ser Leu Asp
785                 790                 795                 800

Tyr Leu Ser Phe Ser Gly Arg Lys Met Val Cys Ser Ala Gly Gly Phe
                805                 810                 815

Pro Gln Leu Arg Lys Leu Ala Leu Asp Glu Gln Glu Glu Trp Glu Glu
                820                 825                 830

Trp Ile Val Glu Glu Gly Ser Met Ser Arg Leu His Thr Leu Ser Ile
            835                 840                 845
```

Trp Ser Ser Thr Leu Lys Glu Leu Pro Asp Gly Leu Arg Phe Ile Tyr
850                 855                 860

Ser Leu Lys Asn Leu Ile Met Gly Lys Ser Trp Met Glu Arg Leu Ser
865                 870                 875                 880

Glu Arg Gly Glu Phe Tyr Lys Val Gln Asn Ile Pro Phe Ile Lys
            885                 890                 895

Phe Ser Ser

<210> SEQ ID NO 34
<211> LENGTH: 900
<212> TYPE: PRT
<213> ORGANISM: Arabidopsis thaliana

<400> SEQUENCE: 34

Met Val Glu Ala Ile Val Ser Phe Gly Val Glu Lys Leu Trp Asp Arg
1               5                   10                  15

Leu Thr Gln Glu Tyr Glu Gln Phe Gln Gly Val Glu Asp Arg Ile Ala
                20                  25                  30

Glu Leu Lys Ser Asn Leu Asn Leu Leu Lys Ser Phe Leu Lys Asp Ala
            35                  40                  45

Glu Ala Lys Lys Asn Thr Ser Gln Met Val Arg His Cys Val Glu Glu
50                  55                  60

Ile Lys Glu Ile Val Tyr Asp Thr Glu Asn Met Ile Glu Thr Phe Ile
65                  70                  75                  80

Leu Lys Glu Ala Ala Arg Lys Arg Ser Gly Ile Ile Arg Arg Ile Thr
                85                  90                  95

Lys Leu Thr Cys Ile Lys Val His Arg Trp Glu Phe Ala Ser Asp Ile
            100                 105                 110

Gly Gly Ile Ser Lys Arg Ile Ser Lys Val Ile Gln Asp Met His Ser
        115                 120                 125

Phe Gly Val Gln Gln Met Ile Ser Asp Gly Ser Gln Ser Ser His Leu
130                 135                 140

Leu Gln Glu Arg Glu Arg Glu Met Arg Gln Thr Phe Ser Arg Gly Tyr
145                 150                 155                 160

Glu Ser Asp Phe Val Gly Leu Glu Val Asn Val Lys Lys Leu Val Gly
                165                 170                 175

Tyr Leu Val Glu Glu Asp Asp Ile Gln Ile Val Ser Val Thr Gly Met
            180                 185                 190

Gly Gly Leu Gly Lys Thr Thr Leu Ala Arg Gln Val Phe Asn His Glu
        195                 200                 205

Asp Val Lys His Gln Phe Asp Arg Leu Ala Trp Val Cys Val Ser Gln
210                 215                 220

Glu Phe Thr Arg Lys Asn Val Trp Gln Met Ile Leu Gln Asn Leu Thr
225                 230                 235                 240

Ser Arg Glu Thr Lys Asp Glu Ile Leu Gln Met Glu Glu Ala Glu Leu
                245                 250                 255

His Asp Glu Leu Phe Gln Leu Leu Glu Thr Ser Lys Ser Leu Ile Val
            260                 265                 270

Phe Asp Asp Ile Trp Lys Glu Asp Trp Gly Leu Ile Asn Pro Ile
        275                 280                 285

Phe Pro Pro Lys Lys Glu Thr Ile Ala Met His Gly Asn Arg Arg Tyr
290                 295                 300

Val Asn Phe Lys Pro Glu Cys Leu Thr Ile Leu Glu Ser Trp Ile Leu
305                 310                 315                 320

```
Phe Gln Arg Ile Ala Met Pro Arg Val Asp Glu Ser Glu Phe Lys Val
                325                 330                 335

Asp Lys Glu Met Glu Met Met Gly Lys Gln Met Ile Lys Tyr Cys Gly
            340                 345                 350

Gly Leu Pro Leu Ala Val Lys Val Leu Gly Gly Leu Leu Ala Ala Lys
        355                 360                 365

Tyr Thr Phe His Asp Trp Lys Arg Leu Ser Glu Asn Ile Gly Cys His
    370                 375                 380

Ile Val Gly Arg Thr Asp Phe Ser Asp Gly Asn Asn Ser Ser Val Tyr
385                 390                 395                 400

His Val Leu Ser Leu Ser Phe Glu Glu Leu Pro Ser Tyr Leu Lys His
                405                 410                 415

Cys Phe Leu Tyr Leu Ala His Phe Pro Glu Asp His Asn Ile Lys Val
            420                 425                 430

Glu Lys Leu Ser Tyr Cys Trp Ala Ala Glu Gly Ile Leu Glu Pro Arg
        435                 440                 445

His Tyr His Gly Gln Thr Ile Arg Asp Val Gly Glu Ser Tyr Ile Glu
    450                 455                 460

Glu Leu Val Arg Arg Asn Met Val Ile Ala Glu Arg Asp Val Thr Thr
465                 470                 475                 480

Leu Arg Phe Glu Ala Cys His Leu His Asp Met Met Arg Glu Val Cys
                485                 490                 495

Leu Leu Lys Ala Lys Glu Glu Asn Phe Val Gln Ile Ala Ser Ile Leu
            500                 505                 510

Pro Pro Thr Ala Asn Ser Gln Tyr Pro Gly Thr Ser Arg Arg Phe Val
        515                 520                 525

Ser Gln Asn Pro Thr Thr Leu His Val Ser Arg Asp Ile Asn Asn Pro
    530                 535                 540

Lys Leu Gln Ser Leu Leu Ile Val Trp Glu Asn Arg Arg Lys Ser Trp
545                 550                 555                 560

Lys Leu Leu Gly Ser Ser Phe Ile Arg Leu Glu Leu Arg Val Leu
                565                 570                 575

Asp Leu Tyr Lys Ala Lys Phe Glu Gly Arg Asn Leu Pro Ser Gly Ile
            580                 585                 590

Gly Lys Leu Ile His Leu Arg Tyr Leu Asn Leu Asp Leu Ala Arg Val
        595                 600                 605

Ser Arg Leu Pro Ser Ser Leu Gly Asn Leu Arg Leu Leu Ile Tyr Leu
    610                 615                 620

Asp Ile Asn Val Cys Thr Lys Ser Leu Phe Val Pro Asn Cys Leu Met
625                 630                 635                 640

Gly Met His Glu Leu Arg Tyr Leu Arg Leu Pro Phe Asn Thr Ser Lys
                645                 650                 655

Glu Ile Lys Leu Gly Leu Cys Asn Leu Val Asn Leu Glu Thr Leu Glu
            660                 665                 670

Asn Phe Ser Thr Glu Asn Ser Ser Leu Glu Asp Leu Arg Gly Met Val
        675                 680                 685

Ser Leu Arg Thr Leu Thr Ile Gly Leu Phe Lys His Ile Ser Lys Glu
    690                 695                 700

Thr Leu Phe Ala Ser Ile Leu Gly Met Arg His Leu Glu Asn Leu Ser
705                 710                 715                 720

Ile Arg Thr Pro Asp Gly Ser Ser Lys Phe Lys Arg Ile Met Glu Asp
                725                 730                 735
```

Gly Ile Val Leu Asp Ala Ile His Leu Lys Gln Leu Asn Leu Arg Leu
                740                 745                 750

Tyr Met Pro Lys Leu Pro Asp Glu Gln His Phe Pro Ser His Leu Thr
            755                 760                 765

Ser Ile Ser Leu Asp Gly Cys Cys Leu Val Glu Asp Pro Leu Pro Ile
770                 775                 780

Leu Glu Lys Leu Leu Glu Leu Lys Glu Val Arg Leu Asp Phe Arg Ala
785                 790                 795                 800

Phe Cys Gly Lys Arg Met Val Ser Ser Asp Gly Gly Phe Pro Gln Leu
                805                 810                 815

His Arg Leu Tyr Ile Trp Gly Leu Ala Glu Trp Glu Glu Trp Ile Val
            820                 825                 830

Glu Glu Gly Ser Met Pro Arg Leu His Thr Leu Thr Ile Trp Asn Cys
        835                 840                 845

Gln Lys Leu Lys Gln Leu Pro Asp Gly Leu Arg Phe Ile Tyr Ser Ile
    850                 855                 860

Lys Asp Leu Asp Met Asp Lys Lys Trp Lys Glu Ile Leu Ser Glu Gly
865                 870                 875                 880

Gly Glu Glu Tyr Tyr Lys Val Gln His Ile Pro Ser Val Lys Phe Glu
                885                 890                 895

Lys Asp Tyr Lys
            900

<210> SEQ ID NO 35
<211> LENGTH: 907
<212> TYPE: PRT
<213> ORGANISM: Arabidopsis thaliana

<400> SEQUENCE: 35

Met Ala Gly Glu Leu Val Ser Phe Gly Ile Lys Lys Leu Trp Asp Leu
1               5                   10                  15

Leu Ser Gln Glu Cys Glu Gln Phe Gln Gly Val Glu Asp Gln Val Thr
            20                  25                  30

Gly Leu Lys Arg Asp Leu Asn Leu Leu Ser Ser Phe Leu Lys Asp Ala
        35                  40                  45

Asp Ala Lys Lys His Thr Thr Ala Val Val Arg Asn Val Val Glu Glu
    50                  55                  60

Ile Lys Glu Ile Val Tyr Asp Ala Glu Asp Ile Ile Glu Thr Tyr Leu
65                  70                  75                  80

Leu Lys Glu Lys Leu Trp Lys Thr Ser Gly Ile Lys Met Arg Ile Arg
                85                  90                  95

Arg His Ala Cys Ile Ile Ser Asp Arg Arg Asn Ala Leu Asp Val
            100                 105                 110

Gly Gly Ile Arg Thr Arg Ile Ser Asp Val Ile Arg Asp Met Gln Ser
        115                 120                 125

Phe Gly Val Gln Gln Ala Ile Val Asp Gly Gly Tyr Met Gln Pro Gln
    130                 135                 140

Gly Asp Arg Gln Arg Glu Met Arg Gln Thr Phe Ser Lys Asp Tyr Glu
145                 150                 155                 160

Ser Asp Phe Val Gly Leu Glu Val Asn Val Lys Lys Leu Val Gly Tyr
                165                 170                 175

Leu Val Asp Glu Glu Asn Val Gln Val Val Ser Ile Thr Gly Met Gly
            180                 185                 190

Gly Leu Gly Lys Thr Thr Leu Ala Arg Gln Val Phe Asn His Glu Asp
        195                 200                 205

```
Val Lys His Gln Phe Asp Arg Leu Ala Trp Val Cys Val Ser Gln Glu
    210                 215                 220
Phe Thr Arg Lys Asn Val Trp Gln Met Ile Leu Gln Asn Leu Thr Ser
225                 230                 235                 240
Arg Glu Lys Lys Asp Glu Ile Leu Gln Met Glu Glu Ala Glu Leu His
                245                 250                 255
Asp Lys Leu Phe Gln Leu Leu Glu Thr Ser Lys Ser Leu Ile Val Phe
            260                 265                 270
Asp Asp Ile Trp Lys Asp Glu Asp Trp Asp Leu Ile Lys Pro Ile Phe
        275                 280                 285
Pro Pro Asn Lys Gly Trp Lys Val Leu Leu Thr Ser Gln Asn Glu Ser
    290                 295                 300
Val Ala Val Arg Gly Asp Ile Lys Tyr Leu Asn Phe Lys Pro Glu Cys
305                 310                 315                 320
Leu Ala Ile Glu Asp Ser Trp Thr Leu Phe Gln Arg Ile Ala Phe Pro
                325                 330                 335
Lys Lys Asp Ala Ser Glu Ser Lys Val Asp Glu Met Glu Asp Met
            340                 345                 350
Gly Lys Gln Met Leu Lys His Cys Gly Gly Leu Pro Leu Ala Ile Lys
        355                 360                 365
Val Leu Gly Gly Leu Leu Ala Ala Lys Tyr Thr Met His Asp Trp Glu
    370                 375                 380
Arg Leu Ser Val Asn Ile Gly Ser Asp Ile Val Gly Arg Thr Ser Ser
385                 390                 395                 400
Asn Asn Ser Ser Ile Tyr His Val Leu Ser Met Ser Phe Glu Glu Leu
                405                 410                 415
Pro Ser Tyr Leu Lys His Cys Phe Leu Tyr Leu Ala His Phe Pro Glu
            420                 425                 430
Asp His Lys Ile Asn Val Glu Lys Leu Ser Tyr Cys Trp Ala Ala Glu
        435                 440                 445
Gly Ile Ser Thr Ala Glu Asp Tyr His Asn Gly Glu Thr Ile Gln Asp
    450                 455                 460
Val Gly Gln Ser Tyr Leu Glu Glu Leu Val Arg Arg Asn Met Ile Ile
465                 470                 475                 480
Trp Glu Arg Asp Ala Thr Ala Ser Arg Phe Gly Thr Cys His Leu His
                485                 490                 495
Asp Met Met Arg Glu Val Cys Leu Phe Lys Ala Lys Glu Glu Asn Phe
            500                 505                 510
Leu Gln Ile Ala Val Lys Ser Val Gly Val Thr Ser Ser Ser Thr Gly
        515                 520                 525
Asn Ser Gln Ser Pro Cys Arg Ser Arg Arg Leu Val Tyr Gln Cys Pro
    530                 535                 540
Thr Thr Leu His Val Glu Arg Asp Ile Asn Asn Pro Lys Leu Arg Ser
545                 550                 555                 560
Leu Val Val Leu Trp His Asp Leu Trp Val Glu Asn Trp Lys Leu Leu
                565                 570                 575
Gly Thr Ser Phe Thr Arg Leu Lys Leu Leu Arg Val Leu Asp Leu Phe
            580                 585                 590
Tyr Val Asp Phe Glu Gly Met Lys Leu Pro Phe Gly Ile Gly Asn Leu
        595                 600                 605
Ile His Leu Arg Tyr Leu Ser Leu Gln Asp Ala Lys Val Ser His Leu
    610                 615                 620
```

```
Pro Ser Ser Leu Gly Asn Leu Met Leu Leu Ile Tyr Leu Asn Leu Asp
625                 630                 635                 640

Val Asp Thr Glu Phe Ile Phe Val Pro Asp Val Phe Met Arg Met His
            645                 650                 655

Glu Leu Arg Tyr Leu Lys Leu Pro Leu His Met His Lys Lys Thr Arg
            660                 665                 670

Leu Ser Leu Arg Asn Leu Val Lys Leu Glu Thr Leu Val Tyr Phe Ser
        675                 680                 685

Thr Trp His Ser Ser Lys Asp Leu Cys Gly Met Thr Arg Leu Met
690                 695                 700

Thr Leu Ala Ile Arg Leu Thr Arg Val Thr Ser Thr Glu Thr Leu Ser
705                 710                 715                 720

Ala Ser Ile Ser Gly Leu Arg Asn Leu Glu Tyr Leu Tyr Ile Val Gly
                725                 730                 735

Thr His Ser Lys Lys Met Arg Glu Glu Gly Ile Val Leu Asp Phe Ile
                740                 745                 750

His Leu Lys His Leu Leu Leu Asp Leu Tyr Met Pro Arg Gln Gln His
            755                 760                 765

Phe Pro Ser Arg Leu Thr Phe Val Lys Leu Ser Glu Cys Gly Leu Glu
770                 775                 780

Glu Asp Pro Met Pro Ile Leu Glu Lys Leu Leu His Leu Lys Gly Val
785                 790                 795                 800

Ile Leu Leu Lys Gly Ser Tyr Cys Gly Arg Arg Met Val Cys Ser Gly
                805                 810                 815

Gly Gly Phe Pro Gln Leu Lys Lys Leu Glu Ile Val Gly Leu Asn Lys
                820                 825                 830

Trp Glu Glu Trp Leu Val Glu Glu Gly Ser Met Pro Leu Leu Glu Thr
            835                 840                 845

Leu Ser Ile Leu Asp Cys Glu Glu Leu Lys Glu Ile Pro Asp Gly Leu
850                 855                 860

Arg Phe Ile Tyr Ser Leu Glu Leu Val Met Leu Gly Thr Arg Trp Lys
865                 870                 875                 880

Lys Lys Phe Ser Val Gly Gly Glu Asp Tyr Tyr Lys Val Gln His Ile
                885                 890                 895

Pro Ser Val Glu Phe Ile Gly Gly Tyr Leu Lys
            900                 905

<210> SEQ ID NO 36
<211> LENGTH: 842
<212> TYPE: PRT
<213> ORGANISM: Arabidopsis thaliana

<400> SEQUENCE: 36

Met Ala Glu Thr Leu Leu Ser Phe Gly Val Glu Lys Leu Trp Asp Leu
1               5                   10                  15

Leu Val Arg Glu Ser Asp Arg Phe Gln Gly Val Lys Lys Gln Phe Asn
            20                  25                  30

Glu Leu Arg Ser Asp Leu Asn Lys Leu Arg Cys Phe Leu Glu Asp Ala
        35                  40                  45

Asp Ala Lys Lys His Gln Ser Ala Met Val Ser Asn Thr Val Lys Glu
    50                  55                  60

Val Lys Glu Ile Val Tyr Asp Thr Glu Asp Ile Ile Glu Thr Phe Leu
65                  70                  75                  80

Arg Lys Lys Gln Leu Gly Arg Thr Arg Gly Met Lys Lys Arg Ile Lys
                85                  90                  95
```

```
Glu Phe Ala Cys Val Leu Pro Asp Arg Arg Lys Ile Ala Ile Asp Met
                100                 105                 110

Glu Gly Leu Ser Lys Arg Ile Ala Lys Val Ile Cys Asp Met Gln Ser
            115                 120                 125

Leu Gly Val Gln Gln Glu Asn Val Lys Lys Leu Val Gly His Leu Val
        130                 135                 140

Glu Val Glu Asp Ser Ser Gln Val Val Ser Ile Thr Gly Met Gly Gly
145                 150                 155                 160

Ile Gly Lys Thr Thr Leu Ala Arg Gln Val Phe Asn His Glu Thr Val
                165                 170                 175

Lys Ser His Phe Ala Gln Leu Ala Trp Val Cys Val Ser Gln Gln Phe
            180                 185                 190

Thr Arg Lys Tyr Val Trp Gln Thr Ile Leu Arg Lys Val Gly Pro Glu
        195                 200                 205

Tyr Ile Lys Leu Glu Met Thr Glu Asp Glu Leu Gln Glu Lys Leu Phe
    210                 215                 220

Arg Leu Leu Gly Thr Arg Lys Ala Leu Ile Val Leu Asp Asp Ile Trp
225                 230                 235                 240

Arg Glu Glu Asp Trp Asp Met Ile Glu Pro Ile Phe Pro Leu Gly Lys
                245                 250                 255

Gly Trp Lys Val Leu Leu Thr Ser Arg Asn Glu Gly Val Ala Leu Arg
            260                 265                 270

Ala Asn Pro Asn Gly Phe Ile Phe Lys Pro Asp Cys Leu Thr Pro Glu
        275                 280                 285

Glu Ser Trp Thr Ile Phe Arg Arg Ile Val Phe Pro Gly Glu Asn Thr
    290                 295                 300

Thr Glu Tyr Lys Val Asp Glu Lys Met Glu Glu Leu Gly Lys Gln Met
305                 310                 315                 320

Ile Lys His Cys Gly Gly Leu Pro Leu Ala Leu Lys Val Leu Gly Gly
                325                 330                 335

Leu Leu Val Val His Phe Thr Leu Asp Glu Trp Lys Arg Ile Tyr Gly
            340                 345                 350

Asn Ile Lys Ser His Ile Val Gly Gly Thr Ser Phe Asn Asp Lys Asn
        355                 360                 365

Met Ser Ser Val Tyr His Ile Leu His Leu Ser Phe Glu Glu Leu Pro
    370                 375                 380

Ile Tyr Leu Lys His Cys Phe Leu Tyr Leu Ala Gln Phe Pro Glu Asp
385                 390                 395                 400

Phe Thr Ile Asp Leu Glu Lys Leu Ser Tyr Tyr Trp Ala Ala Glu Gly
                405                 410                 415

Met Pro Arg Pro Arg Tyr Tyr Asp Gly Ala Thr Ile Arg Lys Val Gly
            420                 425                 430

Asp Gly Tyr Ile Glu Glu Leu Val Lys Arg Asn Met Val Ile Ser Glu
        435                 440                 445

Arg Asp Ala Arg Thr Arg Arg Phe Glu Thr Cys His Leu His Asp Ile
    450                 455                 460

Val Arg Glu Val Cys Leu Leu Lys Ala Glu Glu Asn Leu Ile Glu
465                 470                 475                 480

Thr Glu Asn Ser Lys Ser Pro Ser Lys Pro Arg Arg Leu Val Val Lys
                485                 490                 495

Gly Gly Asp Lys Thr Asp Met Glu Gly Lys Leu Lys Asn Pro Lys Leu
            500                 505                 510
```

```
Arg Ser Leu Leu Phe Ile Glu Glu Leu Gly Gly Tyr Arg Gly Phe Glu
            515                 520                 525

Val Trp Phe Thr Arg Leu Gln Leu Met Arg Val Leu Asp Leu His Gly
        530                 535                 540

Val Glu Phe Gly Gly Glu Leu Pro Ser Ser Ile Gly Leu Leu Ile His
545                 550                 555                 560

Leu Arg Tyr Leu Ser Leu Tyr Arg Ala Lys Ala Ser His Leu Pro Ser
                565                 570                 575

Ser Met Gln Asn Leu Lys Met Leu Leu Tyr Leu Asn Leu Cys Val Gln
            580                 585                 590

Glu Ser Cys Tyr Ile Tyr Ile Pro Asn Phe Leu Lys Glu Met Leu Glu
        595                 600                 605

Leu Lys Tyr Leu Ser Leu Pro Leu Arg Met Asp Asp Lys Ser Met Gly
    610                 615                 620

Glu Trp Gly Asp Leu Gln Phe Met Thr Arg Leu Arg Ala Leu Ser Ile
625                 630                 635                 640

Tyr Ile Arg Gly Arg Leu Asn Met Lys Thr Leu Ser Ser Ser Leu Ser
                645                 650                 655

Lys Leu Arg Asp Leu Glu Asn Leu Thr Ile Cys Tyr Tyr Pro Met Tyr
            660                 665                 670

Ala Pro Met Ser Gly Ile Glu Gly Leu Val Leu Asp Cys Asp Gln Leu
        675                 680                 685

Lys His Leu Asn Leu Arg Ile Tyr Met Pro Arg Leu Pro Asp Glu Gln
    690                 695                 700

His Phe Pro Trp His Leu Arg Asn Ile Ser Leu Ala Glu Cys Cys Leu
705                 710                 715                 720

Lys Glu Asp Pro Met Pro Ile Leu Glu Lys Leu Leu Gln Leu Asn Glu
                725                 730                 735

Val Ser Leu Ser His Gln Ser Phe Cys Gly Lys Arg Met Val Cys Ser
            740                 745                 750

Asp Gly Gly Phe Pro Gln Leu Gln Lys Leu Asp Leu Cys Gly Leu Glu
        755                 760                 765

Glu Trp Glu Glu Trp Ile Val Glu Gly Ser Met Pro Arg Leu His
    770                 775                 780

Lys Leu Thr Ile Arg Asn Asp Pro Lys Leu Lys Glu Leu Pro Asp Gly
785                 790                 795                 800

Leu Lys Phe Ile Thr Ser Leu Lys Glu Val His Val Ile Leu Asn Asn
                805                 810                 815

Trp Asp Phe Lys Lys Lys Leu Ser Arg Gly Gly Glu Asp Tyr Tyr Lys
            820                 825                 830

Val Gln His Ile Pro Leu Val Arg Phe Leu
        835                 840

<210> SEQ ID NO 37
<211> LENGTH: 906
<212> TYPE: PRT
<213> ORGANISM: Arabidopsis thaliana

<400> SEQUENCE: 37

Met Gln Asp Leu Tyr Met Val Asp Ser Ile Val Ser Phe Gly Val Glu
1               5                   10                  15

Lys Leu Trp Lys Leu Leu Ser Gln Glu Tyr Glu Arg Phe Gln Gly Val
            20                  25                  30

Glu Glu Gln Ile Thr Glu Leu Arg Asp Asp Leu Lys Met Leu Met Ala
        35                  40                  45
```

```
Phe Leu Ser Asp Ala Asp Ala Lys Lys Gln Thr Arg Ala Leu Ala Arg
    50                  55                  60

Asn Cys Leu Glu Glu Ile Lys Glu Ile Thr Tyr Asp Ala Glu Asp Ile
 65                  70                  75                  80

Ile Glu Ile Phe Leu Leu Lys Gly Ser Val Asn Met Arg Ser Leu Ala
                 85                  90                  95

Cys Phe Pro Gly Gly Arg Arg Glu Ile Ala Leu Gln Ile Thr Ser Ile
            100                 105                 110

Ser Lys Arg Ile Ser Lys Val Ile Gln Val Met Gln Asn Leu Gly Ile
        115                 120                 125

Lys Ser Asp Ile Met Asp Gly Val Asp Ser His Ala Gln Leu Glu Arg
130                 135                 140

Lys Arg Glu Leu Arg His Thr Phe Ser Ser Glu Ser Glu Ser Asn Leu
145                 150                 155                 160

Val Gly Leu Glu Lys Asn Val Glu Lys Leu Val Glu Glu Leu Val Gly
                165                 170                 175

Asn Asp Ser Ser His Gly Val Ser Ile Thr Gly Leu Gly Gly Leu Gly
            180                 185                 190

Lys Thr Thr Leu Ala Arg Gln Ile Phe Asp His Asp Lys Val Lys Ser
        195                 200                 205

His Phe Asp Gly Leu Ala Trp Val Cys Val Ser Gln Glu Phe Thr Arg
210                 215                 220

Lys Asp Val Trp Lys Thr Ile Leu Gly Asn Leu Ser Pro Lys Tyr Lys
225                 230                 235                 240

Asp Ser Asp Leu Pro Glu Asp Ile Gln Lys Lys Leu Phe Gln Leu
                245                 250                 255

Leu Glu Thr Lys Lys Ala Leu Ile Val Phe Asp Asp Leu Trp Lys Arg
            260                 265                 270

Glu Asp Trp Tyr Arg Ile Ala Pro Met Phe Pro Glu Arg Lys Ala Gly
        275                 280                 285

Trp Lys Val Leu Leu Thr Ser Arg Asn Asp Ala Ile His Pro His Cys
290                 295                 300

Val Thr Phe Lys Pro Glu Leu Leu Thr His Asp Glu Cys Trp Lys Leu
305                 310                 315                 320

Leu Gln Arg Ile Ala Phe Ser Lys Gln Lys Thr Ile Thr Gly Tyr Ile
                325                 330                 335

Ile Asp Lys Glu Met Val Lys Met Ala Lys Glu Met Thr Lys His Cys
            340                 345                 350

Lys Arg Leu Pro Leu Ala Val Lys Leu Leu Gly Gly Leu Leu Asp Ala
        355                 360                 365

Lys His Thr Leu Arg Gln Trp Lys Leu Ile Ser Glu Asn Ile Ile Ser
370                 375                 380

His Ile Val Val Gly Gly Thr Ser Ser Asn Glu Asn Asp Ser Ser Ser
385                 390                 395                 400

Val Asn His Val Leu Ser Leu Ser Phe Glu Gly Leu Pro Gly Tyr Leu
                405                 410                 415

Lys His Cys Leu Leu Tyr Leu Ala Ser Tyr Pro Glu Asp His Glu Ile
            420                 425                 430

Glu Ile Glu Arg Leu Ser Tyr Val Trp Ala Ala Glu Gly Ile Thr Tyr
        435                 440                 445

Pro Gly Asn Tyr Glu Gly Ala Thr Ile Arg Asp Val Ala Asp Leu Tyr
450                 455                 460
```

```
Ile Glu Glu Leu Val Lys Arg Asn Met Val Ile Ser Glu Arg Asp Ala
465                 470                 475                 480

Leu Thr Ser Arg Phe Glu Lys Cys Gln Leu His Asp Leu Met Arg Glu
            485                 490                 495

Ile Cys Leu Leu Lys Ala Lys Glu Glu Asn Phe Leu Gln Ile Val Thr
        500                 505                 510

Asp Pro Thr Ser Ser Ser Val His Ser Leu Ala Ser Ser Arg Ser
        515                 520                 525

Arg Arg Leu Val Val Tyr Asn Thr Ser Ile Phe Ser Gly Glu Asn Asp
    530                 535                 540

Met Lys Asn Ser Lys Leu Arg Ser Leu Phe Ile Pro Val Gly Tyr
545                 550                 555                 560

Ser Arg Phe Ser Met Gly Ser Asn Phe Ile Glu Leu Pro Leu Leu Arg
            565                 570                 575

Val Leu Asp Leu Asp Gly Ala Lys Phe Lys Gly Lys Leu Pro Ser
        580                 585                 590

Ser Ile Gly Lys Leu Ile His Leu Lys Tyr Leu Ser Leu Tyr Gln Ala
    595                 600                 605

Ser Val Thr Tyr Leu Pro Ser Ser Leu Arg Asn Leu Lys Ser Leu Leu
    610                 615                 620

Tyr Leu Asn Leu Arg Ile Asn Ser Gly Gln Leu Ile Asn Val Pro Asn
625                 630                 635                 640

Val Phe Lys Glu Met Leu Glu Leu Arg Tyr Leu Ser Leu Pro Trp Glu
            645                 650                 655

Arg Ser Ser Leu Thr Lys Leu Glu Leu Gly Asn Leu Leu Lys Leu Glu
        660                 665                 670

Thr Leu Ile Asn Phe Ser Thr Lys Asp Ser Ser Val Thr Asp Leu His
        675                 680                 685

Arg Met Thr Lys Leu Arg Thr Leu Gln Ile Leu Ile Ser Gly Glu Gly
    690                 695                 700

Leu His Met Glu Thr Leu Ser Ser Ala Leu Ser Met Leu Gly His Leu
705                 710                 715                 720

Glu Asp Leu Thr Val Thr Pro Ser Glu Asn Ser Val Gln Phe Lys His
            725                 730                 735

Pro Lys Leu Ile Tyr Arg Pro Met Leu Pro Asp Val Gln His Phe Pro
        740                 745                 750

Ser His Leu Thr Thr Ile Ser Leu Val Tyr Cys Phe Leu Glu Glu Asp
        755                 760                 765

Pro Met Pro Thr Leu Glu Lys Leu Leu Gln Leu Lys Val Val Ser Leu
770                 775                 780

Trp Tyr Asn Ala Tyr Val Gly Arg Arg Met Val Cys Thr Gly Gly Gly
785                 790                 795                 800

Phe Pro Pro Leu His Arg Leu Glu Ile Trp Gly Leu Asp Ala Leu Glu
            805                 810                 815

Glu Trp Ile Val Glu Gly Ser Met Pro Leu Leu His Thr Leu His
        820                 825                 830

Ile Val Asp Cys Lys Lys Leu Lys Glu Ile Pro Asp Gly Leu Arg Phe
        835                 840                 845

Ile Ser Ser Leu Lys Glu Leu Ala Ile Arg Thr Asn Glu Lys Val Phe
    850                 855                 860

Gln Lys Lys Val Ser Lys Gly Gly Glu Asp Tyr Tyr Lys Met Gln His
865                 870                 875                 880

Val Pro Leu Ile Arg Tyr Asn Trp Pro Gln Glu Pro Glu Asn Asn Glu
```

```
                            885                 890                 895
Val Ile Tyr Ser Phe Pro Ser Pro Ile Ile
            900                 905

<210> SEQ ID NO 38
<211> LENGTH: 906
<212> TYPE: PRT
<213> ORGANISM: Arabidopsis thaliana

<400> SEQUENCE: 38

Met Ala Glu Ala Val Ser Phe Gly Val Glu Lys Leu Trp Glu Leu
1               5                   10                  15

Leu Ser Arg Glu Ser Ala Arg Leu Asn Gly Ile Asp Glu Gln Val Asp
            20                  25                  30

Gly Leu Lys Arg Gln Leu Gly Arg Leu Gln Ser Leu Leu Lys Asp Ala
        35                  40                  45

Asp Ala Lys Lys Asn Glu Thr Glu Arg Val Arg Asn Phe Leu Glu Asp
    50                  55                  60

Val Lys Asp Ile Val Tyr Asp Ala Asp Ile Ile Glu Ser Phe Leu
65                  70                  75                  80

Leu Asn Glu Leu Arg Gly Lys Lys Gly Ile Lys Lys Gln Val Arg
            85                  90                  95

Thr Leu Ala Cys Phe Leu Val Asp Arg Arg Lys Phe Ala Ser Asp Ile
        100                 105                 110

Glu Gly Ile Thr Lys Arg Ile Ser Glu Val Ile Val Gly Met Gln Ser
    115                 120                 125

Leu Gly Ile Gln His Ile Ala Asp Gly Gly Arg Ser Leu Ser Leu
        130                 135                 140

Gln Glu Arg Gln Arg Glu Ile Arg Gln Thr Phe Ser Arg Asn Ser Glu
145                 150                 155                 160

Ser Asp Leu Val Gly Leu Asp Gln Ser Val Glu Leu Val Asp His
            165                 170                 175

Leu Val Glu Asn Asp Ser Val Gln Val Val Ser Val Ser Gly Met Gly
        180                 185                 190

Gly Ile Gly Lys Thr Thr Leu Ala Arg Gln Val Phe His His Asp Ile
    195                 200                 205

Val Arg Arg His Phe Asp Gly Phe Ser Trp Val Cys Val Ser Gln Gln
    210                 215                 220

Phe Thr Arg Lys Asp Val Trp Gln Arg Ile Leu Gln Asp Leu Arg Pro
225                 230                 235                 240

Tyr Asp Glu Gly Ile Ile Gln Met Asp Glu Tyr Thr Leu Gln Gly Glu
            245                 250                 255

Leu Phe Glu Leu Leu Glu Ser Gly Arg Tyr Leu Leu Val Leu Asp Asp
        260                 265                 270

Val Trp Lys Glu Glu Asp Trp Asp Arg Ile Lys Ala Val Phe Pro His
    275                 280                 285

Lys Arg Gly Trp Lys Met Leu Leu Thr Ser Arg Asn Glu Gly Leu Gly
    290                 295                 300

Leu His Ala Asp Pro Thr Cys Phe Ala Phe Arg Pro Arg Ile Leu Thr
305                 310                 315                 320

Pro Glu Gln Ser Trp Lys Leu Phe Glu Arg Ile Val Ser Ser Arg Arg
            325                 330                 335

Asp Lys Thr Glu Phe Lys Val Asp Glu Ala Met Gly Lys Glu Met Val
        340                 345                 350
```

```
Thr Tyr Cys Gly Gly Leu Pro Leu Ala Val Lys Val Leu Gly Gly Leu
            355                 360                 365

Leu Ala Lys Lys His Thr Val Leu Glu Trp Lys Arg Val His Ser Asn
370                 375                 380

Ile Val Thr His Ile Val Gly Lys Ser Gly Leu Ser Asp Asp Asn Ser
385                 390                 395                 400

Asn Ser Val Tyr Arg Val Leu Ser Leu Ser Tyr Glu Asp Leu Pro Met
                405                 410                 415

Gln Leu Lys His Cys Phe Phe Tyr Leu Ala His Phe Pro Glu Asp Tyr
                420                 425                 430

Lys Ile Asp Val Lys Ile Leu Phe Asn Tyr Trp Val Ala Glu Gly Ile
            435                 440                 445

Ile Thr Pro Phe His Asp Gly Ser Thr Ile Gln Asp Thr Gly Glu Ser
450                 455                 460

Tyr Leu Glu Glu Leu Val Arg Arg Asn Met Val Val Glu Glu Ser
465                 470                 475                 480

Tyr Leu Thr Ser Arg Ile Glu Tyr Cys Gln Met His Asp Met Met Arg
                485                 490                 495

Glu Val Cys Leu Ser Lys Ala Lys Glu Glu Asn Phe Ile Arg Val Val
            500                 505                 510

Lys Val Pro Thr Thr Thr Ser Thr Thr Ile Asn Ala Gln Ser Pro Cys
                515                 520                 525

Arg Ser Arg Arg Leu Val Leu His Ser Gly Asn Ala Leu His Met Leu
            530                 535                 540

Gly His Lys Asp Asn Lys Lys Ala Arg Ser Val Leu Ile Phe Gly Val
545                 550                 555                 560

Glu Glu Lys Phe Trp Lys Pro Arg Gly Phe Gln Cys Leu Pro Leu Leu
                565                 570                 575

Arg Val Leu Asp Leu Ser Tyr Val Gln Phe Glu Gly Gly Lys Leu Pro
                580                 585                 590

Ser Ser Ile Gly Asp Leu Ile His Leu Arg Phe Leu Ser Leu Tyr Glu
            595                 600                 605

Ala Gly Val Ser His Leu Pro Ser Ser Leu Gly Asn Leu Lys Leu Leu
610                 615                 620

Leu Cys Leu Asn Leu Gly Val Ala Asp Arg Leu Leu His Val Pro
625                 630                 635                 640

Asn Val Leu Lys Glu Met Gln Glu Leu Arg Tyr Leu Arg Leu Pro Arg
                645                 650                 655

Ser Met Pro Ala Lys Thr Lys Leu Glu Leu Gly Asp Leu Val Asn Leu
                660                 665                 670

Glu Ser Leu Thr Asn Phe Ser Thr Lys His Gly Ser Val Thr Asp Leu
            675                 680                 685

Leu Arg Met Thr Lys Leu Ser Val Leu Asn Val Ile Phe Ser Gly Glu
690                 695                 700

Cys Thr Phe Glu Thr Leu Leu Leu Ser Leu Arg Glu Leu Arg Asn Leu
705                 710                 715                 720

Glu Thr Leu Ser Phe His Asp Phe Gln Lys Val Ser Val Ala Asn His
                725                 730                 735

Gly Gly Glu Leu Leu Val Leu Asp Phe Ile His Leu Lys Asp Leu Thr
                740                 745                 750

Leu Ser Met His Leu Pro Arg Phe Pro Asp Gln Tyr Arg Phe Pro Pro
            755                 760                 765

His Leu Ala His Ile Trp Leu Ile Gly Cys Arg Met Glu Glu Asp Pro
```

```
            770                 775                 780
Met Pro Ile Leu Glu Lys Leu Leu His Leu Lys Ser Val Tyr Leu Ser
785                 790                 795                 800

Ser Gly Ala Phe Leu Gly Arg Arg Met Val Cys Ser Lys Gly Gly Phe
                805                 810                 815

Pro Gln Leu Leu Ala Leu Lys Met Ser Tyr Lys Lys Glu Leu Val Glu
                820                 825                 830

Trp Arg Val Glu Glu Gly Ser Met Pro Cys Leu Arg Thr Leu Thr Ile
            835                 840                 845

Asp Asn Cys Lys Lys Leu Lys Gln Leu Pro Asp Gly Leu Lys Tyr Val
        850                 855                 860

Thr Cys Leu Lys Glu Leu Lys Ile Glu Arg Met Lys Arg Glu Trp Thr
865                 870                 875                 880

Glu Arg Leu Val Ile Gly Gly Asp Tyr Tyr Lys Val Gln His Ile
                885                 890                 895

Pro Ser Val Gln Phe Ile Asn Cys Asp His
                900                 905

<210> SEQ ID NO 39
<211> LENGTH: 906
<212> TYPE: PRT
<213> ORGANISM: Arabidopsis thaliana

<400> SEQUENCE: 39

Met Ala Glu Ala Val Val Ser Phe Gly Val Glu Lys Leu Trp Glu Leu
1               5                   10                  15

Leu Ser Arg Glu Ser Ala Arg Leu Asn Gly Ile Asp Glu Gln Val Asp
                20                  25                  30

Gly Leu Lys Arg Gln Leu Gly Arg Leu Gln Ser Leu Leu Lys Asp Ala
            35                  40                  45

Asp Ala Lys Lys Asn Glu Thr Glu Arg Val Arg Asn Phe Leu Glu Asp
        50                  55                  60

Val Lys Asp Ile Val Tyr Asp Ala Asp Ile Ile Glu Ser Phe Leu
65                  70                  75                  80

Leu Asn Glu Leu Arg Gly Lys Gly Lys Gly Ile Lys Lys Gln Val Arg
                85                  90                  95

Thr Leu Ala Cys Phe Leu Val Asp Arg Arg Lys Phe Ala Ser Asp Ile
            100                 105                 110

Glu Gly Ile Thr Lys Arg Ile Ser Glu Val Ile Val Gly Met Gln Ser
        115                 120                 125

Leu Gly Ile Gln His Ile Ala Asp Gly Gly Arg Ser Leu Ser Leu
    130                 135                 140

Gln Glu Arg Gln Arg Glu Ile Arg Gln Thr Phe Ser Arg Asn Ser Glu
145                 150                 155                 160

Ser Asp Leu Val Gly Leu Asp Gln Ser Val Glu Leu Val Asp His
                165                 170                 175

Leu Val Glu Asn Asp Ser Val Gln Val Val Ser Val Ser Gly Met Gly
            180                 185                 190

Gly Ile Gly Lys Thr Thr Leu Ala Arg Gln Val Phe His His Asp Ile
        195                 200                 205

Val Arg Arg His Phe Asp Gly Phe Ser Trp Val Cys Val Ser Gln Gln
    210                 215                 220

Phe Thr Arg Lys Asp Val Trp Gln Arg Ile Leu Gln Asp Leu Arg Pro
225                 230                 235                 240
```

```
Tyr Asp Glu Gly Ile Ile Gln Met Asp Glu Tyr Thr Leu Gln Gly Glu
            245                 250                 255

Leu Phe Glu Leu Leu Glu Ser Gly Arg Tyr Leu Leu Val Leu Asp Asp
        260                 265                 270

Val Trp Lys Glu Glu Asp Trp Asp Arg Ile Lys Ala Val Phe Pro His
        275                 280                 285

Lys Arg Gly Trp Lys Met Leu Leu Thr Ser Arg Asn Glu Gly Leu Gly
        290                 295                 300

Leu His Ala Asp Pro Thr Cys Phe Ala Phe Pro Arg Ile Leu Thr
305                 310                 315                 320

Pro Glu Gln Ser Trp Lys Leu Phe Glu Arg Ile Val Ser Ser Arg Arg
                325                 330                 335

Asp Lys Thr Glu Phe Lys Val Asp Glu Ala Met Gly Lys Glu Met Val
            340                 345                 350

Thr Tyr Cys Gly Gly Leu Pro Leu Ala Val Lys Val Leu Gly Gly Leu
        355                 360                 365

Leu Ala Lys Lys His Thr Val Leu Glu Trp Lys Arg Val His Ser Asn
370                 375                 380

Ile Val Thr His Ile Val Gly Lys Ser Gly Leu Ser Asp Asp Asn Ser
385                 390                 395                 400

Asn Ser Val Tyr Arg Val Leu Ser Leu Ser Tyr Glu Asp Leu Pro Met
            405                 410                 415

Gln Leu Lys His Cys Phe Phe Tyr Leu Ala His Phe Pro Glu Asp Tyr
            420                 425                 430

Lys Ile Asp Val Lys Ile Leu Phe Asn Tyr Trp Val Ala Glu Gly Ile
        435                 440                 445

Ile Thr Pro Phe His Asp Gly Ser Thr Ile Gln Asp Thr Gly Glu Ser
        450                 455                 460

Tyr Leu Glu Glu Leu Val Arg Arg Asn Met Val Val Glu Glu Ser
465                 470                 475                 480

Tyr Leu Thr Ser Arg Ile Glu Tyr Cys Gln Met His Asp Met Met Arg
            485                 490                 495

Glu Val Cys Leu Ser Lys Ala Lys Glu Glu Asn Phe Ile Arg Val Val
                500                 505                 510

Lys Val Pro Thr Thr Thr Ser Thr Thr Ile Asn Ala Gln Ser Pro Cys
        515                 520                 525

Arg Ser Arg Arg Leu Val Leu His Ser Gly Asn Ala Leu His Met Leu
        530                 535                 540

Gly His Lys Asp Asn Lys Lys Ala Arg Ser Val Leu Ile Phe Gly Val
545                 550                 555                 560

Glu Glu Lys Phe Trp Lys Pro Arg Gly Phe Gln Cys Leu Pro Leu Leu
                565                 570                 575

Arg Val Leu Asp Leu Ser Tyr Val Gln Phe Glu Gly Gly Lys Leu Pro
            580                 585                 590

Ser Ser Ile Gly Asp Leu Ile His Leu Arg Phe Leu Ser Leu Tyr Glu
        595                 600                 605

Ala Gly Val Ser His Leu Pro Ser Ser Leu Gly Asn Leu Lys Leu Leu
        610                 615                 620

Leu Cys Leu Asn Leu Gly Val Ala Asp Arg Leu Val His Val Pro
625                 630                 635                 640

Asn Val Leu Lys Glu Met Gln Glu Leu Arg Tyr Leu Arg Leu Pro Arg
                645                 650                 655

Ser Met Pro Ala Lys Thr Lys Leu Glu Leu Gly Asp Leu Val Asn Leu
```

```
              660                 665                 670
Glu Ser Leu Thr Asn Phe Ser Thr Lys His Gly Ser Val Thr Asp Leu
            675                 680                 685

Leu Arg Met Thr Lys Leu Ser Val Leu Asn Val Ile Phe Ser Gly Glu
        690                 695                 700

Cys Thr Phe Glu Thr Leu Leu Leu Ser Leu Arg Glu Leu Arg Asn Leu
705                 710                 715                 720

Glu Thr Leu Ser Phe His Asp Phe Gln Lys Val Ser Val Ala Asn His
                725                 730                 735

Gly Gly Glu Leu Leu Val Leu Asp Phe Ile His Leu Lys Asp Leu Thr
            740                 745                 750

Leu Ser Met His Leu Pro Arg Phe Pro Asp Gln Tyr Arg Phe Pro Pro
        755                 760                 765

His Leu Ala His Ile Trp Leu Ile Gly Cys Arg Met Glu Glu Asp Pro
    770                 775                 780

Met Pro Ile Leu Glu Lys Leu Leu His Leu Lys Ser Val Tyr Leu Ser
785                 790                 795                 800

Ser Gly Ala Phe Leu Gly Arg Arg Met Val Cys Ser Lys Gly Gly Phe
                805                 810                 815

Pro Gln Leu Leu Ala Leu Lys Met Ser Tyr Lys Lys Glu Leu Val Glu
            820                 825                 830

Trp Arg Val Glu Glu Gly Ser Met Pro Cys Leu Arg Thr Leu Thr Ile
        835                 840                 845

Asp Asn Cys Lys Lys Leu Lys Gln Leu Pro Asp Gly Leu Lys Tyr Val
    850                 855                 860

Thr Cys Leu Lys Glu Leu Lys Ile Glu Arg Met Lys Arg Glu Trp Thr
865                 870                 875                 880

Glu Arg Leu Val Ile Gly Gly Asp Tyr Tyr Lys Val Gln His Ile
                885                 890                 895

Pro Ser Val Gln Phe Ile Asn Cys Asp His
            900                 905

<210> SEQ ID NO 40
<211> LENGTH: 908
<212> TYPE: PRT
<213> ORGANISM: Arabidopsis thaliana

<400> SEQUENCE: 40

Met Ala Glu Ala Phe Val Ser Phe Gly Leu Glu Lys Leu Trp Asp Leu
1               5                   10                  15

Leu Ser Arg Glu Ser Glu Arg Leu Gln Gly Ile Asp Gly Gln Leu Asp
            20                  25                  30

Gly Leu Lys Arg Gln Leu Arg Ser Leu Gln Ser Leu Leu Lys Asp Ala
        35                  40                  45

Asp Ala Lys Lys His Gly Ser Asp Arg Val Arg Asn Phe Leu Glu Asp
    50                  55                  60

Val Lys Asp Leu Val Phe Asp Ala Glu Asp Ile Ile Glu Ser Tyr Val
65                  70                  75                  80

Leu Asn Lys Leu Ser Gly Lys Gly Lys Gly Val Lys Lys His Val Arg
                85                  90                  95

Arg Leu Ala Cys Phe Leu Thr Asp Arg His Lys Val Ala Ser Asp Ile
            100                 105                 110

Glu Gly Ile Thr Lys Arg Ile Ser Glu Val Ile Gly Met Gln Ser
        115                 120                 125
```

```
Phe Gly Ile Gln Gln Ile Ile Asp Gly Gly Arg Ser Leu Ser Leu Gln
    130                 135                 140
Glu Arg Gln Arg Val Gln Arg Glu Ile Arg Gln Thr Tyr Pro Asp Ser
145                 150                 155                 160
Ser Glu Ser Asp Leu Val Gly Val Gln Ser Val Lys Glu Leu Val
                165                 170                 175
Gly His Leu Val Glu Asn Asp Val His Gln Val Ser Ile Ala Gly
                180                 185                 190
Met Gly Gly Ile Gly Lys Thr Thr Leu Ala Arg Gln Val Phe His His
        195                 200                 205
Asp Leu Val Arg Arg His Phe Asp Gly Phe Ala Trp Val Cys Val Ser
    210                 215                 220
Gln Gln Phe Thr Gln Lys His Val Trp Gln Arg Ile Leu Gln Glu Leu
225                 230                 235                 240
Gln Pro His Asp Gly Asp Ile Leu Gln Met Asp Glu Tyr Ala Leu Gln
                245                 250                 255
Arg Lys Leu Phe Gln Leu Leu Glu Ala Gly Arg Tyr Leu Val Val Leu
            260                 265                 270
Asp Asp Val Trp Lys Lys Glu Asp Trp Asp Val Ile Lys Ala Val Phe
        275                 280                 285
Pro Arg Lys Arg Gly Trp Lys Met Leu Leu Thr Ser Arg Asn Glu Gly
    290                 295                 300
Val Gly Ile His Ala Asp Pro Thr Cys Leu Thr Phe Arg Ala Ser Ile
305                 310                 315                 320
Leu Asn Pro Glu Glu Ser Trp Lys Leu Cys Glu Arg Ile Val Phe Pro
                325                 330                 335
Arg Arg Asp Glu Thr Glu Val Arg Leu Asp Glu Glu Met Glu Ala Met
            340                 345                 350
Gly Lys Glu Met Val Thr His Cys Gly Gly Leu Pro Leu Ala Val Lys
        355                 360                 365
Ala Leu Gly Gly Leu Leu Ala Asn Lys His Thr Val Pro Glu Trp Lys
    370                 375                 380
Arg Val Phe Asp Asn Ile Gly Ser Gln Ile Val Gly Gly Ser Trp Leu
385                 390                 395                 400
Asp Asp Asn Ser Leu Asn Ser Val Tyr Arg Ile Leu Ser Leu Ser Tyr
                405                 410                 415
Glu Asp Leu Pro Thr His Leu Lys His Cys Phe Leu Asn Leu Ala His
            420                 425                 430
Phe Pro Glu Asp Ser Glu Ile Ser Thr Tyr Ser Leu Phe Tyr Tyr Trp
        435                 440                 445
Ala Ala Glu Gly Ile Tyr Asp Gly Ser Thr Ile Glu Asp Ser Gly Glu
    450                 455                 460
Tyr Tyr Leu Glu Glu Leu Val Arg Arg Asn Leu Val Ile Ala Asp Asp
465                 470                 475                 480
Asn Tyr Leu Ser Trp Gln Ser Lys Tyr Cys Gln Met His Asp Met Met
                485                 490                 495
Arg Glu Val Cys Leu Ser Lys Ala Lys Glu Glu Asn Phe Leu Gln Ile
            500                 505                 510
Ile Ile Asp Pro Thr Cys Thr Ser Thr Ile Asn Ala Gln Ser Pro Ser
        515                 520                 525
Arg Ser Arg Arg Leu Ser Ile His Ser Gly Lys Ala Phe His Ile Leu
    530                 535                 540
Gly His Lys Asn Lys Thr Lys Val Arg Ser Leu Ile Val Pro Arg Phe
```

```
                545                 550                 555                 560
Glu Glu Asp Tyr Trp Ile Arg Ser Ala Ser Val Phe His Asn Leu Thr
                565                 570                 575
Leu Leu Arg Val Leu Asp Leu Ser Trp Val Lys Phe Glu Gly Gly Lys
                580                 585                 590
Leu Pro Cys Ser Ile Gly Gly Leu Ile His Leu Arg Tyr Leu Ser Leu
                595                 600                 605
Tyr Glu Ala Lys Val Ser His Leu Pro Ser Thr Met Arg Asn Leu Lys
                610                 615                 620
Leu Leu Leu Tyr Leu Asn Leu Arg Val Asp Thr Glu Glu Pro Ile His
625                 630                 635                 640
Val Pro Asn Val Leu Lys Glu Met Ile Gln Leu Arg Tyr Leu Ser Leu
                645                 650                 655
Pro Leu Lys Met Asp Asp Lys Thr Lys Leu Glu Leu Gly Asp Leu Val
                660                 665                 670
Asn Leu Glu Tyr Leu Tyr Gly Phe Ser Thr Gln His Ser Ser Val Thr
                675                 680                 685
Asp Leu Leu Arg Met Thr Lys Leu Arg Tyr Leu Ala Val Ser Leu Ser
                690                 695                 700
Glu Arg Cys Asn Phe Glu Thr Leu Ser Ser Ser Leu Arg Glu Leu Arg
705                 710                 715                 720
Asn Leu Glu Thr Leu Asn Phe Leu Phe Ser Leu Glu Thr Tyr Met Val
                725                 730                 735
Asp Tyr Met Gly Glu Phe Val Leu Asp His Phe Ile His Leu Lys Gln
                740                 745                 750
Leu Gly Leu Ala Val Arg Met Ser Lys Ile Pro Asp Gln His Gln Phe
                755                 760                 765
Pro Pro His Leu Val His Leu Phe Leu Ile Tyr Cys Gly Met Glu Glu
                770                 775                 780
Asp Pro Met Pro Ile Leu Glu Lys Leu Leu His Leu Lys Ser Val Arg
785                 790                 795                 800
Leu Ala Arg Lys Ala Phe Leu Gly Ser Arg Met Val Cys Ser Lys Gly
                805                 810                 815
Gly Phe Pro Gln Leu Cys Val Ile Glu Ile Ser Lys Glu Ser Glu Leu
                820                 825                 830
Glu Glu Trp Ile Val Glu Gly Ser Met Pro Cys Leu Arg Thr Leu
                835                 840                 845
Thr Ile Asp Asp Cys Lys Lys Leu Lys Glu Leu Pro Asp Gly Leu Lys
850                 855                 860
Tyr Ile Thr Ser Leu Lys Glu Leu Lys Ile Glu Gly Met Lys Arg Glu
865                 870                 875                 880
Trp Lys Glu Lys Leu Val Pro Gly Gly Glu Asp Tyr Tyr Lys Val Gln
                885                 890                 895
His Ile Pro Asp Val Gln Phe Ile Asn Cys Asp Gln
                900                 905

<210> SEQ ID NO 41
<211> LENGTH: 908
<212> TYPE: PRT
<213> ORGANISM: Arabidopsis thaliana

<400> SEQUENCE: 41

Met Ala Glu Gly Phe Val Ser Phe Gly Leu Glu Lys Leu Trp Asp Leu
1               5                   10                  15
```

```
Leu Ser Arg Glu Ser Glu Arg Leu Gln Gly Ile Asp Glu Gln Leu Asp
             20                  25                  30

Gly Leu Lys Arg Gln Leu Arg Ser Leu Gln Ser Leu Leu Lys Asp Ala
         35                  40                  45

Asp Ala Lys Lys His Gly Ser Asp Arg Val Arg Asn Phe Leu Glu Asp
     50                  55                  60

Val Lys Asp Leu Val Phe Asp Ala Glu Asp Ile Ile Glu Ser Tyr Val
 65                  70                  75                  80

Leu Asn Lys Leu Arg Gly Glu Gly Lys Gly Val Lys Lys His Val Arg
                 85                  90                  95

Arg Leu Ala Arg Phe Leu Thr Asp Arg His Lys Val Ala Ser Asp Ile
            100                 105                 110

Glu Gly Ile Thr Lys Arg Ile Ser Asp Val Ile Gly Glu Met Gln Ser
        115                 120                 125

Phe Gly Ile Gln Gln Ile Ile Asp Gly Val Arg Ser Leu Ser Leu Gln
    130                 135                 140

Glu Arg Gln Arg Val Gln Arg Glu Ile Arg Gln Thr Tyr Pro Asp Ser
145                 150                 155                 160

Ser Glu Ser Asp Leu Val Gly Val Gln Ser Val Glu Glu Leu Val
                165                 170                 175

Gly His Leu Val Glu Asn Asp Ile Tyr Gln Val Val Ser Ile Ala Gly
            180                 185                 190

Met Gly Gly Ile Gly Lys Thr Thr Leu Ala Arg Gln Val Phe His His
        195                 200                 205

Asp Leu Val Arg Arg His Phe Asp Gly Phe Ala Trp Val Cys Val Ser
    210                 215                 220

Gln Gln Phe Thr Leu Lys His Val Trp Gln Arg Ile Leu Gln Glu Leu
225                 230                 235                 240

Gln Pro His Asp Gly Asn Ile Leu Gln Met Asp Glu Ser Ala Leu Gln
                245                 250                 255

Pro Lys Leu Phe Gln Leu Leu Glu Thr Gly Arg Tyr Leu Leu Val Leu
            260                 265                 270

Asp Asp Val Trp Lys Lys Glu Asp Trp Asp Arg Ile Lys Ala Val Phe
    275                 280                 285

Pro Arg Lys Arg Gly Trp Lys Met Leu Leu Thr Ser Arg Asn Glu Gly
290                 295                 300

Val Gly Ile His Ala Asp Pro Thr Cys Leu Thr Phe Arg Ala Ser Ile
305                 310                 315                 320

Leu Asn Pro Glu Glu Ser Trp Lys Leu Cys Glu Arg Ile Val Phe Pro
                325                 330                 335

Arg Arg Asp Glu Thr Glu Val Arg Leu Asp Glu Glu Met Glu Ala Met
            340                 345                 350

Gly Lys Glu Met Val Thr His Cys Gly Gly Leu Pro Leu Ala Val Lys
        355                 360                 365

Ala Leu Gly Gly Leu Leu Ala Asn Lys His Thr Val Pro Glu Trp Lys
    370                 375                 380

Arg Val Ser Asp Asn Ile Gly Ser Gln Ile Val Gly Gly Ser Cys Leu
385                 390                 395                 400

Asp Asp Asn Ser Leu Asn Ser Val Asn Arg Ile Leu Ser Leu Ser Tyr
                405                 410                 415

Glu Asp Leu Pro Thr His Leu Lys His Arg Phe Leu Tyr Leu Ala His
            420                 425                 430

Phe Pro Glu Asp Ser Lys Ile Tyr Thr Gln Asp Leu Phe Asn Tyr Trp
```

```
                435                 440                 445
Ala Ala Glu Gly Ile Tyr Asp Gly Ser Thr Ile Gln Asp Ser Gly Glu
450                 455                 460

Tyr Tyr Leu Glu Glu Leu Val Arg Arg Asn Leu Val Ile Ala Asp Asn
465                 470                 475                 480

Arg Tyr Leu Ser Leu Glu Phe Asn Phe Cys Gln Met His Asp Met Met
                485                 490                 495

Arg Glu Val Cys Leu Ser Lys Ala Lys Glu Glu Asn Phe Leu Gln Ile
                500                 505                 510

Ile Lys Asp Pro Thr Ser Thr Ser Thr Ile Asn Ala Gln Ser Pro Ser
                515                 520                 525

Arg Ser Arg Arg Phe Ser Ile His Ser Gly Lys Ala Phe His Ile Leu
                530                 535                 540

Gly His Arg Asn Asn Pro Lys Val Arg Ser Leu Ile Val Ser Arg Phe
545                 550                 555                 560

Glu Glu Asp Phe Trp Ile Arg Ser Ala Ser Val Phe His Asn Leu Thr
                565                 570                 575

Leu Leu Arg Val Leu Asp Leu Ser Arg Val Lys Phe Glu Gly Gly Lys
                580                 585                 590

Leu Pro Ser Ser Ile Gly Gly Leu Ile His Leu Arg Tyr Leu Ser Leu
                595                 600                 605

Tyr Gly Ala Val Val Ser His Leu Pro Ser Thr Met Arg Asn Leu Lys
610                 615                 620

Leu Leu Leu Phe Leu Asn Leu Arg Val Asp Asn Lys Glu Pro Ile His
625                 630                 635                 640

Val Pro Asn Val Leu Lys Glu Met Leu Glu Leu Arg Tyr Leu Ser Leu
                645                 650                 655

Pro Gln Glu Met Asp Asp Lys Thr Lys Leu Glu Leu Gly Asp Leu Val
                660                 665                 670

Asn Leu Glu Tyr Leu Trp Tyr Phe Ser Thr Gln His Ser Ser Val Thr
                675                 680                 685

Asp Leu Leu Arg Met Thr Lys Leu Arg Asn Leu Gly Val Ser Leu Ser
                690                 695                 700

Glu Arg Cys Asn Phe Glu Thr Leu Ser Ser Ser Leu Arg Glu Leu Arg
705                 710                 715                 720

Asn Leu Glu Met Leu Asn Val Leu Phe Ser Pro Glu Ile Val Met Val
                725                 730                 735

Asp His Met Gly Glu Phe Val Leu Asp His Phe Ile His Leu Lys Gln
                740                 745                 750

Leu Gly Leu Ala Val Arg Met Ser Lys Ile Pro Asp Gln His Gln Phe
                755                 760                 765

Pro Pro His Leu Ala His Ile His Leu Val His Cys Val Met Lys Glu
                770                 775                 780

Asp Pro Met Pro Ile Leu Glu Lys Leu Leu His Leu Lys Ser Val Ala
785                 790                 795                 800

Leu Ser Tyr Gly Ala Phe Ile Gly Arg Arg Val Val Cys Ser Lys Gly
                805                 810                 815

Gly Phe Pro Gln Leu Cys Ala Leu Gly Ile Ser Gly Glu Ser Glu Leu
                820                 825                 830

Glu Glu Trp Ile Val Glu Gly Ser Met Pro Cys Leu Arg Thr Leu
                835                 840                 845

Thr Ile His Asp Cys Glu Lys Leu Lys Glu Leu Pro Asp Gly Leu Lys
850                 855                 860
```

```
Tyr Ile Thr Ser Leu Lys Glu Leu Lys Ile Arg Glu Met Lys Arg Glu
865                 870                 875                 880

Trp Lys Glu Lys Leu Val Pro Gly Gly Glu Asp Tyr Tyr Lys Val Gln
                885                 890                 895

His Ile Pro Asp Val Gln Phe Ile Asn Cys Asp Leu
            900                 905

<210> SEQ ID NO 42
<211> LENGTH: 901
<212> TYPE: PRT
<213> ORGANISM: Arabidopsis thaliana

<400> SEQUENCE: 42

Met Ala Glu Gly Val Val Ser Phe Gly Val Gln Lys Leu Trp Ala Leu
1               5                   10                  15

Leu Asn Arg Glu Ser Glu Arg Leu Asn Gly Ile Asp Glu Gln Val Asp
                20                  25                  30

Gly Leu Lys Arg Gln Leu Arg Gly Leu Gln Ser Leu Leu Lys Asp Ala
            35                  40                  45

Asp Ala Lys Lys His Gly Ser Asp Arg Val Arg Asn Phe Leu Glu Asp
50                  55                  60

Val Lys Asp Leu Val Phe Asp Ala Glu Asp Ile Ile Glu Ser Tyr Val
65                  70                  75                  80

Leu Asn Lys Leu Arg Gly Glu Gly Lys Gly Val Lys Asn His Val Arg
                85                  90                  95

Arg Leu Ala Cys Phe Leu Thr Asp Arg His Lys Val Ala Ser Asp Ile
            100                 105                 110

Glu Gly Ile Thr Lys Arg Ile Ser Lys Val Ile Gly Glu Met Gln Ser
        115                 120                 125

Leu Gly Ile Gln Gln Gln Ile Ile Asp Gly Gly Arg Ser Leu Ser Leu
130                 135                 140

Gln Asp Ile Gln Arg Glu Ile Arg Gln Thr Phe Pro Asn Ser Ser Glu
145                 150                 155                 160

Ser Asp Leu Val Gly Val Glu Gln Ser Val Glu Glu Leu Val Gly Pro
                165                 170                 175

Met Val Glu Ile Asp Asn Ile Gln Val Val Ser Ile Ser Gly Met Gly
            180                 185                 190

Gly Ile Gly Lys Thr Thr Leu Ala Arg Gln Ile Phe His His Asp Leu
        195                 200                 205

Val Arg Arg His Phe Asp Gly Phe Ala Trp Val Cys Val Ser Gln Gln
210                 215                 220

Phe Thr Gln Lys His Val Trp Gln Arg Ile Leu Gln Glu Leu Arg Pro
225                 230                 235                 240

His Asp Gly Glu Ile Leu Gln Met Asp Glu Tyr Thr Ile Gln Gly Lys
                245                 250                 255

Leu Phe Gln Leu Leu Glu Thr Gly Arg Tyr Leu Val Val Leu Asp Asp
            260                 265                 270

Val Trp Lys Glu Glu Asp Trp Asp Arg Ile Lys Glu Val Phe Pro Arg
        275                 280                 285

Lys Arg Gly Trp Lys Met Leu Leu Thr Ser Arg Asn Glu Gly Val Gly
290                 295                 300

Leu His Ala Asp Pro Thr Cys Leu Ser Phe Arg Ala Arg Ile Leu Asn
305                 310                 315                 320

Pro Lys Glu Ser Trp Lys Leu Phe Glu Arg Ile Val Pro Arg Arg Asn
```

```
              325                 330                 335
Glu Thr Glu Tyr Glu Glu Met Glu Ala Ile Gly Lys Glu Met Val Thr
            340                 345                 350
Tyr Cys Gly Gly Leu Pro Leu Ala Val Lys Val Leu Gly Gly Leu Leu
            355                 360                 365
Ala Asn Lys His Thr Ala Ser Glu Trp Lys Arg Val Ser Glu Asn Ile
        370                 375                 380
Gly Ala Gln Ile Val Gly Lys Ser Cys Leu Asp Asp Asn Ser Leu Asn
385                 390                 395                 400
Ser Val Tyr Arg Ile Leu Ser Leu Ser Tyr Glu Asp Leu Pro Thr Asp
                405                 410                 415
Leu Lys His Cys Phe Leu Tyr Leu Ala His Phe Pro Glu Asp Tyr Lys
                420                 425                 430
Ile Lys Thr Arg Thr Leu Tyr Ser Tyr Trp Ala Ala Glu Gly Ile Tyr
            435                 440                 445
Asp Gly Leu Thr Ile Leu Asp Ser Gly Glu Asp Tyr Leu Glu Glu Leu
        450                 455                 460
Val Arg Arg Asn Leu Val Ile Ala Glu Lys Ser Asn Leu Ser Trp Arg
465                 470                 475                 480
Leu Lys Leu Cys Gln Met His Asp Met Met Arg Glu Val Cys Ile Ser
                485                 490                 495
Lys Ala Lys Val Glu Asn Phe Leu Gln Ile Ile Lys Val Pro Thr Ser
                500                 505                 510
Thr Ser Thr Ile Ile Ala Gln Ser Pro Ser Arg Ser Arg Arg Leu Thr
                515                 520                 525
Val His Ser Gly Lys Ala Phe His Ile Leu Gly His Lys Lys Lys Val
        530                 535                 540
Arg Ser Leu Leu Val Leu Gly Leu Lys Glu Asp Leu Trp Ile Gln Ser
545                 550                 555                 560
Ala Ser Arg Phe Gln Ser Leu Pro Leu Leu Arg Val Leu Asp Leu Ser
                565                 570                 575
Ser Val Lys Phe Glu Gly Gly Lys Leu Pro Ser Ser Ile Gly Gly Leu
            580                 585                 590
Ile His Leu Arg Phe Leu Ser Leu His Gln Ala Val Ser His Leu
        595                 600                 605
Pro Ser Thr Ile Arg Asn Leu Lys Leu Met Leu Tyr Leu Asn Leu His
        610                 615                 620
Val Ala Ile Gly Val Pro Val His Val Pro Asn Val Leu Lys Glu Met
625                 630                 635                 640
Leu Glu Leu Arg Tyr Leu Ser Leu Pro Leu Asp Met His Asp Lys Thr
                645                 650                 655
Lys Leu Glu Leu Gly Asp Leu Val Asn Leu Glu Tyr Leu Trp Cys Phe
                660                 665                 670
Ser Thr Gln His Ser Ser Val Thr Asp Leu Leu Arg Met Thr Lys Leu
            675                 680                 685
Arg Phe Phe Gly Val Ser Phe Ser Glu Arg Cys Thr Phe Glu Asn Leu
        690                 695                 700
Ser Ser Ser Leu Arg Gln Phe Arg Lys Leu Glu Thr Leu Ser Phe Ile
705                 710                 715                 720
Tyr Ser Arg Lys Thr Tyr Met Val Asp Tyr Val Gly Glu Phe Val Leu
                725                 730                 735
Asp Phe Ile His Leu Lys Lys Leu Ser Leu Gly Val His Leu Ser Lys
                740                 745                 750
```

Ile Pro Asp Gln His Gln Leu Pro His Ile Ala His Ile Tyr Leu
        755                 760                 765

Leu Phe Cys His Met Glu Glu Asp Pro Met Pro Ile Leu Glu Lys Leu
    770                 775                 780

Leu His Leu Lys Ser Val Glu Leu Arg Arg Lys Ala Phe Ile Gly Arg
785                 790                 795                 800

Arg Met Val Cys Ser Lys Gly Gly Phe Pro Gln Leu Arg Ala Leu Gln
                805                 810                 815

Ile Ser Glu Gln Ser Glu Leu Glu Glu Trp Ile Val Glu Glu Gly Ser
            820                 825                 830

Met Pro Cys Leu Arg Asp Leu Ile Ile His Ser Cys Glu Lys Leu Glu
        835                 840                 845

Glu Leu Pro Asp Gly Leu Lys Tyr Val Thr Ser Leu Lys Glu Leu Lys
    850                 855                 860

Ile Glu Gly Met Lys Arg Glu Trp Lys Glu Lys Leu Val Gly Glu Asp
865                 870                 875                 880

Tyr Tyr Lys Val Gln His Ile Pro Asp Val Gln Phe Phe Asn Cys Asp
                885                 890                 895

Asp Glu Gln Arg Glu
            900

<210> SEQ ID NO 43
<211> LENGTH: 727
<212> TYPE: PRT
<213> ORGANISM: Arabidopsis thaliana

<400> SEQUENCE: 43

Met Lys Ser Leu Gly Ile Gln Glu Ile Ile Asp Gly Ala Ser Ser Met
1               5                   10                  15

Ser Leu Gln Glu Arg Gln Arg Glu Gln Lys Glu Ile Arg Gln Thr Phe
            20                  25                  30

Ala Asn Ser Ser Glu Ser Asp Leu Val Gly Val Glu Gln Ser Val Glu
        35                  40                  45

Ala Leu Ala Gly His Leu Val Glu Asn Asp Asn Ile Gln Val Val Ser
    50                  55                  60

Ile Ser Gly Met Gly Gly Ile Gly Lys Thr Thr Leu Ala Arg Gln Val
65                  70                  75                  80

Phe His His Asp Met Val Gln Arg His Phe Asp Gly Phe Ala Trp Val
                85                  90                  95

Phe Val Ser Gln Gln Phe Thr Gln Lys His Val Trp Gln Arg Ile Trp
            100                 105                 110

Gln Glu Leu Gln Pro Gln Asn Gly Asp Ile Ser His Met Asp Glu His
        115                 120                 125

Ile Leu Gln Gly Lys Leu Phe Lys Leu Leu Glu Thr Gly Arg Tyr Leu
    130                 135                 140

Val Val Leu Asp Asp Val Trp Lys Glu Asp Trp Asp Arg Ile Lys
145                 150                 155                 160

Ala Val Phe Pro Arg Lys Arg Gly Trp Lys Met Leu Leu Thr Ser Arg
                165                 170                 175

Asn Glu Gly Val Gly Ile His Ala Asp Pro Lys Ser Phe Gly Phe Lys
            180                 185                 190

Thr Arg Ile Leu Thr Pro Glu Glu Ser Trp Lys Leu Cys Glu Lys Ile
        195                 200                 205

Val Phe His Arg Arg Asp Glu Thr Gly Thr Leu Ser Glu Val Arg Val

-continued

```
                210                 215                 220
Asp Glu Asp Met Glu Ala Met Gly Lys Glu Met Val Thr Cys Cys Gly
225                 230                 235                 240

Gly Leu Pro Leu Ala Val Lys Val Leu Gly Leu Leu Ala Thr Lys
                245                 250                 255

His Thr Val Pro Glu Trp Lys Arg Val Tyr Asp Asn Ile Gly Pro His
                260                 265                 270

Leu Ala Gly Arg Ser Ser Leu Asp Asp Asn Leu Asn Ser Ile Tyr Arg
                275                 280                 285

Val Leu Ser Leu Ser Tyr Glu Asn Leu Pro Met Cys Leu Lys His Cys
    290                 295                 300

Phe Leu Tyr Leu Ala His Phe Pro Glu Tyr Tyr Glu Ile His Val Lys
305                 310                 315                 320

Arg Leu Phe Asn Tyr Leu Ala Ala Glu Gly Ile Ile Thr Ser Ser Asp
                325                 330                 335

Asp Gly Thr Thr Ile Gln Asp Lys Gly Glu Asp Tyr Leu Glu Glu Leu
                340                 345                 350

Ala Arg Arg Asn Met Ile Thr Ile Asp Lys Asn Tyr Met Phe Leu Arg
                355                 360                 365

Lys Lys His Cys Gln Met His Asp Met Met Arg Glu Val Cys Leu Ser
    370                 375                 380

Lys Ala Lys Glu Glu Asn Phe Leu Glu Ile Phe Lys Val Ser Thr Ala
385                 390                 395                 400

Thr Ser Ala Ile Asn Ala Arg Ser Leu Ser Lys Ser Arg Arg Leu Ser
                405                 410                 415

Val His Gly Gly Asn Ala Leu Pro Ser Leu Gly Gln Thr Ile Asn Lys
                420                 425                 430

Lys Val Arg Ser Leu Leu Tyr Phe Ala Phe Glu Asp Glu Phe Cys Ile
                435                 440                 445

Leu Glu Ser Thr Thr Pro Cys Phe Arg Ser Leu Pro Leu Leu Arg Val
    450                 455                 460

Leu Asp Leu Ser Arg Val Lys Phe Glu Gly Gly Lys Leu Pro Ser Ser
465                 470                 475                 480

Ile Gly Asp Leu Ile His Leu Arg Phe Leu Ser Leu His Arg Ala Trp
                485                 490                 495

Ile Ser His Leu Pro Ser Ser Leu Arg Asn Leu Lys Leu Leu Leu Tyr
                500                 505                 510

Leu Asn Leu Gly Phe Asn Gly Met Val His Val Pro Asn Val Leu Lys
                515                 520                 525

Glu Met Gln Glu Leu Arg Tyr Leu Gln Leu Pro Met Ser Met His Asp
    530                 535                 540

Lys Thr Lys Leu Glu Leu Ser Asp Leu Val Asn Leu Glu Ser Leu Met
545                 550                 555                 560

Asn Phe Ser Thr Lys Tyr Ala Ser Val Met Asp Leu Leu His Met Thr
                565                 570                 575

Lys Leu Arg Glu Leu Ser Leu Phe Ile Thr Asp Gly Ser Ser Asp Thr
                580                 585                 590

Leu Ser Ser Leu Gly Gln Leu Arg Ser Leu Glu Val Leu His Leu
                595                 600                 605

Tyr Asp Arg Gln Glu Pro Arg Val Ala Tyr His Gly Gly Glu Ile Val
    610                 615                 620

Leu Asn Cys Ile His Leu Lys Glu Leu Glu Leu Ala Ile His Met Pro
625                 630                 635                 640
```

```
Arg Phe Pro Asp Gln Tyr Leu Phe His Pro His Leu Ser His Ile Tyr
            645                 650                 655

Leu Trp Cys Cys Ser Met Glu Glu Asp Pro Ile Pro Ile Leu Glu Arg
            660                 665                 670

Leu Leu His Leu Lys Ser Val Ile Leu Thr Phe Gly Ala Phe Val Gly
            675                 680                 685

Arg Arg Met Val Cys Ser Lys Gly Gly Phe Pro Gln Leu Cys Phe Leu
            690                 695                 700

Lys Leu Glu Glu Leu Glu Glu Leu Glu Glu Trp Ile Val Glu Glu Gly
705                 710                 715                 720

Arg Cys His Phe Phe Val Leu
                725
```